United States Patent
Kawano et al.

(10) Patent No.: US 7,841,981 B2
(45) Date of Patent: Nov. 30, 2010

(54) BODY-INSERTABLE DEVICE SYSTEM AND BODY-INSERTABLE DEVICE GUIDING METHOD

(75) Inventors: Hironao Kawano, Hino (JP); Hironobu Takizawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 985 days.

(21) Appl. No.: 11/645,929

(22) Filed: Dec. 27, 2006

(65) Prior Publication Data

US 2007/0265496 A1 Nov. 15, 2007

(30) Foreign Application Priority Data

Dec. 28, 2005 (JP) ............................. 2005-380456

(51) Int. Cl.
*A61B 1/04* (2006.01)
(52) U.S. Cl. .................. 600/118; 600/101; 600/109; 600/117; 600/424
(58) Field of Classification Search .............. 600/101, 600/109, 114, 117, 118, 407, 409–410, 414–416, 600/421–424
See application file for complete search history.

(56) References Cited

U.S. PATENT DOCUMENTS

| | | | | |
|---|---|---|---|---|
| 7,122,001 | B2* | 10/2006 | Uchiyama et al. | 600/103 |
| 7,398,117 | B2* | 7/2008 | Minai et al. | 600/424 |
| 7,509,158 | B2* | 3/2009 | Minai et al. | 600/424 |
| 7,623,904 | B2* | 11/2009 | Uchiyama et al. | 600/424 |
| 2003/0045790 | A1* | 3/2003 | Lewkowicz et al. | 600/407 |
| 2003/0229268 | A1* | 12/2003 | Uchiyama et al. | 600/109 |
| 2004/0181127 | A1* | 9/2004 | Matsumoto et al. | 600/101 |

(Continued)

FOREIGN PATENT DOCUMENTS

JP 2002-336188 11/2002

(Continued)

OTHER PUBLICATIONS

Korean Office Action dated May 13, 2010.

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

An object of the present invention is that the examiner easily picks up a series of images over a desired region in a desired digestive tract without such troublesome examination work that the examiner successively knows the imaging field to the inside of the digestive tract. A body-insertable device system of the invention includes a capsule endoscope 1, a permanent magnet 3, and a position display sheet 2. In the capsule endoscope 1, a imaging unit for picking up the images of the insides of an subject 100, and a magnet are contained in a casing. The capsule endoscope sends a radio signal containing information of the images of the insides of the subject 100 to outside the capsule endoscope. The permanent magnet 3 generates a magnetic field for application to the capsule endoscope 1 in liquid Lq1 having been introduced into the subject 100 and changes at least one of a position and a posture of the capsule endoscope 1 by the magnetic field. The position display sheet 2 visually presents an approaching position of the subject 100 that the permanent magnet 3 approaches to generate a magnetic field.

33 Claims, 36 Drawing Sheets

U.S. PATENT DOCUMENTS

| | | | |
|---|---|---|---|
| 2004/0236180 A1* | 11/2004 | Uchiyama et al. | 600/109 |
| 2005/0143642 A1* | 6/2005 | Minai et al. | 600/407 |
| 2005/0143643 A1* | 6/2005 | Mimai et al. | 600/407 |
| 2005/0143647 A1* | 6/2005 | Minai et al. | 600/410 |
| 2005/0143648 A1* | 6/2005 | Minai et al. | 600/410 |
| 2005/0143649 A1* | 6/2005 | Minai et al. | 600/410 |
| 2005/0216231 A1* | 9/2005 | Aoki et al. | 702/183 |

FOREIGN PATENT DOCUMENTS

| | | |
|---|---|---|
| JP | 2003-325682 | 11/2003 |
| JP | 2004-017022 | 1/2004 |
| JP | 2004-255174 | 9/2004 |
| JP | 2004-529718 | 9/2004 |
| JP | 2005-013338 | 1/2005 |
| JP | 2005-285857 | 10/2005 |
| KR | 10-0457752 | 1/2004 |
| WO | WO 02/095351 A3 | 11/2002 |
| WO | WO 2005/032370 A1 | 4/2005 |

\* cited by examiner

BODY-INSERTABLE DEVICE SYSTEM AND BODY-INSERTABLE DEVICE GUIDING METHOD

CROSS-REFERENCE TO RELATED APPLICATIONS

This application is based upon and claims the benefit of priority from Japanese Patent Application No. 2005-380456, filed Dec. 28, 2005, the entire contents of which are incorporated herein by reference.

BACKGROUND OF THE INVENTION

1. Field of the Invention

The present invention relates to a body-insertable device system which introduces a capsule type body-insertable device into a subject and acquires images of the interior of the subject picked up by the body-insertable device, and a body-insertable device guiding method.

2. Description of the Related Art

Recently, in the field of endoscopes, there is proposed a capsule type body-insertable device (for example, a capsule endoscope) having imaging and radio communication functions. There has been developed a body-insertable device system which acquires images in the subject by using the capsule endoscope. To observe (examine) the insides of the subject, the capsule endoscope is swallowed from the mouth of a subject, for example, and then the endoscope peristaltically moves in the body cavity or in the internal organs, such as stomach and small intestine and picks up images in the subject at intervals for example of 0.5 second until the endoscope is naturally discharged.

The images picked up by the capsule endoscope during the movement of the capsule endoscope in the subject is received by an external display device by way of an antenna attached on the surface of the subject. The display device is wirelessly communicable with the capsule endoscope and capable of storing the images, and successively stores the images received from the capsule endoscope in the subject to a memory. A doctor or a nurse displays the images stored in the display device, i.e., the images of the insides of the digestive tract of the subject, and observes (examines) the insides of the subject to diagnose the subject.

A medical device guiding system is known as such a body-insertable device system. In the medical guiding system, a capsule endoscope is introduced into the subject. The endoscope is constructed such that a protruded member, spirally shaped, is provided on the outer surface of the casing thereof, and a magnetic material is fastened to the inside of the casing. A rotating magnetic field is applied to the capsule endoscope from the outside of the subject, and by controlling the rotating magnetic field, the capsule endoscope is guided to a desired region in the subject. In such a medical device guiding system, the capsule endoscope having been introduced into the subject changes the position and the direction of the endoscope itself by the rotating magnetic field applied from the outside of the subject (Japanese Patent Application Laid-Open No. 2004-255174).

The doctor successively displays a series of images picked up over a desired region as an observation region in the digestive tract on the display, and observes the insides of the desired digestive tract in the subject. In this case, the doctor is required to guide the capsule endoscope having been introduced into the digestive tract, to change the imaging field in the digestive tract, and to cause the capsule endoscope to pick up images over the desired region in the digestive tract.

In the conventional body-insertable device system, to change the imaging field of the capsule endoscope having been introduced into a desired digestive tract over the desired region in the digestive tract, the doctor views the images of the insides of the digestive tract, which are displayed on the display, (images picked up by the capsule endoscope having been introduced into the digestive tract) and guides the capsule endoscope while knowing the current position of the capsule endoscope at a time point of picking up the image of the insides of the digestive tract. High skill and much experience are required for the guiding of the capsule endoscope. Only a highly skilled doctor can guide the capsule endoscope so as to change the imaging field over the desired region in the digestive tract without difficulty. This fact indicates that much time and labor are consumed to pick up a series of images over the desired region in the digestive tract as the desired observation region, and the highly skilled doctor is tied to the guiding operation of the capsule endoscope for a long time.

SUMMARY OF THE INVENTION

At least one object of the present invention is to solve the problems.

A body-insertable device system according to one aspect of the present invention includes a body-insertable device containing therein an imaging unit which picks up images of an inside of a subject and a magnetic material; a magnetic field generating unit which generates a magnetic field to the magnetic material of the body-insertable device having been introduced into the subject and changes at least one of a position and a posture of the body-insertable device by the magnetic field; and a position presenting unit which visually presents an approaching position of the subject in the magnetic field generating unit.

A method for guiding a body-insertable device, which contains an imaging unit for picking up images of the inside of a subject and a magnetic material and is guided by a magnetic field, according to another aspect of the present invention includes a position presenting step of visually presenting a magnetic-field generating position located near the subject; and a magnetic-field generating step of generating the magnetic field at the magnetic-field generating position presented in the position presenting step.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Suitable embodiments of a body-insertable device system and a body-insertable device guiding method of the present invention will be described in details with reference to the accompanying drawings. It should be understood that the invention is not limited to those embodiments.

First Embodiment

Figure 1:
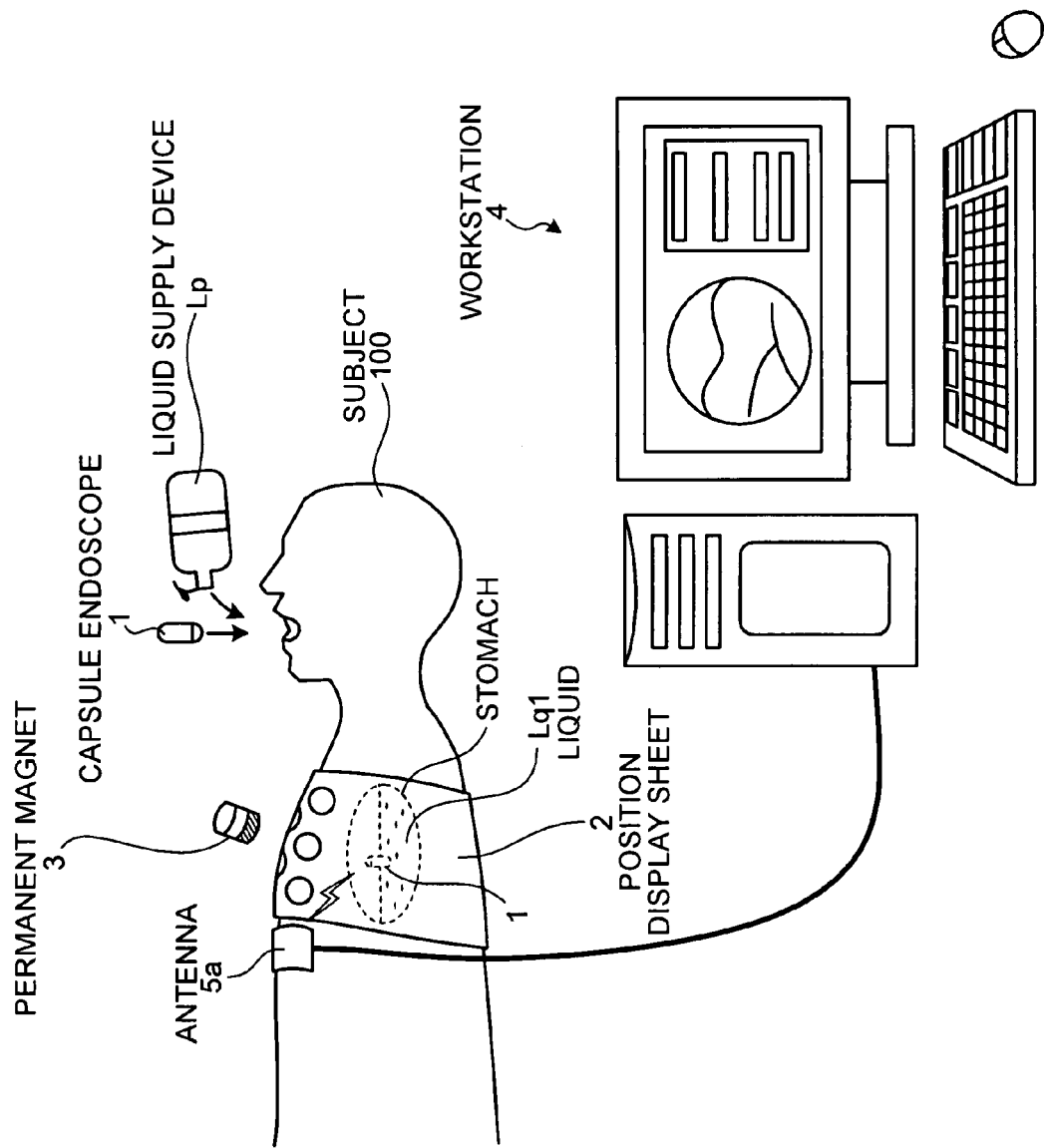
FIG. 1 is a schematic diagram showing a configuration example of a body-insertable device system in a first embodiment of the present invention.

FIG. 1 is a schematic diagram showing a configuration example of a body-insertable device system in a first embodiment of the present invention. As shown in FIG. 1, the body-insertable device system of the first embodiment is made up of a capsule endoscope 1 which is introduced into a subject 100 and picks up images in an digestive tract of the subject 100, a liquid supply device Lp for supplying a liquid Lq1 for floating the capsule endoscope 1 into the subject 100, a permanent magnet 3 for controlling at least one of a position and a posture of the capsule endoscope 1 that floats in the liquid Lq1, a position display sheet 2 for visually presenting positions on the body surface of the subject to which the permanent magnet 3 is moved closer to the subject 100, and a workstation 4 for displaying images picked up by the capsule endoscope 1 on the display.

The capsule endoscope 1 has an imaging function to pick up images in the subject 100 and a radio communication function for transmitting various types of information, including pickup images, to the workstation 4. The capsule endoscope 1 is sized so as to be easily inserted into the subject 100, and a specific gravity of the endoscope is almost equal to or smaller than that of the liquid Lq1. When the capsule endoscope 1 is swallowed by the subject, the capsule endoscope 1 moves in the digestive tract, urged by a peristaltic motion or the like, and the capsule endoscope picks up images in the digestive tract at intervals of 0.5 second, for example. The capsule endoscope 1 sends the thus picked up images of the insides of the digestive tract to the workstation 4.

The liquid supply device Lp supplies the liquid Lq1 for floating the capsule endoscope 1 into the subject 100. More specifically, the liquid supply device Lp contains desired liquid Lq1, such as water or a saline solution, and supplies the liquid Lq1 into the subject 100 from the mouth. The liquid Lq1 supplied from the liquid supply device Lp is introduced into the stomach or the like of the subject 100, for example, and floats the capsule endoscope 1 inside the subject 100.

The permanent magnet 3 functions as a magnetic field generating unit for changing at least one of the position and the posture of the capsule endoscope 1 in the subject 100. Specifically, the permanent magnet 3 generates a magnetic field to the capsule endoscope 1 having been introduced into an internal part (stomach, for example) of the subject 100, and controls a motion of the capsule endoscope 1 (i.e., motion of the casing) in the liquid Lq1 by the magnetic force of the magnetic field. The permanent magnet 3 controls at least one of the position and the posture of the capsule endoscope 1 in the subject 100 by controlling the motion of the capsule endoscope 1, to thereby change at least one of the position and the posture of the capsule endoscope 1. The capsule endoscope 1 contains a magnetic material which reacts to the magnetic force applied from the permanent magnet 3 to move the casing of the capsule endoscope.

The permanent magnet 3 may consist of a single permanent magnet having a given magnetic force. However, it is desirable that a plurality of permanent magnets of which the magnetic forces are different from one another are prepared, and one of those permanent magnets is selected in use. In this case, it suffices that a permanent magnet that is capable of generating a magnetic field that depending on a body shape (height, weight, waist, etc.) of the subject 100 or a motion (movement and/or swing) of the capsule endoscope 1 is selected for the permanent magnet 3.

The position display sheet 2 serves as position presenting unit which visually presents to the doctor or the nurse a specific position on the body surface of the subject 100 to which the permanent magnet 3 is moved to the body surface (this position will be referred to as an approaching position). Specifically, when the position display sheet 2 is attached to the subject 100, the position display sheet 2 visually presents to the examiner an approaching position of the permanent magnet 3 on the body surface of the subject 100. The permanent magnet 3 is moved close to the approaching position and generates a magnetic field toward the capsule endoscope 1 in the digestive tract, and is ready for controlling at least one of the position and the posture of the capsule endoscope 1. To change at least one of the position and the posture of the capsule endoscope 1 in the subject 100 by using the permanent magnet 3, the examiner moves the permanent magnet 3 to the approaching position presented by the position display sheet 2 and controls the operation of the capsule endoscope 1 in the subject 100. Operations of the permanent magnet 3 which changes at least one of the position and the posture of the capsule endoscope 1 in the subject 100 will be described later.

The workstation 4 has a radio communication function to receive various types of information such as images picked up by the capsule endoscope 1, and a display function to display images or the like received from the capsule endoscope 1. Specifically, the workstation 4 has an antenna 5a for transmitting and receiving radio signals to and from the capsule endoscope 1, and acquires various types of information from the capsule endoscope 1 through the antenna 5a placed on the body surface of the subject 100. In this case, the workstation 4 functions as a display device for displaying images of the inside of the subject 100 picked up by the capsule endoscope 1. The workstation 4 is also capable of transmitting control signals for controlling the driving of the capsule endoscope 1 (for example, control signals for controlling the start or stop of the imaging operation of the capsule endoscope 1) via such an antenna 5a.

The antenna 5a is formed with, for example, a loop antenna which is used for transmitting and receiving radio signals to the workstation and the capsule endoscope 1. Specifically, the antenna 5a, as shown in FIG. 1, is located at a position on the body surface of the subject 100, such as vicinity of the stomach of the subject 100. In this case, the antenna 5a enables radio communication between the capsule endoscope 1 having been introduced into the stomach of the subject 100 and the workstation 4. It suffices that the antenna 5a is placed on positions on the body surface of the subject 100, which lie on a route along which the capsule endoscope 1 moves in the subject 100. The number of the antenna 5a is not limited to one, but a plurality of antennae may be used.

Figure 2:
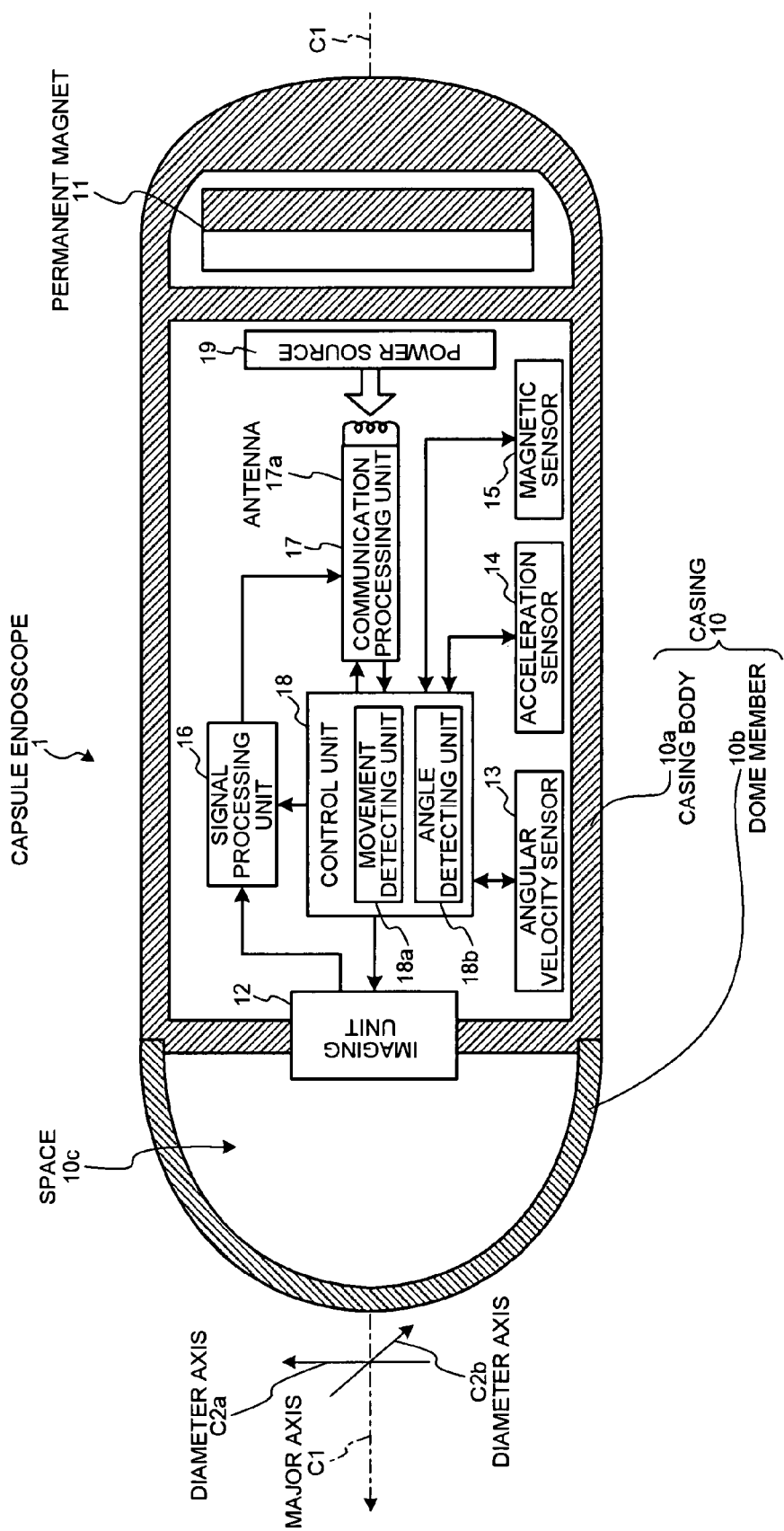
FIG. 2 is a schematic diagram showing a configuration example of the capsule endoscope in the first embodiment.

The capsule endoscope 1, which is one example of the body-insertable device constructed according to the present invention, will be described in detail. FIG. 2 is a schematic diagram showing a configuration example of the capsule endoscope 1. As shown in FIG. 2, the capsule endoscope 1 includes a casing 10 which is shaped like a capsule and sized so that it is easily introduced into the subject 100, and a permanent magnet 11 for moving the casing 10 by a magnetic force generated by the permanent magnet 3. The capsule endoscope 1 is composed of an imaging unit 12 for imaging inside the subject 100, an angular sensor 13 for detecting an angular velocity when the casing 10 swings, an acceleration sensor 14 for detecting an acceleration when the casing 10 moves, and a magnetic sensor 15 for detecting an intensity of a magnetic field applied to the capsule endoscope 1. Further, the capsule endoscope 1 includes a signal processing unit 16 for generating an image signal corresponding to an image picked up by the imaging unit 12, an antenna 17a for transmitting and receiving a radio signal to and from the external antenna 5a and a communication processing unit 17 which modulates various kinds of signals such as image signals for transmission to the external workstation 4 into radio signals, and demodulates radio signals received through the antenna 17a. The capsule endoscope 1 includes a control unit 18 for controlling the driving of each constituent components of the capsule endoscope 1, and a power source 19 for supplying driving power to those components.

The casing 10 is shaped like a capsule and sized so that it is easily introduced into the subject 100, and includes a casing body 10a containing the constituent components of the capsule endoscope 1, and a dome member 10b forming a front end of the casing 10. The casing body 10a, as shown in FIG. 2, includes the permanent magnet 11 and the power-source 19, which are closer to a rear end of the casing 10 than the center of the casing, and contains the imaging unit 12 in the front end of the casing. The dome member 10b is a dome-shaped member made of a substantially transparent material allowing light to pass therethrough, and is attached to the front end of the casing body 10a while covering the imaging unit 12. In this case, the dome member 10b forms a space 10c defined by an inner surface of the dome member 10b and the front end of the capsule endoscope casing body 10a. The casing 10 that is formed with the casing body 10a and the dome member 10b has a specific gravity, which is almost equal to or smaller than that of the liquid Lq1, and has the center of gravity located closer to the rear end side.

The permanent magnet 11 is provided for moving the casing 10 by a magnetic force of a magnetic field externally generated. Specifically, the permanent magnet 11 magnetizes the casing 10 in the longitudinal direction of the casing 10. For example, when the external permanent magnet 3 generates a magnetic field to the permanent magnet 11, the magnetic-force applied by the magnetic field moves or swings the casing 10 in the liquid Lq1. In turn, the permanent magnet 11 changes at least one of the position and the posture of the capsule endoscope 1 in the liquid Lq1 by its magnetic force.

A posture of the capsule endoscope 1 referred to in the specification is a posture of the casing 10 defined in a given spatial coordinate system xyz. Specifically, assuming that a major axis C1 that is directed from the rear end to the front end is set as an axial vector on the center axis of the casing 10 as viewed in the longitudinal axis, a posture of the capsule endoscope 1 is defined by the direction of the major axis C1. A position of the capsule endoscope 1 referred to in the specification is determined by the position coordinates of the casing 10 in the spatial coordinate system xyz. Thus, when the capsule endoscope 1 is introduced into the subject 100, a posture of the capsule endoscope 1 in the subject 100 is determined by a direction of the major axis C1 in the spatial coordinate system xyz, and a position of the capsule endoscope 1 in the subject 100 is determined by the position coordinates of the casing 10 in the spatial coordinate system xyz.

The imaging unit 12 picks up images inside the digestive tract of the subject 11, for example. To be more specific, the imaging unit 12 is made up of an imaging device such as CCD or CMOS, a light emitting device such as LED for illuminating an imaging field of the imaging device, and an optical system such as lens element for forming an image of light reflected from the imaging field on the imaging device. The imaging unit 12 is fixed to the front end of the casing body 10a as stated above, and forms an image of light that is reflected from the imaging field and received through the dome member 10b, thereby picking up an image in the digestive tract of the subject 100, for example. The imaging unit 12 transmits image information thus obtained to the signal processing unit 16. A wide-angle optical system is desirably used for the optical system of the imaging unit 12. Where such a wide-angle optical system is used, the imaging unit 12 has a field angle of approximately 100 to 140°, for example, ensuring a wide imaging field. In the body-insertable device system of the first embodiment, the insides of the subject 100 are observed at high level when the capsule endoscope 1 having such a wide imaging field is used.

The direction of the imaging field of the imaging unit 12 fixedly located in the casing 10 is determined by the direction of the casing 10 in the spatial coordinate system xyz. A light receiving surface of the imaging unit 12 is arranged to be vertical to a given direction on the casing 10, for example, the major axis C1. In this case, the center axis (i.e., optical axis) of the imaging field of the imaging unit 12 is substantially coincident with the major axis C1, and the light receiving surface of the imaging unit 12 is parallel to the diameter axes C2a and C2b as axis vectors vertical to the major axis C1. The diameter axes C2a and C2b are the axis vectors in the radial direction of the casing 10, and the major axis C1 is orthogonal to the diameter axes C2a and C2b. In the imaging unit 12, the direction of the major axis C1 in the spatial coordinate system xyz determines the normal line direction of the light receiving surface, or the direction of the imaging field. And, a rotation angle of the diameter axis C2a with respect to the rotation center of the major axis C1 determines a rotation angle of the light receiving surface, or a rotation angle of the imaging field with respect to the rotation angle of the major axis C1.

An angular velocity sensor 13 is used for detecting an angular velocity of the casing 10 when the posture of the capsule endoscope 1 changes. To be more specific, the angular velocity sensor 13 may be a MEMS gyro. The angular velocity sensor detects an angular velocity of the casing 10 when it rotates, and an angular velocity of the major axis C1 when its direction changes in the spatial coordinate system xyz. The angular velocity sensor 13 detects an angular velocity of the casing 10 when the casing rotates with respect to the major axis C1. In this case, the angular velocity sensor 13 detects an angular velocity of the diameter axis C2a when it rotates with respect to the major axis C1. The angular velocity sensor 13 transmits the results of detecting such angular velocities to the control unit 18.

The acceleration sensor 14 is used for detecting an acceleration of the casing 10 when the capsule endoscope 1 moves. Specifically, the acceleration sensor 14 detects an acceleration of the casing 10 when it moves, viz., an acceleration of the casing 10 when the position coordinates representative of the casing change in the spatial coordinate system xyz. In this case, the acceleration sensor 14 detects the magnitude and the direction of an acceleration of the casing 10. The acceleration sensor 14 sends such an acceleration detection result to the control unit 18.

The magnetic sensor 15 detects an intensity of an external magnetic field, which acts on the capsule endoscope 1. Specifically, when the external permanent magnet 3, for example, generates a magnetic field toward the capsule endoscope 1, the magnetic sensor 15 detects an intensity of the magnetic field applied to the capsule endoscope 1 from the permanent magnet 3. The magnetic sensor 15 sends the results of such a magnetic field intensity detection to the control unit 18.

The signal processing unit 16 generates an image signal corresponding to an image picked up by the imaging unit 12. Specifically, the signal processing unit 16 generates an image signal including image information, which is received from the imaging unit 12. The signal processing unit 16 includes motion information (to be described later) of the casing 10, which is received from the control unit 18, into the blanking periods of the image signal. As a result, the signal processing unit 16 associates the image picked up by the imaging unit 12 with motion information of the casing 10 at the time of picking up the image. The signal processing unit 16 sends the image signal including the image information and the motion information to the communication processing unit 17.

The communication processing unit 17 modulates the image signal that is received from the signal processing unit 16, in a given modulation mode into a radio signal. The communication processing unit 17 likewise demodulates a magnetic-field detection signal (to be described later) that is received from the control unit 18, into a radio signal. The communication processing unit 17 outputs the radio signal thus formed to the antenna 17a. The antenna 17a is a coil antenna, for example, and applies the radio signal that is received from the communication processing unit 17 to the external antenna 5a, for example. In this case, the radio signal is received by the workstation 4 by way of the antenna 5a. The communication processing unit 17 receives a radio signal from the workstation 4 by way of the antenna 17a. In this case, the communication processing unit 17 demodulates the radio signal received by the antenna 17a in a given demodulation mode into a control signal issued from the workstation 4. Subsequently, the communication processing unit 17 transmits the thus formed control signal and the like to the control unit 18.

The control unit 18 controls the imaging unit 12, the angular velocity sensor 13, the acceleration sensor 14, the magnetic sensor 15, the signal processing unit 16 and the communication processing unit 17 for the driving and signal flows. In this case, the control unit 18 controls the operation timings of the imaging unit 12, the angular velocity sensor 13 and the acceleration sensor 14 so as to detect an angular velocity and an acceleration of the casing 10 when the imaging unit 12 picks up images. When receiving the control signal by the workstation 4 from the communication processing unit 17, the control unit 18 starts or stops the driving of the imaging unit 12 according to the control signal. In this case, the control unit 18 controls the driving of the imaging unit 12 according to a control signal for imaging start so that the imaging unit 12 picks up images in the subject 100 at intervals of 0.5 second, for example, and stops the driving of the imaging unit 12 according to a control signal for imaging stop. Further, the control unit 18 recognizes an intensity of an external magnetic field on the basis of the detection result received from the magnetic sensor 15, and sends a magnetic-field detection signal representative of the magnetic field intensity to the communication processing unit 17.

The control unit 18 may control the driving of the imaging unit 12 according to the control signal from the workstation 4 as mentioned above or may start the driving control of the imaging unit 12 after a predetermined time elapses from the start of supplying driving power by the power source 19.

The control unit 18 includes a movement quantity detecting unit 18a for detecting a quantity of movement of the casing 10 when the capsule endoscope 1 moves, and an angle detecting unit 18 for detecting a rotation angle of the casing 10 when the posture of the capsule endoscope 1 changes. The movement quantity detecting unit 18a integrates the acceleration detected by the acceleration sensor 14 to produce a movement quantity of the casing 10 defined in the spatial coordinate system xyz. The movement quantity calculated by the movement quantity detecting unit 18a takes the form of vector quantity representing a distance and a direction of the movement of the casing 10 in the spatial coordinate system xyz. The movement quantity detecting unit 18a integrates an angular velocity detected by the angular velocity sensor 13 to produce a rotation angle of the major axis C1 and that of the diameter axis C2a in the spatial coordinate system xyz. The control unit 18 transmits to the signal processing unit 16 the movement quantity detected by the movement quantity detecting unit 18b and each rotation angle detected by the angle detecting unit 18b in the form of movement information on the casing 10.

Figure 3:
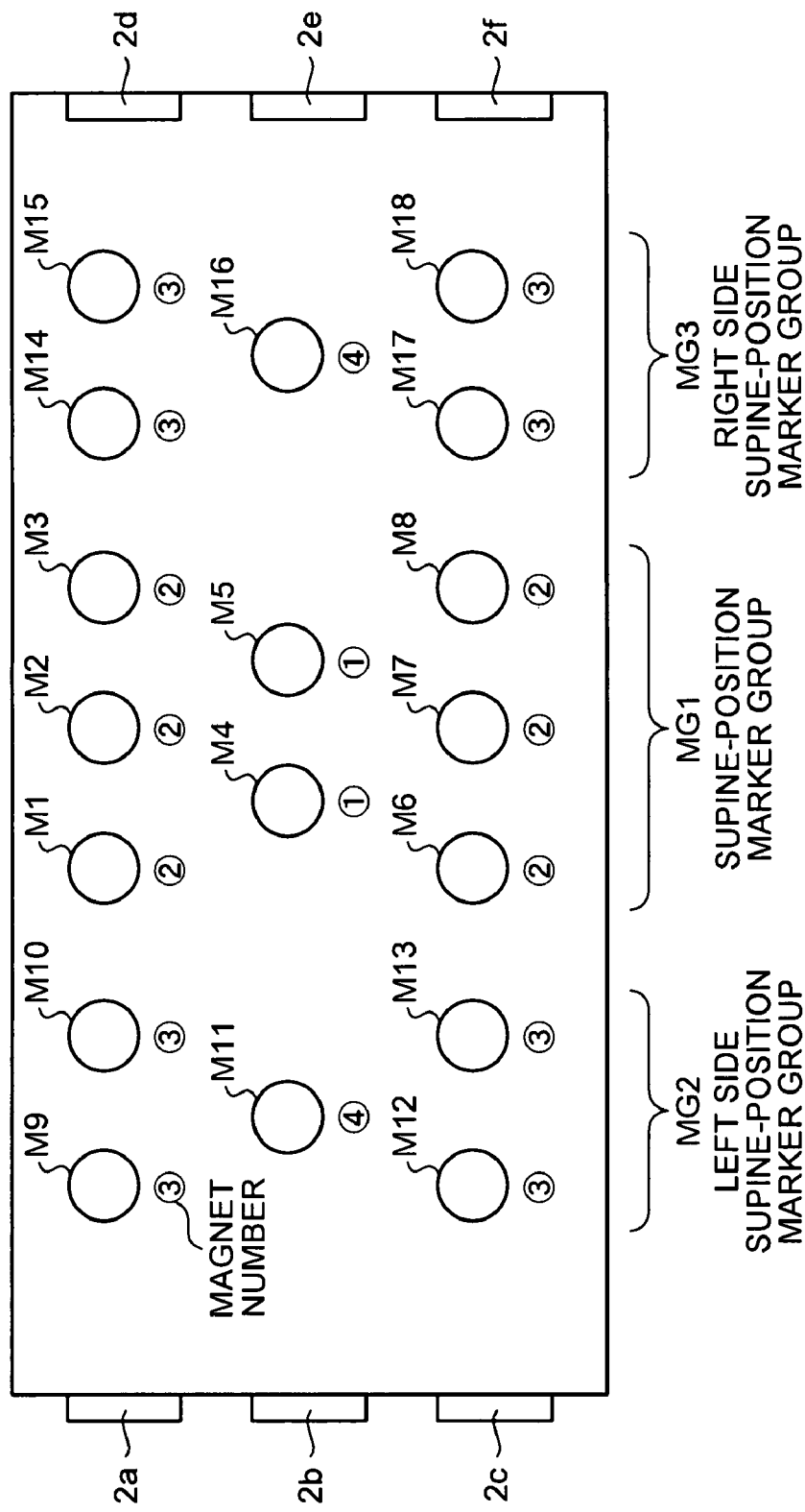
FIG. 3 is a schematic diagram showing a configuration example of a position display sheet in the first embodiment.

The position display sheet 2 in the body-insertable device system in the first embodiment of the invention, will be described in detail. FIG. 3 is a schematic diagram showing a configuration example of the position display sheet 2. As shown in FIG. 3, the position display sheet 2 is a sheet-like member on which a plurality of markers for indicating the approaching positions already stated to the examiner are formed. Specifically, the position display sheet 2 is a bendable sheet-like member made of cloth, paper, resin or the like. As shown in FIG. 3, for example, a plurality of markers M1 to M18 indicating the approaching positions are formed on the position display sheet 2. The position display sheet 2 contains at least one approaching position presented by the position display sheet 2. The number of approaching positions is not limited to 18.

The markers M1 to M18 present the examiner the approaching positions on the body surface to which the permanent magnet 3 is allowed to move. Each of the markers M1 to M18 may be shaped to take any desired form such as a circle. When the position display sheet 2 is attached to the subject 100, the position display sheet presents the approaching positions on the body surface of the subject 100. Those markers M1 to M18 are grouped for each posture of the subject 100 such as a supine position, and represent the approaching positions that are different for each posture of the subject 100. The markers M1 to M18 are sorted into three groups, a supine-position marker group MG1, a left side supine-position marker group MG2 and a right side supine-position marker group MG3.

The supine-position marker group MG1 is for indicating the approaching positions of the subject 100, who is in a supine position, to which the permanent magnet 3 is closely moved, and include markers M1 to M8. The left side supine-position marker group MG2 is for indicating the approaching positions of the subject 100, who is in a left side supine position, to which the permanent magnet 3 is closely moved, and include markers M9 to M13. The right side supine-position marker group MG3 is for indicating the approaching positions of the subject 100, who is in a right side supine position, to which the permanent magnet 3 is closely moved, and include markers M14 to M18. The examiner moves the permanent magnet 3 close to all the approaching positions indicated by the markers M1 to M18, and changes at least one of the position and the posture of the capsule endoscope 1 in the liquid Lq1, which has been introduced into a desired digestive tract (e.g., stomach) of the subject 100 to thereby change the imaging field over the substantially entire region in the digestive tract, thereby causing the capsule endoscope 1 to pick up a series of images over the substantially entire region of the sides of the digestive tract.

In the position display sheet 2, as shown in FIG. 3, for example, magnetic numbers are associatively placed near the markers M1 to M18. Those magnetic numbers are used for specifically indicating the plurality of permanent magnets, respectively, and form select information for selecting from the plurality of permanent magnets a proper permanent magnet 3 to be brought close to the subject 100. To be more specific, when the examiner brings the permanent magnet 3 close to an approaching position indicated by one of those markers M1 to M18, he/she selects from those permanent magnets a permanent magnet specified by the magnetic number located near the marker associated with the approaching position. When the permanent magnet is moved close to the approaching position indicated by the marker M9, for example, the examiner selects a permanent magnet specified by a magnet number (3) from the permanent magnets prepared before hand, and moves the permanent magnet of the magnetic number (3) close to the marker M9.

The select information placed near the markers is not limited to the magnet numbers, but may be any of suitable patterns such as appropriate symbols or figures, if it is able to specifically indicate the permanent magnets. It may also be information indicative of a magnetic intensity of a magnetic field generated or a magnetic force thereof. In this case, the examiner selects from the permanent magnets prepared before hand a permanent magnet having a magnetic intensity or a magnetic force indicated by the select information. Such select information may be expressed as in the following. The illustrated marker shapes of the markers M1 to M18 per se are made to differ for each magnet. If so done, the marker per se directly indicates the approaching position, and the select information for the permanent magnet to be moved close to the approaching position may be expressed in shapes.

Figure 4:
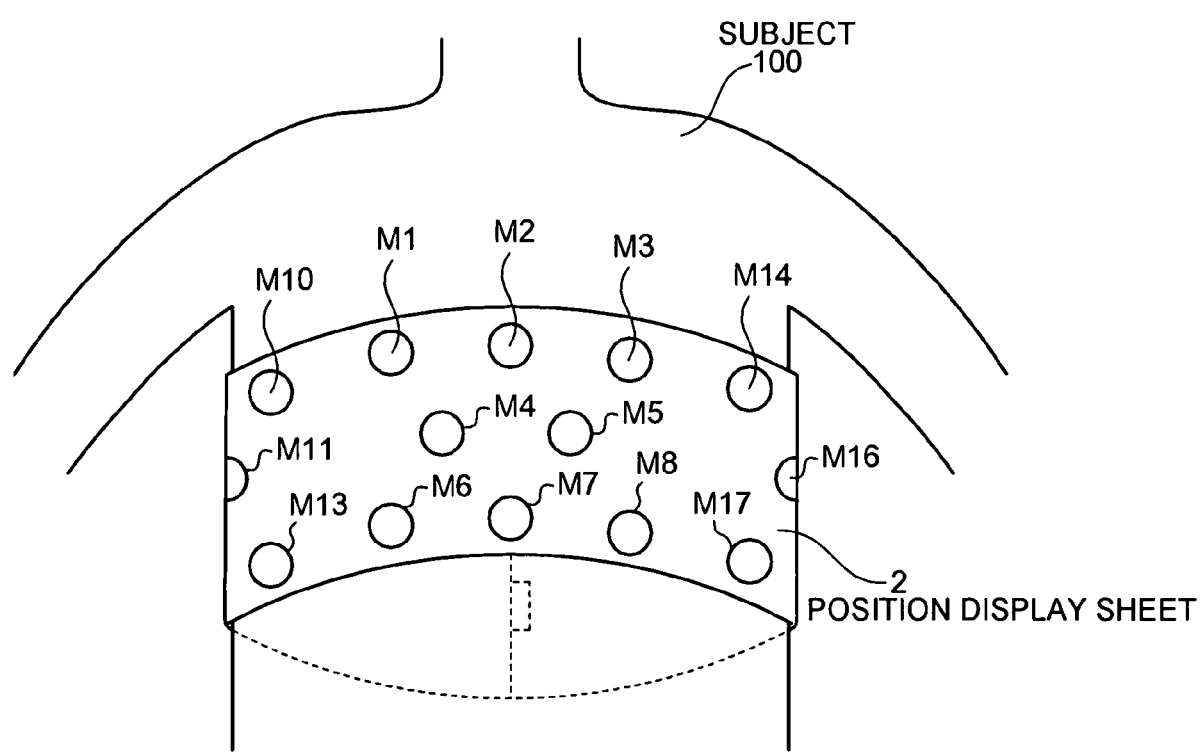
FIG. 4 is a schematic diagram showing the position display sheet attached to the subject.

Protruded parts 2a to 2c and recessed parts 2d to 2f are respectively provided in the vicinity of both ends of the position display sheet 2, which are opposite to each other. The protruded parts 2a to 2c and the recessed parts 2d to 2f form a pair of connector groups for interconnecting both ends of the position display sheet 2. Specifically, the protruded part 2a and the recessed part 2d form a pair of connectors; the protruded part 2b and the recessed part 2e, a pair of connectors; and the protruded part 2c and the recessed part 2f, a pair of connectors. In this case, when the protruded parts 2a to 2c are combined to the recessed parts 2d to 2f, respectively, the position display sheet 2 takes a cylindrical form with both ends thereof being combined with each other. To attach the position display sheet 2 to the subject 100 for example as shown in FIG. 4, the position display sheet 2 is wound around the trunk of the subject 100, and the protruded parts 2a to 2c are combined with the recessed parts 2d to 2f, respectively. When the position display sheet 2 is attached to the subject 100, the markers M1 to M18 are placed facing outside to present to the examiner the approaching position of the subject 100 to which the permanent magnet 3 is closely moved.

Figure 5:
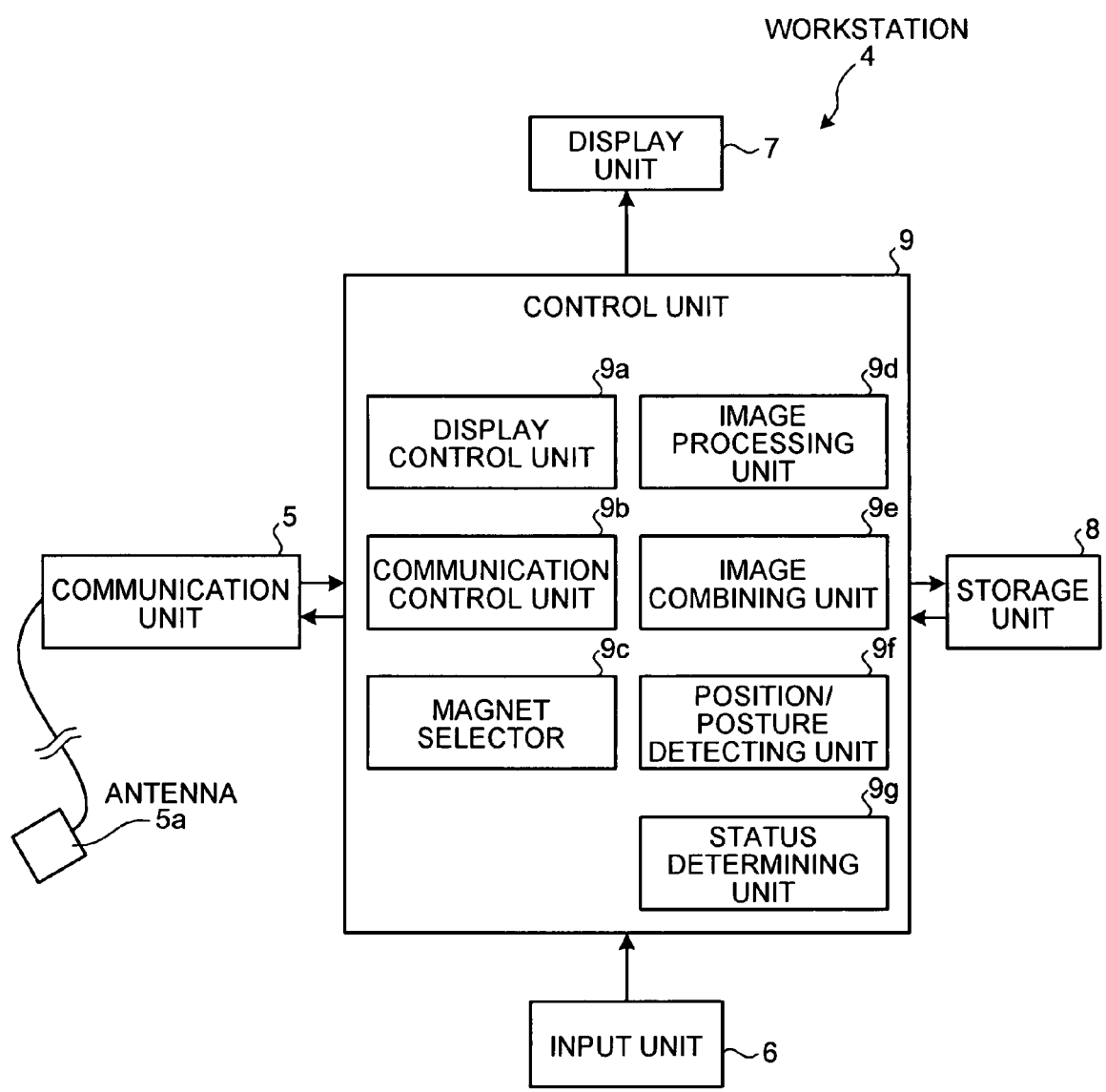
FIG. 5 is a block diagram schematically showing a configuration example of a workstation in the first embodiment.

The workstation 4 used in the body-insertable device system in the first embodiment of the invention, will be described in detail. FIG. 5 is a block diagram schematically showing a configuration example of the workstation 4. As shown in FIG. 5, the workstation 4 is made up of a communication unit 5 for performing a radio communication with the capsule endoscope 1 by using the antenna 5a, an input unit 6 for inputting various types of information to the workstation 4, a display unit 7 for displaying images picked up by the capsule endoscope 1, and the like, a storage unit 8 for storing various types of information such as image information, and a control unit 9 for controlling operations of the components of the workstation 4.

The communication unit 5, connected to the antenna 5a by means of cables, receives a radio signal with the aid of the antenna 5a, and demodulates the signal in a given demodulation mode to thereby acquire various information from the capsule endoscope 1. In this case, the communication unit 5 acquires image information obtained by the imaging unit 12 and motion information of the casing 10, and sends the acquired image and motion information to the control unit 9. The communication unit 5 acquires a magnetic-field detection signal representing a magnetic intensity detected by the magnetic sensor 15, and sends the acquired magnetic-field detection signal to the control unit 9. The communication unit 5 modulates a control signal that is received from the control unit 9 and is applied to the capsule endoscope 1, in a given modulation mode, into a radio signal. In this case, the communication unit 5 sends the signal thus formed to the antenna 5a, and sends the radio signal to the capsule endoscope 1 with the aid of the antenna 5a. As a result, the communication unit 5 may send a control signal, which instructs the start of driving the imaging unit 12, to the capsule endoscope 1.

The input unit 6 is constructed with a keyboard, mouse and the like, and is manually operated by the examiner to input various types of information to the control unit 9. Various instruction information applied for instruction to the control unit 9 or patient information about the subject 100 are input from the input unit 6. Examples of the instruction information are instruction information for instructing the display unit 7 to display the image acquired from the capsule endoscope 1, and instruction information for instructing the related system component to process the image acquired from the capsule endoscope 1. Examples of the patient information are information for specifying the subject 100, such as the name of the subject 100 (patient name), gender, date of patient's birth, and ID of the patient, and body attributes information, such as height, weight, and waist.

The display unit 7 may be a display unit such as a CRT display unit or a liquid crystal display unit, and displays various types of information instructed by the control unit 9. The display unit 7 displays images picked up by the capsule endoscope 1 and various types of information which are necessary for observing the insides of the subject 100 and to diagnose the subject such as patient information of the subject 100. The display unit 7 displays images that the control unit 9 processed in a predetermined manner.

The storage unit 8 stores various types of information that is instructed for writing by the control unit 9. Specifically, the storage unit 8 stores various types of information that are received from the capsule endoscope 1, input from the input unit 6, and image information underwent a predetermined process by the control unit 9. The storage unit 8 stores the image information in association with the motion information. The storage unit 8 sends information instructed for readout by the control unit 9 to the control unit 9.

The control unit 9 controls the driving and operations of the related components of the workstation 4, such as the communication unit 5, the input unit 6, the display unit 7, and the storage unit 8. Further, the control unit 9 controls the inputting and outputting operations to and from those components, and carries out an information process for inputting and outputting operations to and from those components. The control unit 9 outputs various control signals to the capsule endoscope 1 to the communication unit 5 on the basis of the instruction information input from the input unit 6. The control signal to the capsule endoscope 1 is sent to the capsule endoscope 1 by way of the antenna 5a. The workstation 4 functions as a control unit for controlling the driving of the capsule endoscope 1.

The control unit 9 includes a display control unit 9a for controlling operations for displaying various information by the display unit 7, and a communication control unit 9b for controlling the driving of the communication unit 5. The control unit 9 further includes a magnet selecting unit 9c for selecting a permanent magnet capable of generating a magnetic field high enough to move the capsule endoscope 1 in the liquid Lq1, and an image processing unit 9d for generating an image of the insides of the subject 100 on the basis of the image signal received from the capsule endoscope 1. Furthermore, the control unit 9 includes an image combining unit 9e for composing the common parts of a plurality of images generated by the image processing unit 9d to combine a plurality of images inside the subject 100, a position/posture detecting unit 9f for detecting a position and a posture of the capsule endoscope 1, and a status determining unit 9g for judging whether or not a status has been set up in which a motion of the capsule endoscope 1 can be controlled by a magnetic field generated by the permanent magnet 3.

The magnet selecting unit 9c selects a permanent magnet capable of generating a magnetic field high enough to move the capsule endoscope 1 in the liquid Lq1, on the basis of the judging result by the status determining unit 9g. Specifically, the status determining unit 9g detects a magnetic intensity field, which is generated by the permanent magnet 3 and applied to the capsule endoscope 1, on the basis of a magnetic-field detection signal received from the capsule endoscope 1, and compares the detected magnetic intensity with a predetermined range of magnetic intensity values. The status determining unit 9g judges whether or not a status has been set up in which a motion of the capsule endoscope 1 can be controlled by a magnetic field generated by the permanent magnet 3, on the basis of the comparison result. When the detected magnetic intensity is within the magnetic intensity range, the status determining unit 9g judges that the magnetic intensity by the permanent magnet 3 is high enough to control the motion of the capsule endoscope 1. When the detected magnetic intensity is below the magnetic intensity range, the status determining unit 9g judges that the magnetic intensity of the permanent magnet 3 is insufficient. When the detected magnetic intensity is above the magnetic intensity range, the status determining unit 9g judges that the magnetic intensity of the permanent magnet 3 is excessive. The magnet selecting unit 9c selects a permanent magnet, which is judged that the magnetic intensity of that permanent magnet is sufficient, by the status determining unit 9g. When the status determining unit 9g judges that the magnetic intensity of the permanent magnet is insufficient, the magnet selecting unit 9c selects a permanent magnet which develops a magnetic field stronger than by the current permanent magnet. When the magnetic intensity of the current permanent magnet is excessive, the magnet selecting unit 9c selects a permanent magnet which develops a magnetic field weaker than by the current permanent magnet. The display control unit 9a causes the display unit 7 to display the selection result of the permanent magnet by the magnet selecting unit 9c. The examiner views the permanent magnet selection result displayed by the display unit 7, and easily selects a permanent magnet suitable for the controlling a motion of the capsule endoscope 1 from those of the plurality of the permanent magnets.

The image processing unit 9d generates images picked up by the capsule endoscope 1 on the basis of image signals received from the capsule endoscope 1. The control unit 9 displays the images generated by the image processing unit 9d in a time sequential manner on the display unit 7. The image combining unit 9e carries out an image combining process for combining the images generated by the image processing unit 9d into a single image. The display control unit 9a causes the display unit 7 to display the processed image (panorama image representing the inner part of the digestive tract of the subject 100, for example) combined together by the image combining unit 9c. The image combining process performed by the image combining unit 9e will be described later.

The position/posture detecting unit 9f detects a position and posture of the capsule endoscope 1 in the spatial coordinate system xyz on the basis of motion information received by the capsule endoscope 1. To be more specific, the position/posture detecting unit 9f first sets up a spatial coordinate system xyz for determining a position and a posture of the capsule endoscope 1. The capsule endoscope 1 is set at the origin O in the spatial coordinate system xyz such that the diameter axis C2b, the major axis C1 and the diameter axis C2b are respectively placed on the x-axis, the y-axis and the z-axis of the spatial coordinate system xyz. The position/posture detecting unit 9f knows the position and the posture of the capsule endoscope 1, which is placed in the spatial coordinate system xyz, as an initial state. Subsequently, the position/posture detecting unit 9f successively detects the position coordinates (x, y, z) of the capsule endoscope 1 which moves or swings from the origin O (viz., successively changes from the initial state), and the direction of the major axis C1. The position/posture detecting unit 9f successively acquires a movement quantity (vector quantity) of the casing 10, a rotation angle of the major axis C1, and a rotation angle of the diameter axis C2a when the capsule endoscope 1 moves or swings in the spatial coordinate system xyz on the basis of motion information that is successively received from the capsule endoscope 1.

The position/posture detecting unit 9f detects a relative position of the casing 10 to the origin O, viz., the position coordinates (x, y, z) of the casing 10 in the spatial coordinate system xyz, and a vector direction of the major axis C1 in the spatial coordinate system xyz on the basis of the movement quantity of the casing 10, the rotation angle of the major axis C1 and the rotation angle of the diameter axis C2a thus successively obtained. The position coordinates (x, y, z) of the casing 10 and the vector direction of the major axis C1, which are detected by the position/posture detecting unit 9f, correspond to the position and posture of the capsule endoscope 1 in the spatial coordinate system xyz.

The position/posture detecting unit 9f detects an inclination of the diameter axis C2a with respect to the z-axis of the spatial coordinate system xyz on the basis of the rotation angle of the diameter axis C2a. The diameter axis C2a is an axis vector for determining the upward direction of the light receiving surface of the imaging unit 12, and determines the upward direction of the image picked up by the imaging unit 12. Accordingly, the position/posture detecting unit 9f detects an inclination of the image with respect to the z-axis (i.e., the image picked up by the imaging unit 12) of which the normal line vector is the major axis C1, by detecting the inclination of the diameter axis C2a with respect to the z-axis.

The control unit 9 stores the position and the posture of the capsule endoscope 1 detected by the position/posture detecting unit 9f, and the inclination of the image picked up by the imaging unit 12 with respect to the z-axis, as position/posture information, into the storage unit 8. The control unit 9 acquired position/posture information for each image information received from the capsule endoscope 1, and sequentially stores the position/posture information in association with the image information.

Figure 6:
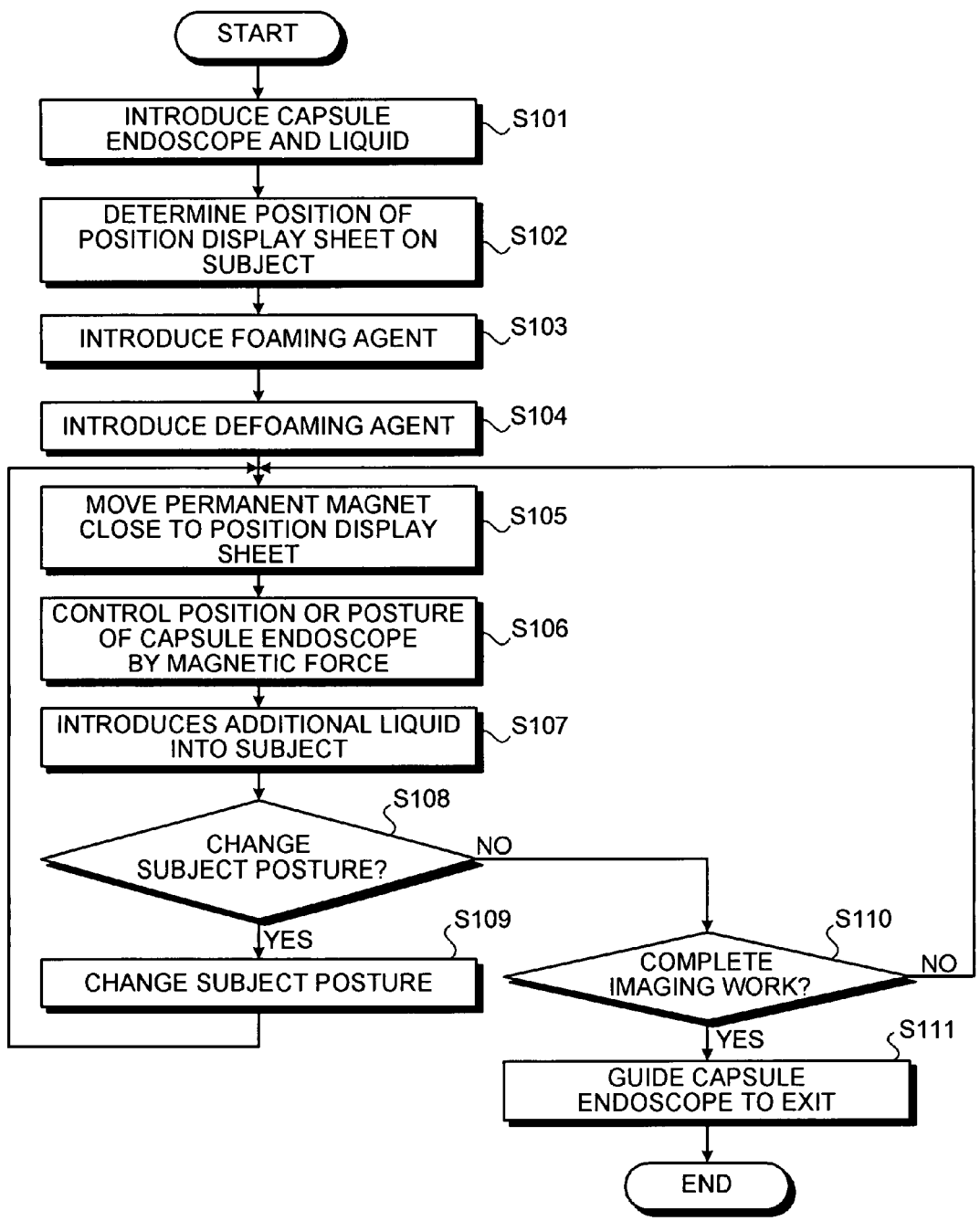
FIG. 6 is a flow chart showing procedural steps of observing the insides of the digestive tract of the subject by using the body-insertable device system.

An observing process for observing the insides of the digestive tract (e.g., stomach) of the subject 100 by using the images picked up by the capsule endoscope 1 will be described. FIG. 6 is a flow chart showing procedural steps of observing the insides of the digestive tract of the subject 100 by using the images picked up by the capsule endoscope 1 introduced into the subject 100.

In FIG. 6, to start with, the examiner starts an imaging operation of the capsule endoscope 1 by use of the workstation 4 or a given starter, introduces a capsule endoscope 1 into the subject 100, and introduces liquid Lq1 into the insides of the subject 100 by use of the liquid supply device Lp (step 101). The examiner wears the position display sheet 2 on the subject 100 and determines a position of the position display sheet 2 on the subject 100 (step S102). Specifically, to observe the insides of the stomach of the subject 100, as illustrated in FIG. 4, the position display sheet 2 is wound around the trunk of the subject 100 so as to cover an area part of the body surface near the stomach of the subject 100 to thereby determine a positional relation of the subject 100 to the position display sheet 2. If necessary, the capsule endoscope 1 and the liquid Lq1 may be introduced into the subject 100 who has the position display sheet 2.

The capsule endoscope 1 and the liquid Lq1 to be introduced into the subject 100 is swallowed from the mouth of the subject 100, for example, and then moves to reach a desired digestive tract to be observed in the subject 100. The examiner drives the workstation 4 to display the images picked up by the capsule endoscope 1 on the display, and visually examines the images and recognizes a state of the region (e.g., stomach) which the capsule endoscope 1 has reached in the subject 100. If required, it is allowed that the examiner introduces the capsule endoscope 1 into the subject 100, and then operates the workstation 4 to start the imaging operation of the capsule endoscope 1.

The examiner introduces a foaming agent as well as a proper amount of water into the subject 100 (step S103) to expand the desired digestive tract into which the capsule endoscope 1 has been introduced. As a result, the capsule endoscope 1 easily catches the digestive tract as the observation region within the imaging field and easily picks up images in the digestive tract. After securing the imaging field of the capsule endoscope 1 in the digestive tract, the examiner introduces a defoaming agent into the digestive tract in the subject 100 into which the foaming agent has been introduced (step S104), whereby bubbles generated on the surface of the liquid Lq1 are removed by the introduced foaming agent. As a result, the capsule endoscope 1 picks up images in the digestive tract without intercepting the imaging field by the bubbles generated by the foaming agent.

Subsequently, the examiner moves the permanent magnet 3 close to the position display sheet 2 worn by the subject 100 in which the capsule endoscope 1 has been introduced (step S105), to thereby generate a magnetic field for application to the capsule endoscope 1 in the subject 100. Specifically, the examiner moves the permanent magnet 3 close to the approaching position indicated by the marker of the position display sheet 2. In this case, the permanent magnet 3 is located close to an area part of the body surface of the subject 100, which is near the digestive tract into which the capsule endoscope 1 has been introduced, and the permanent magnet 3 can apply magnetic field to the capsule endoscope in the digestive tract.

The permanent magnet 3 for generating a magnetic field to the capsule endoscope 1 may consist of a single permanent magnet having a given magnetic force. However, it is desirable that it consists of plurality of permanent magnets of which the magnetic forces are different from one another, and one of those permanent magnets is selected in use. In this case, the examiner selects the permanent magnet 3 to be brought close to the approaching position by referring to the select information (e.g., magnet number) of the permanent magnet as well as the approaching position, which is presented by the position display sheet 2. Following this, the examiner refers to the permanent-magnet select result displayed by the workstation 4, and re-selects the permanent magnet 3 on the displayed select result, and adjust an intensity of the magnetic field applied to the capsule endoscope 1. In this way, the examiner can select the permanent magnet which is capable of generating a magnetic field having a proper magnetic intensity, for application to the capsule endoscope 1. The magnetic intensity of the magnetic field applied to the capsule endoscope 1 may be adjusted, for example, in a manner that the examiner adjusts a distance between the permanent magnet 3 and the position display sheet 2.

When the permanent magnet 3 is moved close to the approaching position presented by the position display sheet 2, the examiner operates the permanent magnet 3 to adjust the intensity and the direction of the magnetic field applied to the capsule endoscope 1 and to control at least one of the position and the posture of the capsule endoscope 1 by the magnetic force of the permanent magnet 3 (step S106). In this case, the examiner swings the permanent magnet 3 about the center of the desired marker (i.e., desired approaching position) of the position display sheet 2, for example, or moves the permanent magnet 3 to all the markers of the position display sheet 2. The permanent magnet 11 of the capsule endoscope 1 which has been applied with the magnetic field of the permanent magnet 3 reacts with the magnetic force of the permanent magnet 3 to move the casing 10. Under the action of the permanent magnet 11, the capsule endoscope 1 horizontally, for example, moves in the liquid Lq1 or swings to change at least one of the position as the observation region and the posture of the capsule endoscope in the digestive tract. In this way, the capsule endoscope 1 successively picks up images of the insides of the digestive tract while changing the direction of the imaging field to the insides of the digestive tract with movement of the casing 10.

Further, the examiner additionally introduces the liquid Lq1 into the subject 100 (step S107) to increase the amount of the liquid Lq1 in the digestive tract as the observation region. The capsule endoscope 1, as described above, has a specific gravity, which is almost equal to or smaller than that of the liquid Lq1, and has the center of gravity located closer to the rear end of the casing 10. The capsule endoscope 1 floats to the surface of the liquid Lq1 in a state that the imaging field is directed in the substantially vertical upward direction, and moves in the vertical upward direction as the liquid Lq1 in the digestive tract increases (viz., the water line rises). In this case, the capsule endoscope 1 picks up images at a position where the capsule endoscope 1 is closer to the insides of the digestive tract as the observation region.

When the examiner does not change the posture of the subject 100 to another posture and keeps the current posture (step S108, No), and continues the operation of picking up the images of the insides of the digestive tract as the observation region (step S110, No), the examiner repeats a sequence of procedural steps subsequent to the step S105. In this case, the examiner adjusts the amount of the liquid Lq1 in the digestive tract while referring to the images in the digestive tract, which are displayed on the display of the workstation 4, to thereby control the position of the capsule endoscope 1 in the digestive tract as viewed in the vertical direction to a desired position.

When the examiner changes the posture of the subject 100 to another posture and keeps the current posture and continues the operation of picking up the images of the insides of the digestive tract as the observation region (step S108, Yes), he/she changes the current posture (e.g., supine position) of the subject 100 to a desired posture (e.g., right side supine position) (step S109). The examiner repeats a sequence of the procedural steps subsequent to the step S105.

Thus, at least one of the position and the posture of the capsule endoscope 1 in the insides of the digestive tract as the observation region is controlled in such a way that the permanent magnet 3 is moved close to the approaching position presented by the position display sheet 2 and the motion of the capsule endoscope 1 is magnetically operated. As a result, the capsule endoscope 1 picks up a series of images over the substantially entire region of the insides of the digestive tract. The examiner displays a series of images picked up by the capsule endoscope 1 on the display of the workstation 4 to observe inside out the insides of the digestive tract as a desired observation region in the subject 100.

Then, when the examiner completes the work of observing the insides of the digestive tract as the observation region and completes the work of picking up the images of the insides of the digestive tract (step S110, Yes), he/she guides the capsule endoscope 1 to the exit of the digestive tract (step S111). The capsule endoscope 1 moves to the exit by the peristaltic motion of the digestive tract or the flow of the liquid Lq1, or it moves to the exit of the digestive tract by the magnetic force of the permanent magnet 3 located close to the body surface of the subject 100, and then moves to another digestive tract. Here, the capsule endoscope 1 completes the operation of picking up images in the digestive tract as the current observation region. Subsequently, the capsule endoscope 1 moves in the subject 100 by the peristaltic motion of the digestive tract, the flow of the liquid Lq1 or the magnetic force by the permanent magnet 3, while picking up images in the digestive tracts, and finally is discharged outside the subject 100.

At this time, the examiner may display the images picked up by the capsule endoscope 1 on the display of the workstation 4 and observe the insides of the digestive tracts of the subject 100. The examiner may also operate the workstation 4 to send a control signal for stopping the imaging operation to the capsule endoscope 1 having completed the operation of picking up images of the desired observation region to thereby stop its imaging operation.

The foaming agent in the step S103 and the defoaming agent in the step S104 may be introduced into the subject 100 whenever the need arises. In case where the examiner observes the images in the subject 100, which are displayed by the workstation 4, and judges that the insides of the digestive tract should be carefully observed, the foaming agent and the defoaming agent may be successively introduced into the subject 100.

Figure 7:
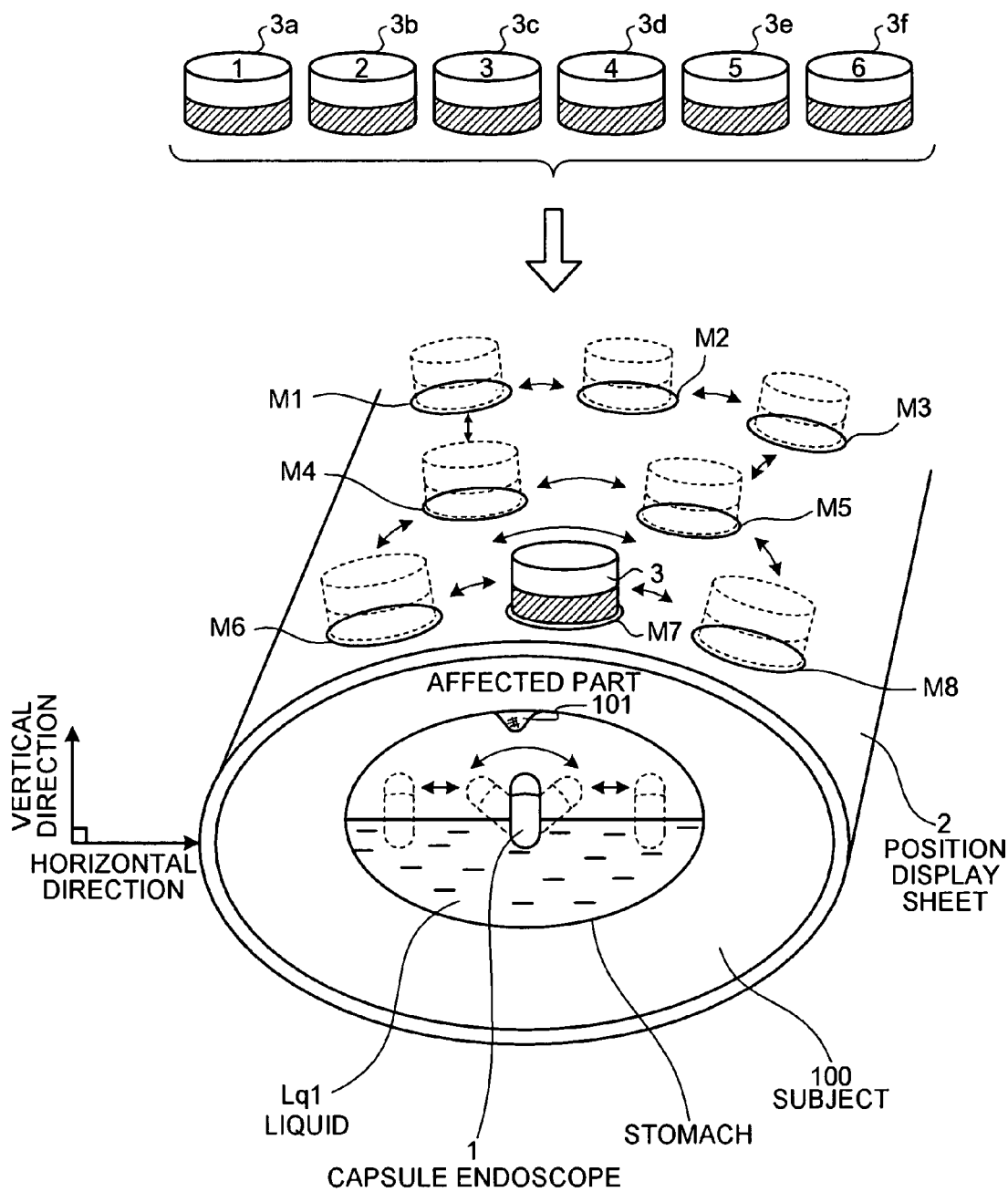
FIG. 7 is a schematic diagram useful in explaining operations of the permanent magnet that controls at least one of the position and the posture of the capsule endoscope introduced into the subject.

Operation to control at least one of the position and the posture of the capsule endoscope 1 will be described in detail. A case used for the description is that the examiner introduces the capsule endoscope 1 into the stomach of the subject 100 to observe the stomach as an observation region. FIG. 7 is a schematic diagram explaining operations of the permanent magnet 3 that controls at least one of the position and the posture of the capsule endoscope 1 introduced into the subject 100.

The capsule endoscope 1 and the liquid Lq1 which were swallowed from the mouth of the subject 100, passes through the gullet, and as illustrated in FIG. 7, reaches the stomach as an observation region. The capsule endoscope 1, as described above, has a specific gravity, which is almost equal to or smaller than that of the liquid Lq1, and has the center of gravity located closer to the rear end of the casing. Accordingly, the capsule endoscope 1 in the liquid Lq1, as shown in FIG. 7, floats to the surface of the liquid Lq1 in a state that the imaging field is directed in the substantially vertical upward direction.

The subject 100 wears the position display sheet 2 so that the position display sheet 2 is positioned near the stomach as the observation region. The position display sheet 2 shows the examiner an approaching position on the body surface of the subject 100 by using a plurality of markers. The examiner selects the permanent magnet 3 to be brought close to the approaching position of the subject 100 from the six permanent magnets 3a to 3f generating magnetic forces, which are different from one another on the basis of the select information (e.g., magnetic number) of the permanent magnet presented by the position display sheet 2 or the permanent-magnet selection result displayed by the workstation 4. The examiner operates and moves the thus selected permanent magnet 3 to the plurality of markers on the position display sheet 2. Specifically, when the subject 100 is in a supine position, for example, the examiner moves the permanent magnet 3 close to all the markers M1 to M18 of the supine-position marker group MG1. The examiner swings the permanent magnet 3 about the desired marker (e.g., marker M3). Then, the examiner repeats the operation of the permanent magnet 3 as required.

The permanent magnet 3 that is operated in this way by the examiner magnetically catches the capsule endoscope 1 by applying a magnetic field to the capsule endoscope 1 in the liquid Lq1 in the stomach, and changes the position and the direction of the magnetic field to the capsule endoscope 1 to control the motion of the capsule endoscope 1. The capsule endoscope 1 moves or swings in the liquid Lq1, while following the motion of the permanent magnet 3, to change at least one of the position and the posture of the capsule endoscope in the stomach. Thus, the permanent magnet 3 changes at least one of the position and the posture of the capsule endoscope 1 in the liquid Lq1 by the magnetic force. The capsule endoscope 1 that is moved by the permanent magnet 3 successively picks up images of the insides of the stomach while changing the position or the posture of the imaging field in the stomach.

Then, the examiner decreases or increases the amount of the liquid Lq1 in the stomach when need arises or changes the posture of the subject 100 to another posture such as the left side supine position or the right side supine position. And, the examiner brings the permanent magnet 3 close to the left side supine-position marker group MG2 or the right side supine-position marker group MG3 according to the posture of the subject 100. In this case, the examiner operates the permanent magnet 3 as in the case of the supine-position marker group MG1 already stated. The permanent magnet 3 thus operated changes at least one of the position and the posture of the capsule endoscope 1 as in the case of the subject 100 who is in the supine position.

Thus, the permanent magnet 3 controls at least one of the position and the posture of the capsule endoscope 1 by its magnetic force, so that the capsule endoscope 1 exhaustively picks up images of the stomach wall located above the liquid Lq1 as Viewed in the vertical direction, that is, the stomach wall part expanded by the forming agent mentioned above. Thus, the capsule endoscope 1 surely picks up a series of images over the entire stomach wall, for example, an affected part 101 of the stomach wall. The same thing is true for the case of decreasing or increasing the amount of the liquid Lq1 that floats the capsule endoscope 1. The capsule endoscope 1 displaces in the vertical direction as the water line of the liquid Lq1 changes, and moves close to the stomach wall to pick up an enlarged image of the stomach wall. In this case, the capsule endoscope 1 may approach the affected part 101 and may pick up an enlarged image of the affected part 101.

The capsule endoscope 1 floating to the surface of the liquid Lq1 may be arranged such that its gravity center is located at the central part or thereabround of the casing 10 or close to the rear end thereof, and its imaging field is directed upward from the liquid Lq1 as viewed in the vertical direction by the magnetic force applied from the permanent magnet 3. However, it is preferable that the gravity center of the capsule endoscope is located closer to the rear end of the casing 10. In this case, the imaging field of the capsule endoscope 1 is direction upward as viewed in the vertical direction by the floating force of the liquid Lq1. This fact indicates that the motion of the capsule endoscope 1 is controlled by using the permanent magnet having weak magnetic force, and the permanent magnet 3 used for controlling the motion of the capsule endoscope 1 is reduced in size.

The capsule endoscope 1 having finished the operation of picking up the images of the insides of the stomach as the desired observation region then moves to the next digestive tract (e.g., duodenum) in accordance with the step S111 stated above. Specifically, the capsule endoscope 1 moves from the stomach close to the pylorus by the magnetic force applied from the permanent magnet 3 located close to the pylorus of the subject 100. In this case, the examiner changes the posture of the subject 100 to the right side supine position, and then moves the permanent magnet 3 to a part of the body surface of the subject 100, which is close to the pylorus, thereby to guide the capsule endoscope 1 to the pylorus by the magnetic force applied from the permanent magnet 3. The capsule endoscope 1 may be guided by the liquid Lq1 flowing from the stomach to the duodenum.

Figure 8:
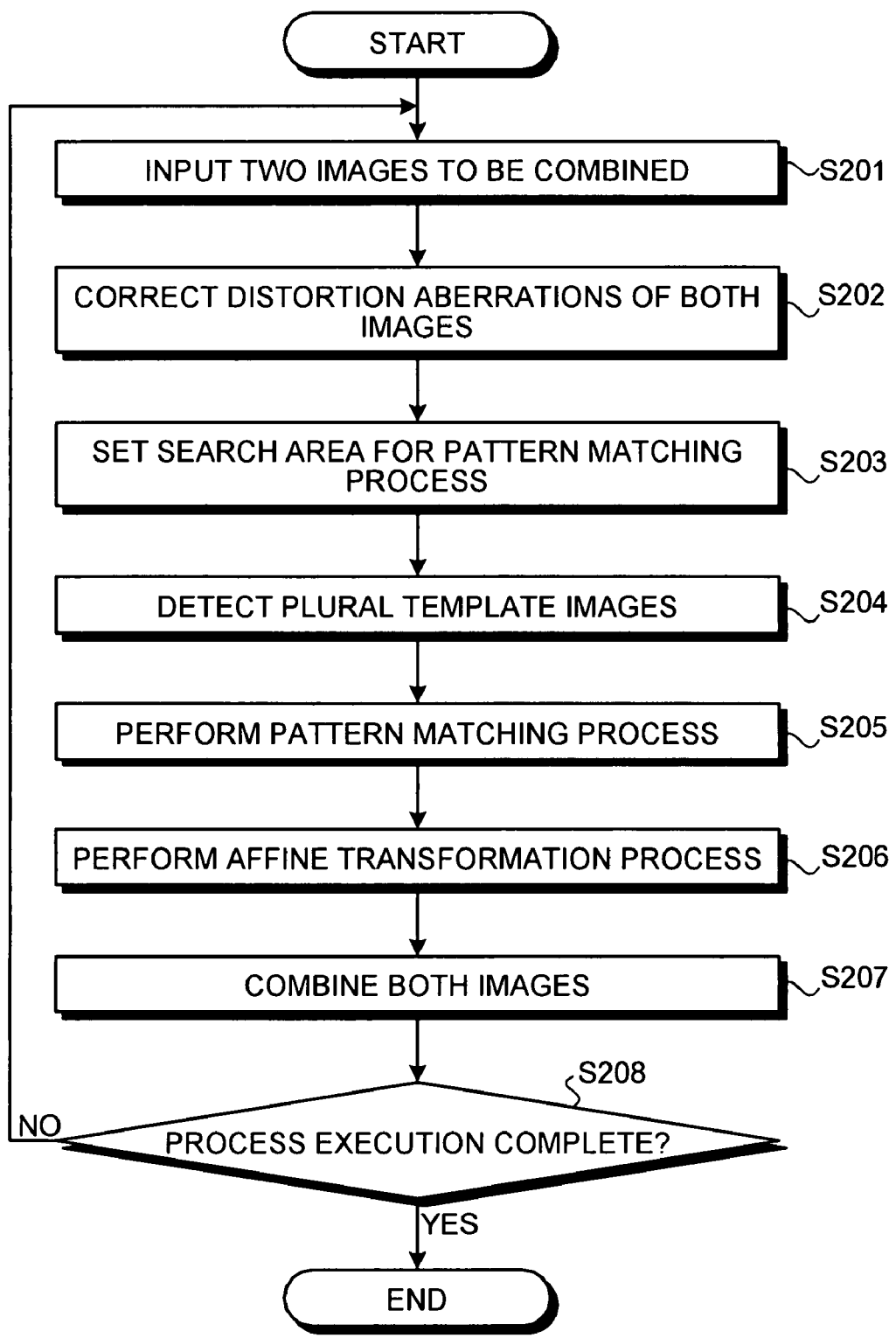
FIG. 8 is a flow chart showing procedural steps of an image combining process performed by a control unit of the workstation.
Figure 9:
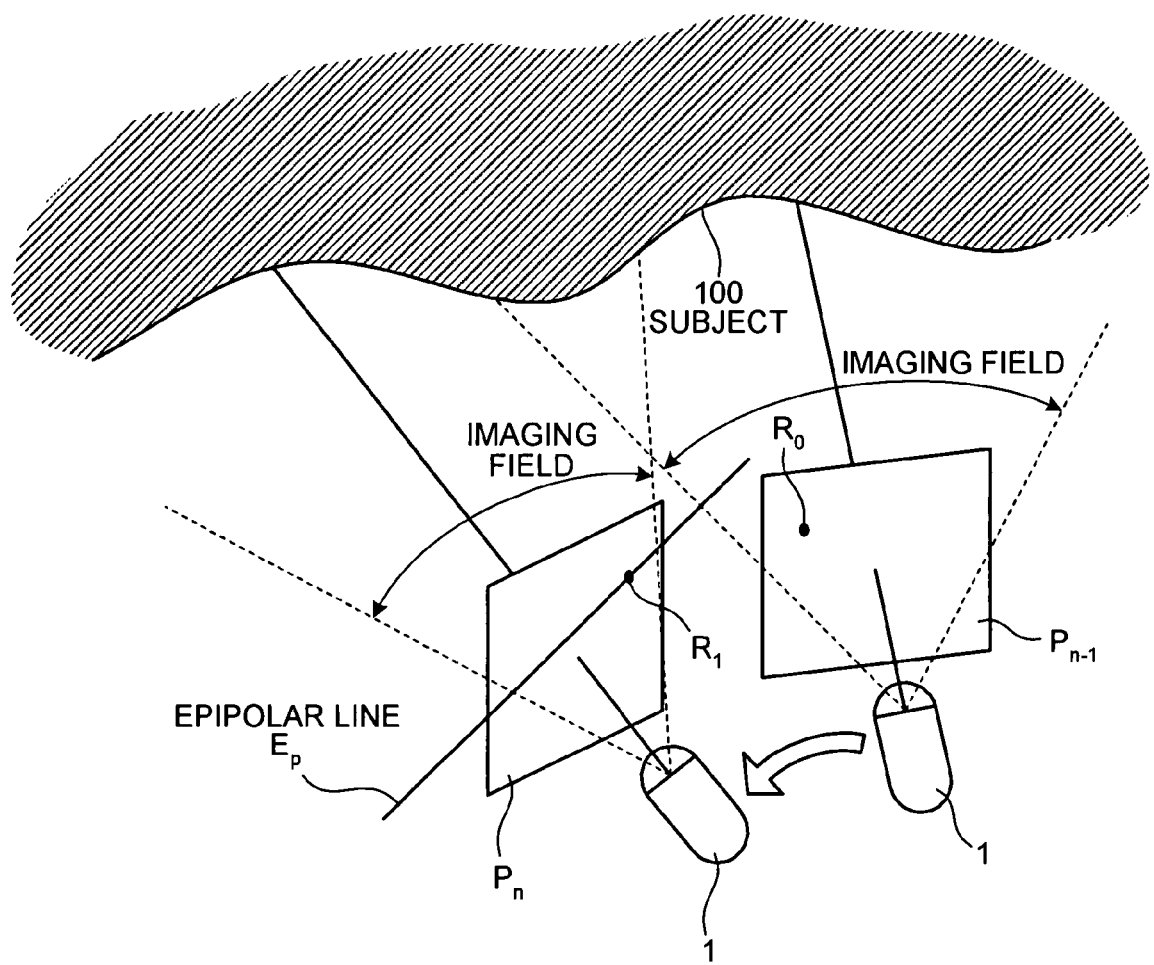
FIG. 9 is a schematic diagram useful in explaining operations of the control unit for combining a plurality of images.

An image combining process for combining a plurality of images of the insides of the subject 100, which have been picked up by the capsule endoscope 1, will be described in detail. FIG. 8 is a flow chart showing procedural steps of the image combining process performed by the control unit 9 of the workstation 4. FIG. 9 is a schematic diagram explaining operations of the control unit 9 for combining a plurality of images.

The control unit 9 of the workstation 4 knows relative positions and relative directions of a plurality of images picked up by the capsule endoscope 1 on the basis of plural pieces of image information acquired from the capsule endoscope 1 and the position/posture information associated with those pieces of image information, and combines the plurality of images by using the epipolar geometry. In FIG. 8, the control unit 9 first inputs two images to be combined (step S201). The input unit 6 inputs information designating the two images to be combined to the control unit 9 according to the inputting operation by the examiner. The control unit 9 reads out the two images to be combined $P_n$ and $P_{n-1}$ from the storage unit 8 according to the input information from the input unit 6. At the same time, the control unit 9 reads out the position/posture information associated with the images $P_n$ and $P_{n-1}$ from the storage unit 8. The image combining unit 9e knows the position and the posture of the capsule endoscope 1 and an inclination of the image with respect to the z-axis when the images $P_n$ and $P_{n-1}$ are picked up on the basis of the position/posture information of the images $P_n$ and $P_{n-1}$.

The control unit 9 corrects distortion aberrations of the two images $P_n$ and $P_{n-1}$ that are read out (step S202) In this case, the image combining unit 9e corrects the distortion aberrations of the two images $P_n$ and $P_{n-1}$. As a result, when an object, which is contained in both the images $P_n$ and $P_{n-1}$, is picked up, the image combining unit 9e merges the pixel areas representing the object (high similarity) to combine the images $P_n$ and $P_{n-1}$.

The control unit 9 then sets a search area for a pattern matching process to search for the pixel area where a similarity between those images $P_n$ and $P_{n-1}$ is high (step S203). To this end, the image combining unit 9e calculates a plurality of reference points on the image $P_{n-1}$ and a plurality of epipolar lines on the image $P_n$, which correspond to the reference points according to the epipolar geometry.

The images $P_n$ and $P_{n-1}$ are those images picked up before and after the capsule endoscope 1 changes at least one of the position and the posture of the capsule endoscope. The image $P_{n-1}$, as shown in FIG. 9, is the image of the insides of the subject 100 picked up by the capsule endoscope 1, and the image $P_n$ is the image of the insides of the subject 100 after the capsule endoscope 1 changes the position and the posture of the endoscope itself. When the images $P_n$ and $P_{n-1}$ contain the same object, those images include pixel areas of high similarity. The image combining unit 9e sets a plurality of reference points (more than six points, for example) corresponding to the pixel areas having high similarity on the image $P_{n-1}$, and sets a plurality of epipolar lines corresponding to those reference points on the image $P_n$.

For example, the image combining unit 9e, as shown in FIG. 9, sets a reference point $R_0$ on the image $P_{n-1}$, and sets an epipolar line $E_p$ corresponding to the reference point $R_0$ on the image $P_n$. Assuming that the reference point $R_0$ indicates position coordinates of a pixel area having a high similarity between the images $P_n$ and $P_{n-1}$, the image combining unit 9e may set an epipolar line $E_p$ on the image $P_n$, for example, between two opposed vertexes on the image $P_n$. The epipolar line $E_p$ contains a point $R_1$ corresponding to the reference point $R_0$. The corresponding point $R_1$ indicates the position coordinates of the pixel area of the image $P_n$ having a higher similarity than that of the pixel area of the image $P_{n-1}$ of which the position coordinates are set by the reference point $R_0$.

In this way, the image combining unit 9e sets a plurality of reference points (more than six points, for example) on the image $P_{n-1}$, and sets a plurality of epipolar lines corresponding to those reference points on the image $P_n$. In this case, the image combining unit 9e sets the pixel areas in the vicinity of those epipolar lines as a search area for the pattern matching process.

Then, the control unit 9 detects a plurality of pixel areas (template image), which will be the reference for the pattern matching process, on the basis of the image $P_{n-1}$ (step S204). In this case, the image combining unit 9e detects a plurality of template images (more than six points, for example) corresponding to a plurality of reference points as exemplified by the reference point $R_0$.

The control unit 9 performs a pattern matching process for detecting a plurality of pixel areas on the image $P_n$ which are higher in similarity than the template images thus detected (step S205). In this case, the image combining unit 9e selects, for example, the pixel area in the vicinity of the epipolar line $E_p$ on the image $P_n$ to be an search area for the pattern matching process, and detects the pixel area on the image $P_n$ which is higher in similarity than the template image corresponding to the reference point $R_0$. The image combining unit 9e calculates a corresponding point $R_1$ for determining the position coordinates of the pixel area having a high similarity on the image $P_n$. The image combining unit 9e repeats the pattern matching process for the plurality of template images and the epipolar lines, and detects six or more pixel areas on the image $P_n$, which correspond to six or more template images. And, the image combining unit 9e calculates six or more corresponding points on the image $P_n$, which respectively correspond to six or more coordinate points for determining the position coordinates of six or more pixel areas, viz., six or more reference points as exemplified by the reference point $R_0$.

When the image combining unit 9e calculates the reference points of six or more, for example, and the corresponding points, the control unit 9 performs an affine transformation process on the images $P_n$ and $P_{n-1}$ (step S206). In this case, the image combining unit 9e calculates affine parameters according to the method of least squares by using the calculated the reference points of six or more and the corresponding points. The image combining unit 9e transforms the coordinate system on the image $P_{n-1}$ into the coordinate system on the image $P_n$ by using the calculated affine parameters, and performs the affine transformation process on the images $P_n$ and $P_{n-1}$.

Subsequently, the control unit 9 merges the images $P_n$ and $P_{n-1}$ having undergone the affine transformation process (step S207) into one processed image (panorama image, for example). In this case, the image combining unit 9e merges the pixel area (i.e., pixel area having a high similarity) representative of an object, which is contained in both the images $P_n$ and $P_{n-1}$ having undergone the affine transformation process into a processed image.

When the image combining process is continued (step S208, No), the control unit 9 then repeats a sequence of the procedural steps subsequent to the step S201. In this case, the image combining unit 9e is able to successively combine a plurality of images picked up by the capsule endoscope 1 (e.g., a series of images over the substantially entire region of the inside of the stomach) and finally to generate a panorama image representing an observation region in the subject 100, for example, an image of the entire stomach wall. When receiving information instructing the end of the processing from the input unit 6, the control unit 9 ends the image combining process (step S208, Yes). In this case, the control unit 9 stores the image processed by the image combining process into the storage unit 8.

The control unit 9 is able to generate a cylindrical processed image stereographically representing the insides of the digestive tract of the subject 100 on the basis of the processed image generated by the image combining process, for example, a stripe-like panorama image. In this case, the image combining unit 9e transforms a rectangular coordinate system into a cylindrical coordinate system, and merges both end parts of the stripe-like panorama image as viewed in the longitudinal direction of the stripe-like panorama image into a cylindrical processed image. The control unit 9 stores such a cylindrical processed image into the storage unit 8.

Figure 10:
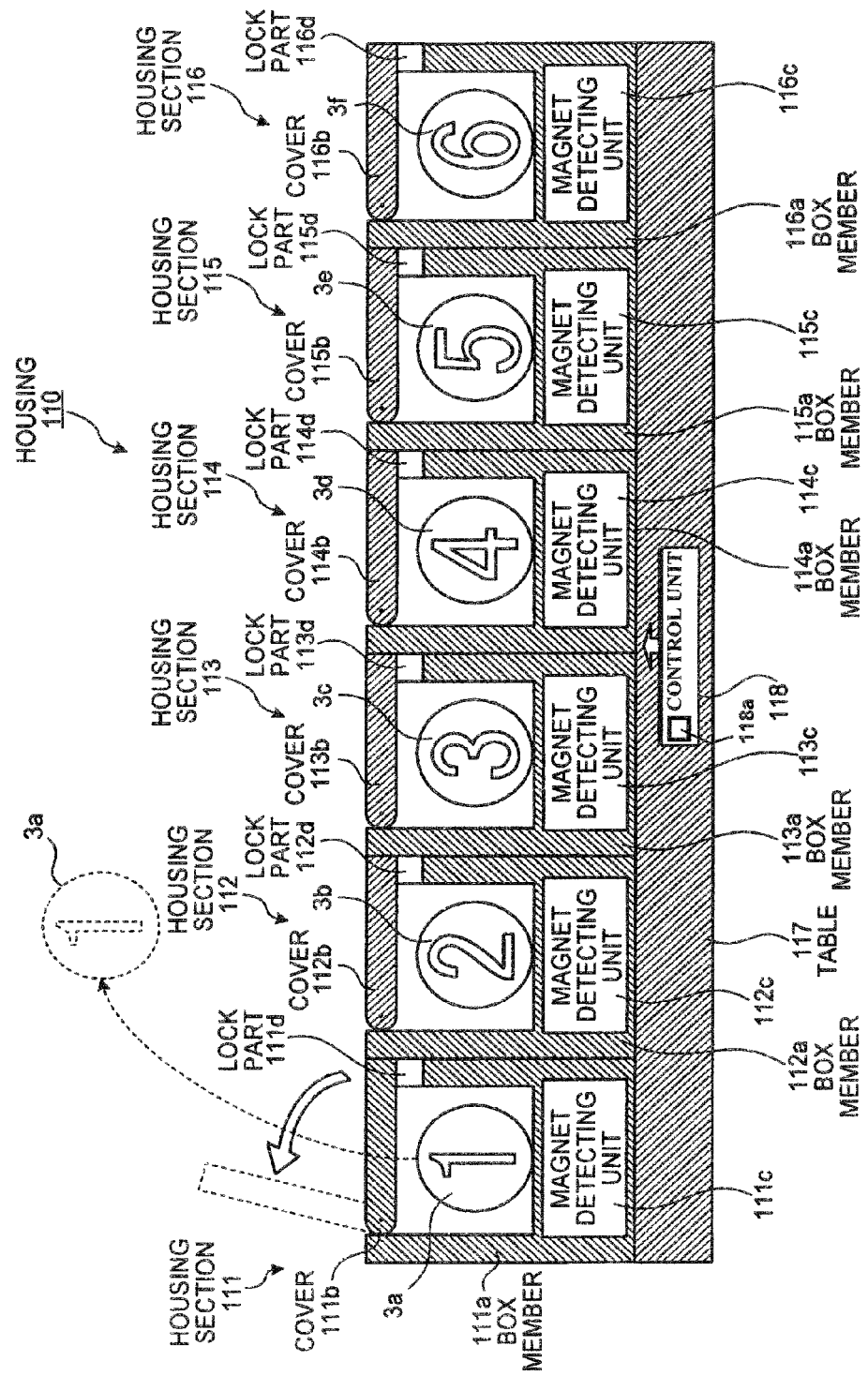
FIG. 10 is a schematic diagram showing a configuration example of a housing for housing a plurality of permanent magnets.

A housing for housing a plurality of permanent magnets provided for selecting the permanent magnet 3 to control the motion of the capsule endoscope 1 will next be described. FIG. 10 is a schematic diagram showing a configuration example of a housing for housing permanent magnets. A housing for housing six permanent magnets 3a to 3f prepared for selecting the permanent magnet 3 will be described by way of example. Two or more permanent magnets suffices for the invention, and the number of the housing does not limit the housing construction in any way.

As shown in FIG. 10, the housing 110 includes six housing sections 111 to 116 for housing the permanent magnets 3a to 3f, a table 117 for temporarily connecting the housing sections 111 to 116, and a control unit 118 for controlling the driving operations for opening and closing the housing sections 111 to 116. The permanent magnets 3a to 3f are respectively attached with magnet numbers 1 to 6 for specifying those permanent magnets. In this instance, the magnetic forces of the permanent magnets 3a to 3f increase as the magnet number increases. The housing section 111 is provided for housing the permanent magnet 3a having the magnet number 1. Specifically, the housing section 111 includes a box member 111a for housing the permanent magnet 3a, a cover 111b for closing and opening the opening of the box member 111a, a magnet detecting unit 111c for detecting the permanent magnet 3a held in the box member 111a, and a lock part 111d for locking the cover 111b. The box member 111a is a member incurved in cross section, and the cover 111b is provided near the opening thereof in a swingable way. A cover state detecting unit 111e, not shown, detects an open state and a close state of the cover 111b. The permanent magnet 3a placed in the box member 111a is put into and taken out of the box member by opening and closing the cover 111b. When the permanent magnet 3a is put in the box member 111a, the magnet detecting unit 111c detects the magnetic field or weight of the permanent magnet 3a and detects whether the permanent magnet 3a is present or not in the box member 111a, on the basis of the detection result. The magnet detecting unit 111c informs the control unit 118 of the result of detecting the permanent magnet 3a. The lock part 111d locks or unlocks the cover 111b under control of the control unit 118. Further, the cover state detecting unit 111e detects if the cover 111b is opened or closed, and sends the detection result to the control unit 118.

The housing sections 112 to 116 house the permanent magnets 3b to 3f of magnet numbers 2 to 6, respectively. The structural arrangement and function of the housing section 111 is correspondingly applied to those housing sections 112 to 116. The housing sections 112 to 116 respectively include box members 112a to 116a for housing the permanent magnets 3b to 3f, covers 112b to 116b for opening and closing the box members 112a to 116a, magnet detecting units 112c to 116c for detecting the permanent magnets 3b to 3f held in the box members 112a to 116a, lock part 112d to 116d for locking the covers 112b to 116b, and cover state detecting unit 112e to 116e (not shown) for detecting open/close state of the covers 112b to 116b. The box members 112a to 116a have the substantially same functions as those of the box member 111a of the housing section 111, and the covers 112b to 116b have also the substantially same functions as those of the cover 111b of the housing section 111. The magnet detecting units 112c to 116c have the substantially same functions as those of the magnet detecting unit 111c of the housing section 111; the lock parts 112d to 116d have the substantially same functions as those of the lock part 111d of the housing section 111; and cover state detecting units 112e to 116e have the substantially same functions as those of the cover state detecting unit 111e of the housing section 111. Additionally, the housing includes a permanent magnet select section 118a for selecting an open/close cover (permanent magnet to be taken out) according to select information (e.g., magnet number or intensity of generated magnetic field), presented together with the approaching position by the position display sheet 2.

The control unit 118, provided on the table 117, for example, controls the driving operations of the magnet detecting units 111c to 116c and the lock parts 111d to 116d. Specifically, the control unit 118 acquires the detection results on the permanent magnets 3a to 3f from the magnet detecting units 111c to 116c, the open/close state detection results on the covers 111b to 116b from the cover state detecting units 111e to 116e, and input information to the permanent magnet select section, and controls the driving operations of the lock parts 111d to 116d according to the acquired input information and detection results. When the control unit 118 receives the detection results that the permanent magnets are present from all the magnet detecting units 111c to 116c, the control unit controls the driving operation for locking to the lock parts 111d to 116d. When the control unit 118 receives the select result on the selection by the permanent magnet select section, the control unit 118 controls the driving operation for unlocking to the lock part (one of the lock parts 111d to 116d corresponding to the cover to be unlocked) for unlocking the cover of the selected permanent magnet (one of the covers 111b to 116b). At this time, other lock parts (corresponding to those ones other than the lock part to be unlocked) remain locked.

Then, the selected permanent magnet is taken out of the box member and the capsule endoscope 1 is guided into the subject 100 by using the permanent magnet taken out. When the control unit 118 acquires the detection result of the permanent magnet being not present from one of the magnet detecting units 111c to 116c, the control unit 118 keeps an unlocked state of the lock part (one of the lock parts 111d to 116d) of the housing section having the magnet detecting unit having informed of the detection result of the absence of permanent magnet, i.e., the housing section from which the permanent magnet was taken out. At the same time, the control unit 118 keeps a cover closed state of each of the lock parts (i.e., one of the lock parts 111d to 116d) of the housing sections having the remaining magnet detecting units having informed of the detection result of the presence of the permanent magnet, i.e., the housing sections housing the permanent magnets. The guiding operation of the capsule endoscope 1 ends, the taken out permanent magnet is returned to the housing section (one of the housing sections 111 to 116), and the magnet detecting unit associated with the housing section detects the presence of the permanent magnet. Further, the cover of the housing section is closed, and the cover state detecting units 111e to 116e detect that the covers 111b to 116b have been closed. When the control unit 118 is informed of those detection results, the control unit 118 controls the lock parts 111d to 116d of all the covers 111b to 116b for their locking. In this case, the covers of the housing sections may be manually closed or automatically closed according to the detection results of the magnet detecting units. The control unit 118, the magnet detecting units 111c to 116c, the lock parts 111d to 116d, and the cover state detecting units 111e to 116e may perform detection or control electrically or may perform detection or control with mechanical mechanism. Examples of the electrical detection are to detect the weight of the permanent magnet, to detect a magnetic field of the permanent magnet, and to attach RFID tags to the permanent magnets and readers, which read information from the RFID tags, to the magnet detecting units 111c to 116c. The housing 110 may be shielded so as to minimize leakage of the magnetic field. Ferromagnetic material is used for the shielding member. It is evident that means to prevent the permanent magnet from being taken out is not limited to the combination of the cover and the lock part. Such a means may be any means (confining unit) if it is capable of confining the permanent magnet within the housing section. An example of such is that a ferromagnetic member is located in the housing section, the permanent magnet is held down there by the utilization of the attraction force acting between the ferromagnetic member and the permanent magnet, and the attraction force for confining the permanent magnet is controlled by using a distance changing unit for changing a distance between the ferromagnetic member and the permanent magnet. The confining unit may be constructed such that an electromagnet is located in the housing section, and a confining state of the permanent magnet is controlled by changing the current applied to the electromagnet. The confining unit may also be a fixing part for mechanically fixing the permanent magnet to the inside of the housing section.

The control unit 118 performs such a control that one permanent magnet is selected from the permanent magnets 3a to 3f contained in the housing sections 111 to 116 and taken out of the housing section, while preventing a plurality of permanent magnets from being simultaneously taken out. For example, as shown in FIG. 10, when the examiner takes out the permanent magnet 3a among the permanent magnets 3a to 3f, the control unit 118 acquires the detection result of absence of the permanent magnet from the magnet detecting unit 111c, while at the same time acquires the detection result of presence of the permanent magnet from the remaining magnet detecting units 112c to 116c. In this case, the control unit 118 instructs the lock part 111d to unlock the cover, and at the same time instructs the remaining ones 112d to 116d to lock the covers. As a result, the examiner is allowed to take out the necessary permanent magnet from the housing 110. It is prevented that a plurality of permanent magnets are accidentally brought close to the subject 100 having the capsule endoscope 1 introduced thereinto. A safety is secured in observing the insides of the subject 100.

Figure 11:
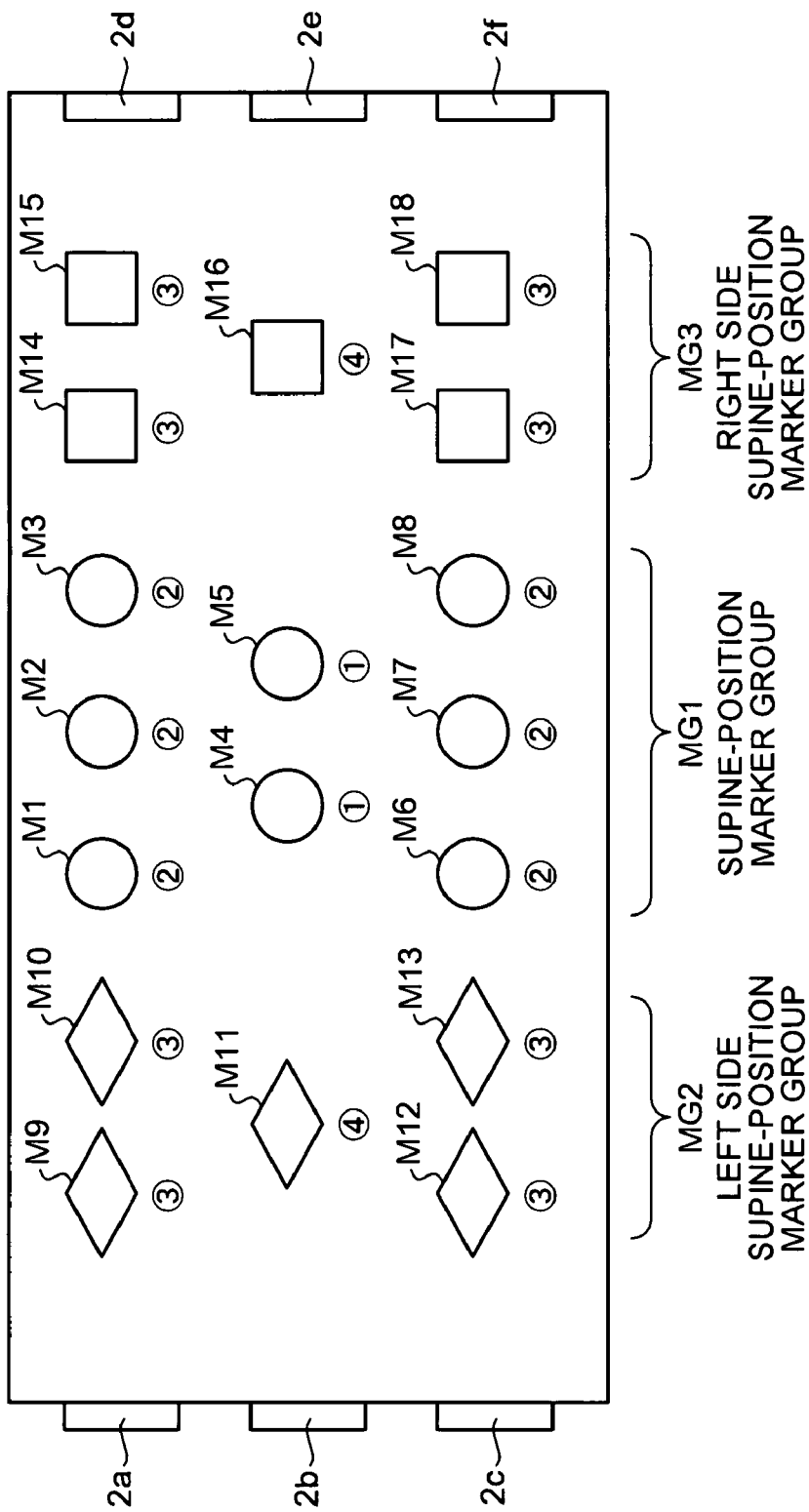
FIG. 11 is a schematic diagram showing a position display sheet in which a plurality of markers have shapes which are different for each posture of the subject.

In the position display sheet 2 in the first embodiment, one kind of shape such as a circle is used for the plurality of markers as the markers indicating an approaching position on the body surface of the subject 100. The plurality of markers formed on the position display sheet 2 may take different kinds of shapes that are respectively used in association with the postures of the subject 100. In this case, as shown in FIG. 11, the plurality of markers M1 to M18 are formed so that the supine-position marker group MG1, the left side supine-position marker group MG2 and the right side supine-position marker group MG3 are different from one another in shape.

Figure 12:
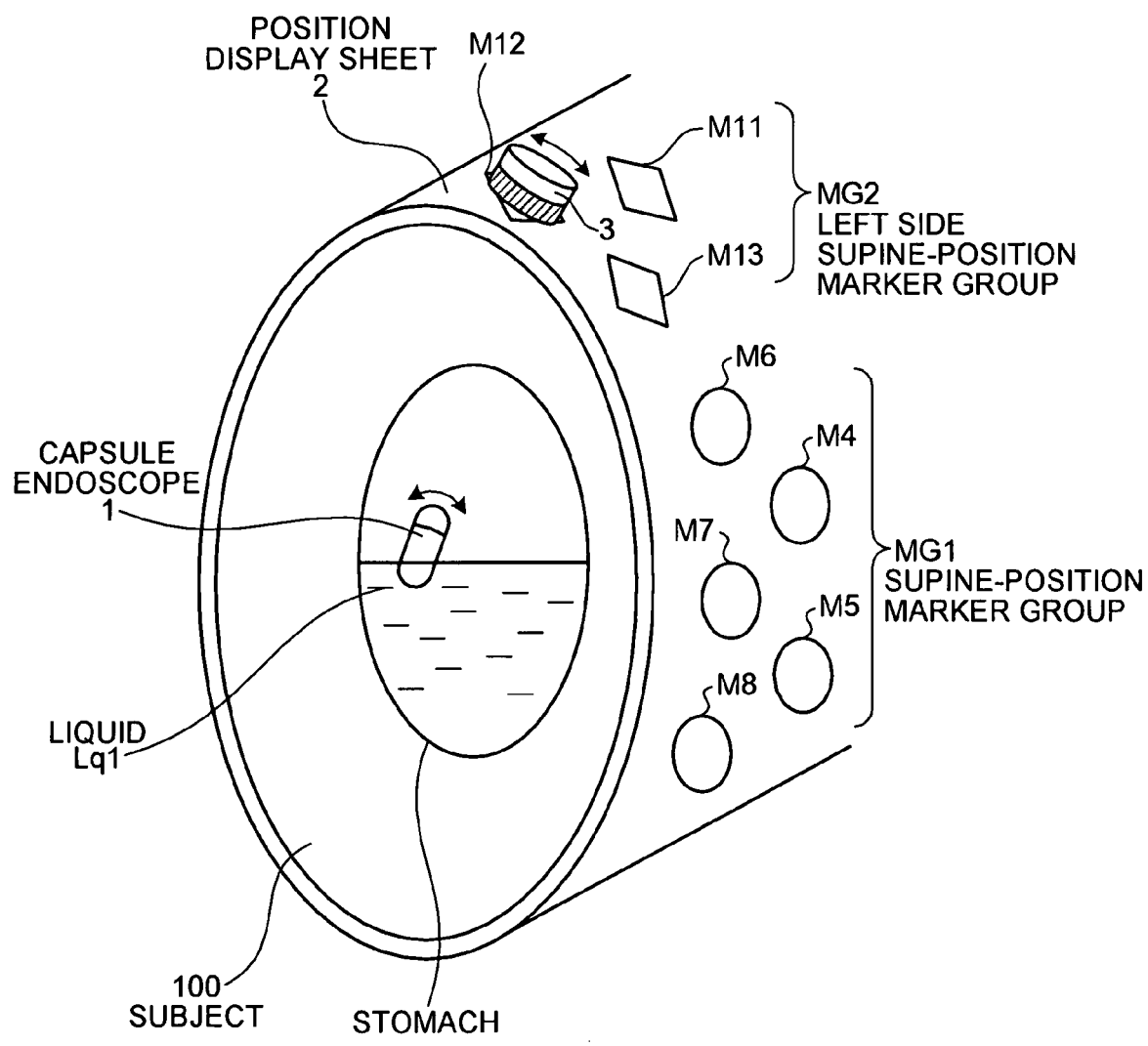
FIG. 12 is a schematic diagram showing the state in which the position display sheet presents an approaching position for each posture by using a plurality of markers of which the shapes are different from one another.

The position display sheet 2 on which the markers M1 to M18 having the different shapes different for each posture of the subject 100 is capable of clearly presenting the approaching positions for each posture of the subject 100. When the subject 100 postures in the left side supine position, for example, as shown in FIG. 12, the position display sheet 2 clearly shows the approaching position on the subject 100 who is in the left side supine position to which the permanent magnet 3 approaches, by the left side supine-position marker group MG2. Accordingly, the position display sheet 2 eliminates useless actions of the examiner. For example, it does not happen that the examiner uselessly moves the permanent magnet 3 to the approaching position to be presented to the examiner when the subject 100 takes another posture.

In the first embodiment, the plurality of markers indicating the approaching positions are formed on the position display sheet 2. In the invention, it is sufficed that at least one marker indicating the approaching position is formed on the position display sheet 2. The number of the makers is not limited to 18 in particular. The number of the markers may be reduced if the optical system of the imaging unit of the capsule endoscope is designed to have a wider angle, e.g., 100° to 140°, and the imaging field of the capsule endoscope is wider. For example where the position display sheet 2 having one marker is used, the imaging field of the capsule endoscope to be introduced into the digestive tract is set to be wide. In operation, the permanent magnet that is located close to the marker of the position display sheet 2 is swung near the marker, whereby the capsule endoscope picks up a series of images over the substantially entire region of the inside of the digestive tract.

As described above, in the first embodiment, the position display sheet for presenting a position on the body surface of the subject that permanent magnet approaches, i.e., an approaching position, is set to the subject, the permanent magnet is moved close to the approaching position presented by the position display sheet, at least one of the position and the posture of the capsule endoscope, which has been introduced into the digestive tract of the subject and is in the liquid, is changed by the magnetic force of the permanent magnet. The capsule endoscope picks up a series of images over the substantially entire region of the inside of the digestive tract without such troublesome examination work that the examiner carefully views the images of the inside of the digestive tract, which are picked by the capsule endoscope, on the display, and successively knows the imaging field of the capsule endoscope. The body-insertable device system is realized which readily reduces the time taken for the observation of the inside of a desired digestive tract.

By using the body-insertable device system, even the person engaged in medical works such as the nurse as well as the doctor may readily changes at least one of the position and the posture of the capsule endoscope as the observation region, and acquires a series of images over the substantially entire region of the inside of the digestive tract into the workstation. And, there is eliminated such an unwanted situation that the doctor is tied to the work of magnetically guiding the capsule endoscope in the digestive tract (viz., the operation of guiding the capsule endoscope) for a long time.

Further, at least one of the position and the posture of the capsule endoscope in the digestive tract is actively changed, so that the image of a desired region in the digestive tract is easily picked up by the capsule endoscope. The inside of the digestive tract are completely observed in a short time. Particularly even when a digestive tract having a relatively simple shape such as the stomach is observed, the useful effects mentioned above are remarkably produced.

Second Embodiment

A second embodiment of the present invention will be described. As recalled, in the first embodiment, at least one of the position and the posture of the capsule endoscope 1 in the liquid Lq1 is controlled by moving the permanent magnet 3 close to the approaching position. In the second embodiment to be describe hereunder, at least one of the position and the posture of the capsule endoscope 1 in the liquid Lq1 is controlled by moving close to the approaching position an electromagnet of which the intensity of the magnetic field is controlled by controlling the driving power.

Figure 13:
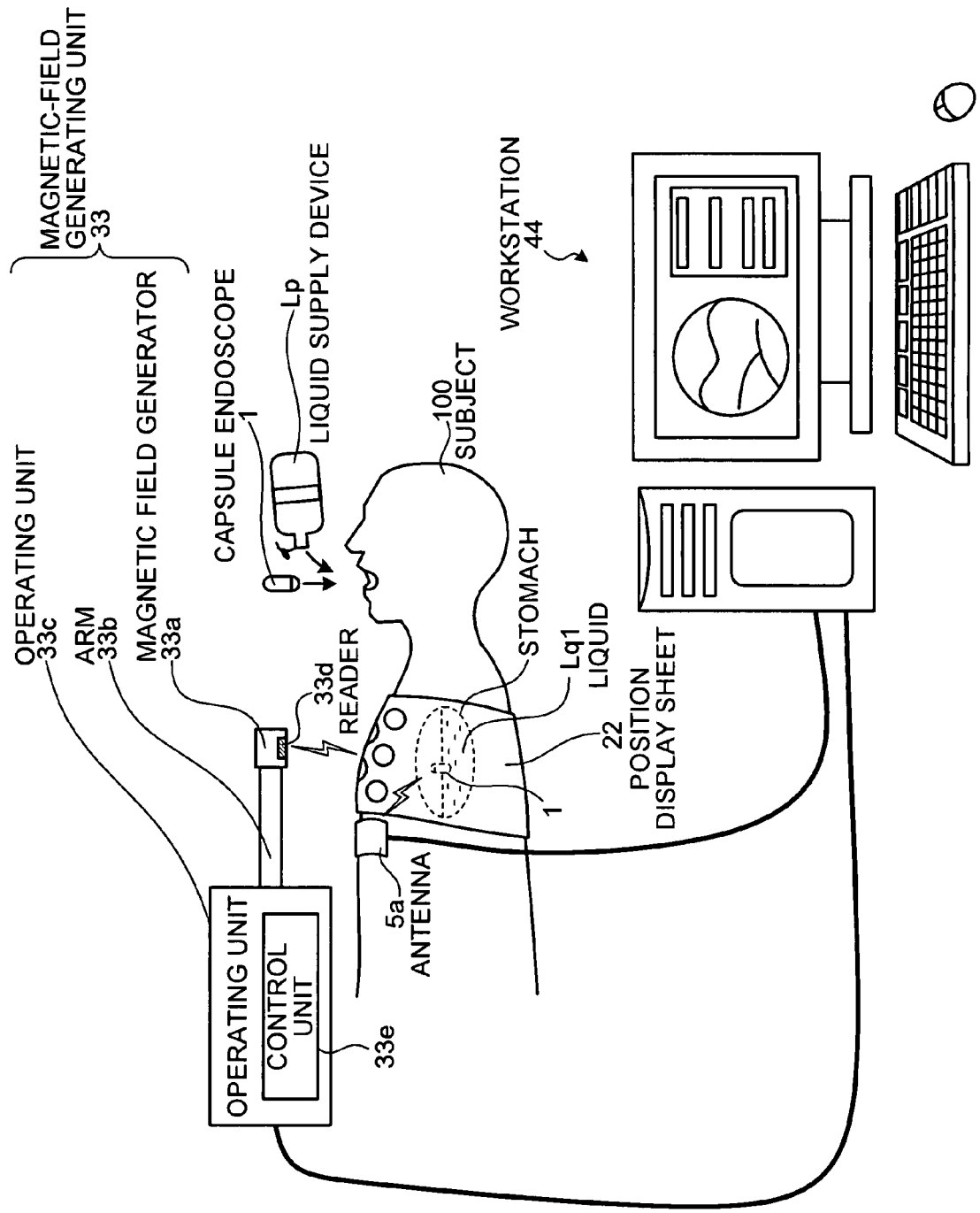
FIG. 13 is a schematic diagram showing a configuration example of a body-insertable device system, which is a second embodiment of the present invention.

FIG. 13 is a schematic diagram showing a configuration example of a body-insertable device system in the second embodiment of the present invention. As shown in FIG. 13, the body-insertable device system of the third embodiment includes a position display sheet 22 in place of the position display sheet 2 in the body-insertable device system of the first embodiment, a magnetic field generator 33 in place of the permanent magnet 3, and a workstation 44 in place of the workstation 4. The remaining arrangement is the substantially same as the corresponding one in the first embodiment. Therefore, like reference numerals are used for designating like or equivalent portions in the first embodiment, for simplicity.

The function of the position display sheet 22 is substantially equal to that of the position display sheet 2 in the first embodiment. The position display sheet 22 presents a plurality of approaching positions on the body surface of the subject 100 that the magnetic field generator 33 approaches, to the examiner. The examiner moves the magnetic field generator 33 close to all the approaching positions, for example. The position display sheet 22 includes information recording media such as RFID tags each storing information to determine an intensity of the magnetic field generated by the magnetic field generator 33 for each approaching position. Those information recording media are placed at the approaching positions presented by the position display sheet 22.

The magnetic field generator 33 functions as a magnetic field generating unit which generates a magnetic field to the capsule endoscope 1 having been introduced into the digestive tract of the subject 100 and changes at least one of the position and the posture of the capsule endoscope 1 by the magnetic field. Specifically, the magnetic field generator 33 is made up of a magnetic field generator 33a for generating a magnetic field to the capsule endoscope 1 having been introduced into the digestive tract of the subject 100, an arm 33b connected at one end to the magnetic field generator 33a, and an operating unit 33c for operating the magnetic field generator 33a through the arm 33b. The magnetic field generator 33a includes a reader 33d for reading information from an information recording medium provided on the position display sheet 22 by way of a radio wave. The operating unit 33c includes a control unit 33e for controlling the driving operations of the magnetic field generator 33a and the reader 33d. The magnetic field generator 33 is electrically connected to the workstation 44 by way of a cable, and is controlled by the workstation 44.

Figure 14:
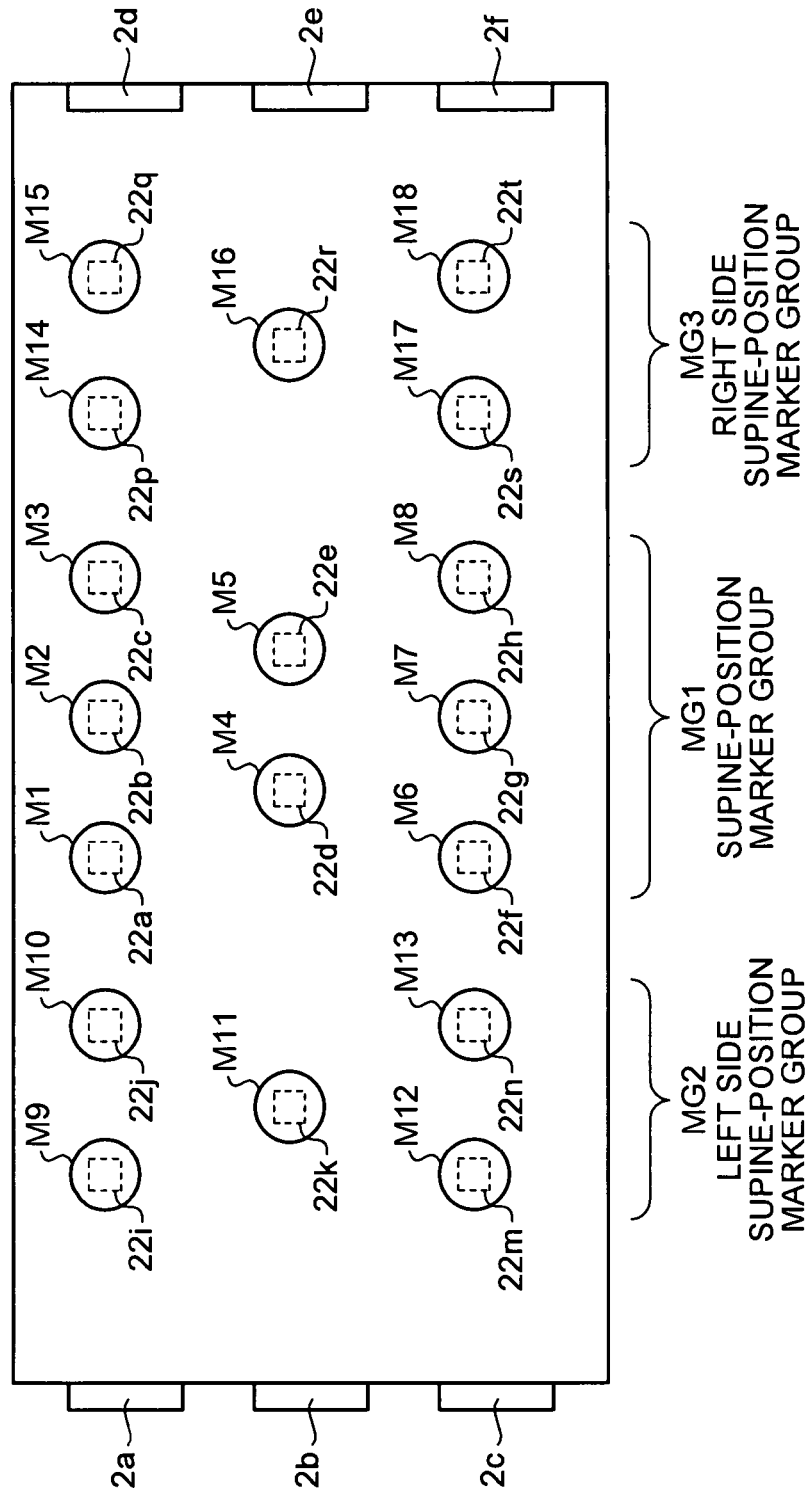
FIG. 14 is a schematic diagram showing a position display sheet in the second embodiment.

The position display sheet 22 in the second embodiment of the invention will be described. FIG. 14 is a schematic diagram showing the position display sheet 22 in the second embodiment. As shown in FIG. 14, in the position display sheet 22, RFID tags 22a to 22t are associatively located near the approaching positions, in place of the magnet numbers as one example of select information of the permanent magnet 3. The remaining construction of the position display sheet 22 is the substantially same as that of the position display sheet in the first embodiment. Like portions are designated by like reference numerals, for simplicity.

The RFID tags 22a to 22t are one example of information recording media storing information (to be referred to as magnetic field determining information) for determining a magnetic intensity of the magnetic field generator 33 to be moved close to the approaching position which is presented by the position display sheet 22. Specifically, the RFID tags 22a to 22t are associatively located near the markers M1 to M18, for example, and each stores the magnetic field determining information for determining a magnetic intensity of the magnetic field generator 33a to be moved close to the markers M1 to M18 for each approaching position. The magnetic field determining information of each of the RFID tags 22a to 22t is read by the reader 33d of the magnetic field generator 33a.

Even when the supine-position marker group MG1, the left side supine-position marker group MG2 and the right side supine-position marker group MG3 have the markers of which the shapes are different from one another, the RFID tags 22a to 22t are also located near the approaching position, respectively. Examples of the magnetic field determining information stored in the RFID tags 22a to 22t are information indicative of a value of current applied to the magnetic field generator 33a, patient information of the subject 100, and information for determining drive power applied to the magnetic field generator 33a such as posture information.

Figure 15:
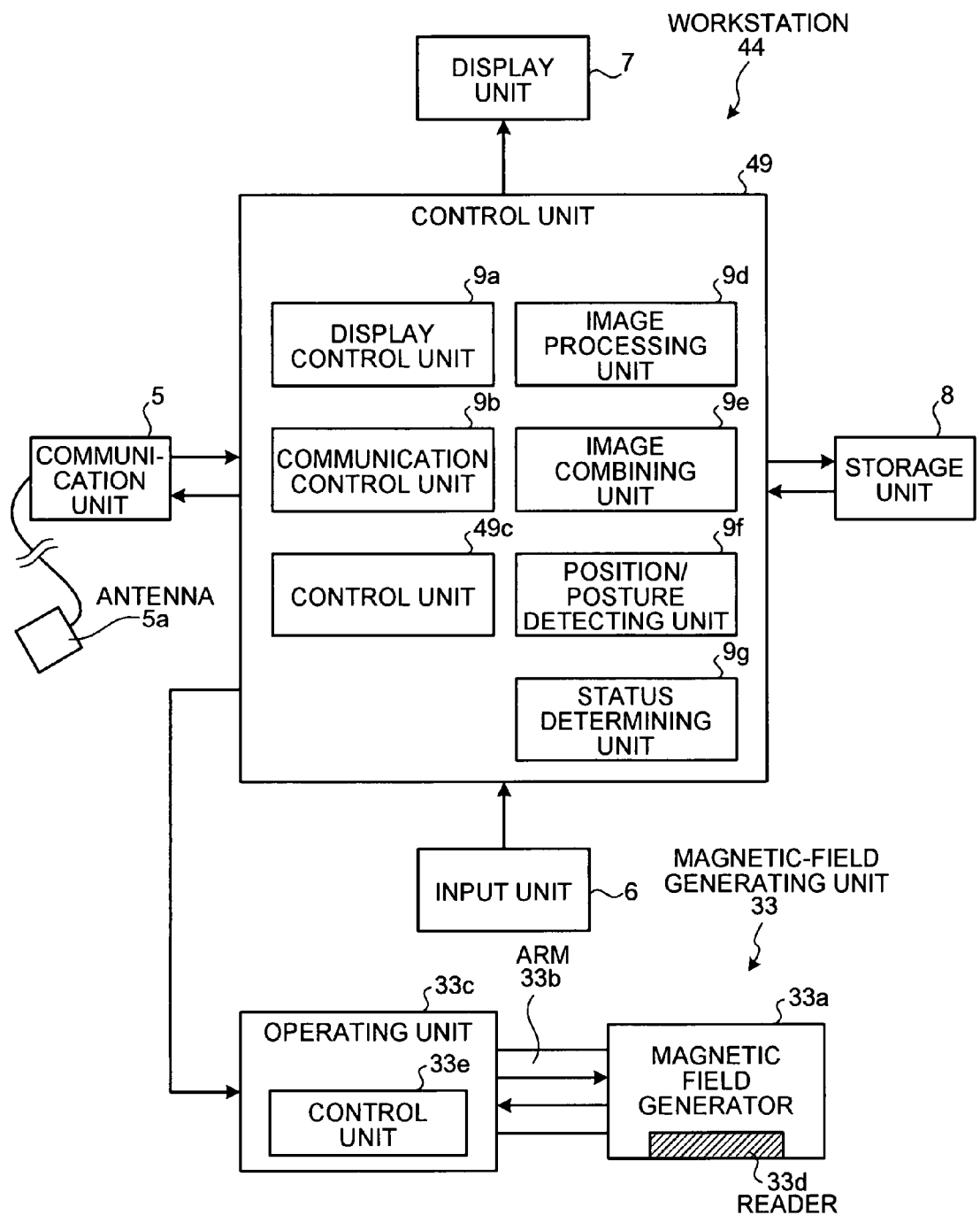
FIG. 15 is a block diagram showing a configuration example including a magnetic field generator and a workstation according to the second embodiment.

The arrangement including the magnetic field generator 33 and the workstation 44 will be described. FIG. 15 is a block diagram showing a configuration example including the magnetic field generator 33 and the workstation 44. As shown in FIG. 15 and as described above, the magnetic field generator 33 includes the magnetic field generator 33a, the arm 33b, the operating unit 33c, the reader 33d, and the control unit 33e. The workstation 44 includes a control unit 49 in place of the control unit 9 of the workstation 4 in the body-insertable device system according to the first embodiment. The control unit 49 includes a power control unit 49c in place of the magnet selecting unit 9c of the control unit 9 in the workstation 4. The remaining arrangement is the substantially same as the corresponding one in the first embodiment. Therefore, like or equivalent portions are designated by like reference numerals, for simplicity.

The magnetic field generator 33a generates a magnetic field for controlling a motion of the capsule endoscope 1 having been introduced into the digestive tract of the subject 100 in the liquid Lq1. Specifically, the magnetic field generator 33a is an electromagnet, for example, and generates a magnetic field when it receives driving power from the operating unit 33c through the arm 33b. The magnetic field generator 33a is moved close to the approaching position presented by the position display sheet 22 and controls at least one of the position and the posture of the capsule endoscope 1, which floats to the surface of the liquid Lq1, by the magnetic field generated when it is energized the driving power.

The magnetic field generator 33a includes the reader 33d as described above. The reader 33d reads the magnetic field determining information stored in the RFID tags 22a to 22t, which are arrayed on the position display sheet 22. When the magnetic field generator 33a is moved close to one of the markers M1 to M18 on the position display sheet 22, the reader 33d reads the magnetic field determining information from the RFID tag (one of the RFID tags 22a to 22t) located near the marker that the magnetic field generator 33a approaches by way of a given radio wave. The reader 33d sends the magnetic field determining information read out to the control unit 33e of the operating unit 33c.

The arm 33b is connected at one end to the magnetic field generator 33a and at the other end to the operating unit 33c, and electrically connects the magnetic field generator 33a to the operating unit 33c. In this case, the arm 33b electrically connects the electromagnet of the magnetic field generator 33a to the control unit 33e, and electrically connects the reader 33d to the control unit 33e.

The operating unit 33c operates the magnetic field generator 33a and the reader 33d, which are provided at the end of the arm 33b. The examiner holds the operating unit 33c with the hand, and manually positions the magnetic field generator 33a and the reader 33d to the position display sheet 22. The operating unit 33c is applied with driving power from the control unit 49 of the workstation 44, and appropriately adjusts the driving power and applies it to the magnetic field generator 33a or the reader 33d. The operating unit 33c is provided with operation switches (not shown) for starting and stopping the driving of the magnetic field generator 33a and the reader 33d, and the control unit 33e for controlling the driving of the magnetic field generator 33a and the reader 33d according to input information from the operation switches.

The control unit 33e controls the driving of the reader 33d according to input information from the operation switch of the operating unit 33c, causes the reader 33d to read the magnetic field determining information stored in the marker (one of the markers M1 to M18) that the magnetic field generator 33a approaches, and acquires the magnetic field determining information read by the reader 33d. The control unit 33e controls the driving operation of the magnetic field generator 33a according to the thus acquired magnetic field determining information. To more specific, the control unit 33e receives the driving power from the control unit 49 of the workstation 44 and adjusts the driving power from the control unit 49 according to the magnetic field determining information. The control unit 33e applies the thus adjusted driving power to the magnetic field generator 33a, and causes the magnetic field generator 33a to generate a magnetic field based on the adjusted driving power. Thus, the control unit 33e adjusts the driving power supplied to the magnetic field generator 33a according to the magnetic field determining information acquired from the reader 33d, and controls the intensity of the magnetic field generated by the magnetic field generator 33a by adjusting the driving power.

The control unit 49 of the workstation 44 has the substantially same function as the control unit 9 of the workstation 4, and controls the driving of the magnetic field generator 33. The control unit 49 further includes the power control unit 49c for controlling the driving power to be supplied to the magnetic field generator 33. The power control unit 49c controls the driving power to be applied to the magnetic field generator 33 on the basis of the result of judging the magnetic field intensity by the status determining unit 9g, and supplies the thus controlled driving power to the magnetic field generator 33. The driving power controlled by the power control unit 49c is applied to the control unit 33e through a cable or the like. In this case, the status determining unit 9g judges an intensity of the magnetic field from the magnetic field generator 33a that is applied to the capsule endoscope 1 according to a magnetic field detection signal received from the capsule endoscope 1.

Figure 16:
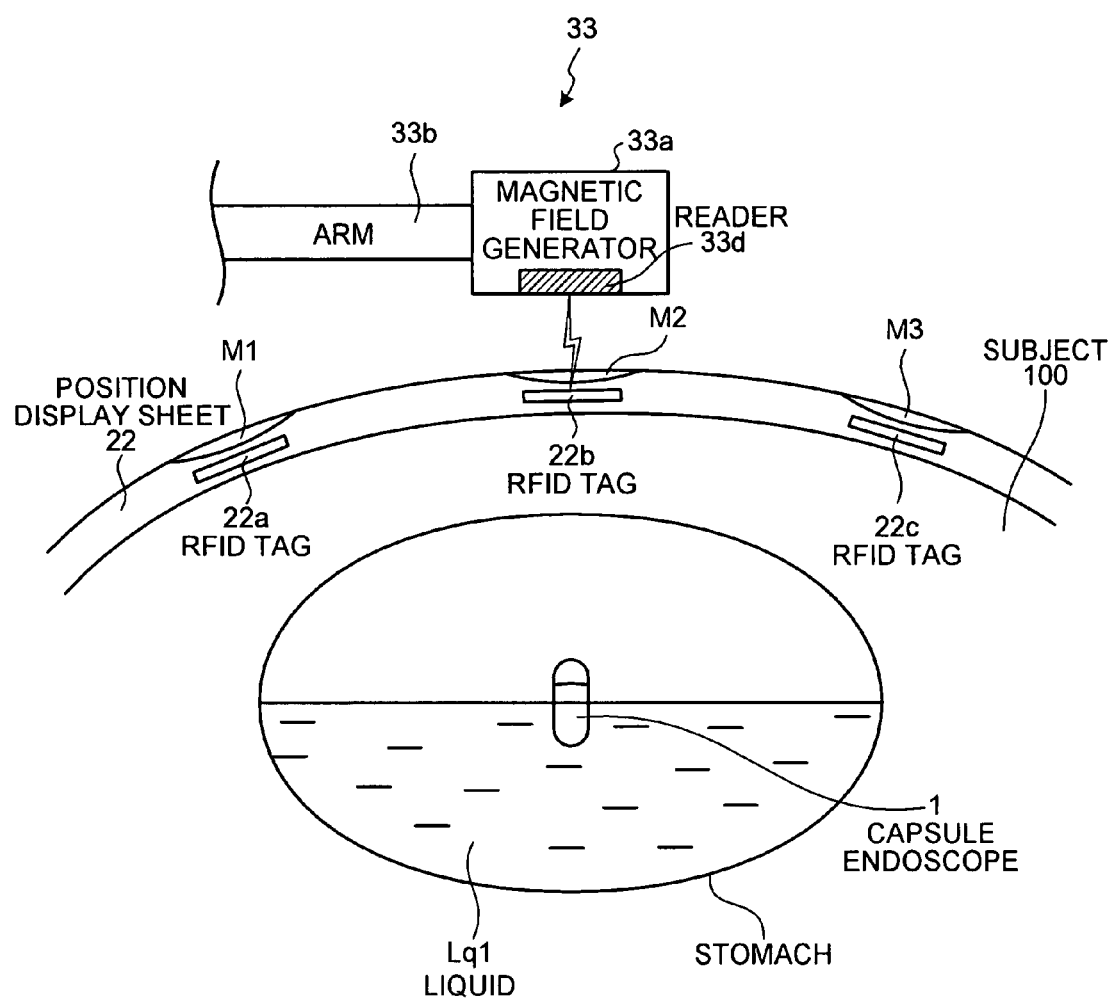
FIG. 16 is a schematic diagram explaining operation of the magnetic field generator which generates magnetic field on the basis of magnetic field determining information read out of an RFID tag located at an approaching position.

The control unit 33e of the magnetic field generator 33 initially sets the driving power supplied to the magnetic field generator 33a on the basis of the magnetic field determining information mentioned above. Subsequently, the control unit applies the driving power controlled by the power control unit 49c to the magnetic field generator 33a, and causes the magnetic field generator 33a to generate a magnetic field based on the driving power. FIG. 16 is a schematic diagram explaining operation of the magnetic field generator 33 which generates magnetic field on the basis of magnetic field determining information read out of an RFID tag located at an approaching position.

As shown in FIG. 16, when the magnetic field generator 33a moves close to the approaching position indicated by the mark M2, for example, the control unit 33e of the magnetic field generator 33 controls the reader 33d to read magnetic field determining information from the RFID tag 22b located near the mark M2, and acquires the magnetic field determining information read by the reader 33d. In this case, the control unit 33e initially sets the driving power to be applied to the magnetic field generator 33a located near the mark M2 according to the thus acquired magnetic field determining information (information indicative of a value of the driving current, patient information of the subject 100, or the like). The magnetic field generator 33a that is applied with the initially set driving power applies a magnetic field of the intensity based on the initially driving power to the capsule endoscope 1 in the stomach, for example, and controls at least one of the position and the posture of the capsule endoscope 1 in the stomach.

Subsequently, when the driving power controlled by the power control unit 49c is applied from the control unit 49 of the workstation 44, the control unit 33e supplies the driving power controlled by the power control unit 49c to the magnetic field generator 33a to cause the magnetic field generator 33a to generate a magnetic field having an intensity based on the driving power. In this case, the control unit 33e re-adjusts the initially set driving power according to an instruction from the power control unit 49c. The control unit 33e controls the driving power for all the approaching positions presented by the position display sheet 22.

The magnetic field generator 33a supplied with such driving power is capable of generating a magnetic field high enough to move the capsule endoscope 1 having been introduced into the subject 100 in the liquid Lq1. The examiner performs the sequence of steps succeeding to the step S101 by using the magnetic field generator 33. By so done, the useful effects comparable with those of the first embodiment are produced.

In the second embodiment, the RFID tags storing the magnetic field determining information are located near the approaching positions, respectively, and the reader 33d of the magnetic field generator 33 reads the magnetic field determining information from the RFID tag located at the approaching position. In an alternative, an optical information recording medium storing the magnetic field intensity are attached to the position display sheet 22 for each approaching position. The reader 33d emits given light to the optical information recording medium to read information from the recording medium. In another alternative, the shapes of the markers on the position display sheet 22 are different for each magnetic field intensity. The reader 33d optically reads the marker shape, and an intensity of a magnetic field generated by the magnetic field generator 33a is determined on the basis of the marker shape read by the reader.

In the second embodiment, the intensity of the magnetic field of the magnetic field generator 33a is initially determined on the basis of the magnetic field determining information read out from the RFID tags arrayed on the position display sheet 22. In an alternative, symbols or characters representative of magnetic intensity or current are associatively located near the approaching positions of the position display sheet 22. The information is visually recognized and a magnetic intensity of the magnetic field generator 33a is manually set. In this case, the operating unit 33c is provided with a power adjusting switch for adjusting driving power to be applied to the magnetic field generator 33a.

The control unit 49 of the workstation 44 may control a magnetic intensity of the magnetic field generator 33a. In this case, the driving power to be applied to the permanent magnet 3a is initially set on the basis of the patient information of the subject 100 input by the input unit 6, for example. The control unit 49 supplies the driving power initially set by the power control unit 49c to the magnetic field generator 33.

As described above, in the second embodiment, the electromagnet in place of the permanent magnet is brought close to the position display sheet, and at least one of the position and the posture of the capsule endoscope 1 according to the first embodiment is controlled by the magnetic field generated by the electromagnet that is moved close to the position display sheet. Accordingly, the present embodiment has useful effects comparable with those of the first embodiment. Further, the magnetic field of the electromagnet to be applied to the capsule endoscope in the digestive tract is easily adjusted, so that a motion of the capsule endoscope in the liquid in the digestive tract is more easily controlled.

Furthermore, in the present embodiment, the position display sheet contains the magnetic field determining information for each approaching position. And the magnetic field determining information is read out every time that the magnet approaches the approaching position, and the magnetic intensity of the magnet is controlled on the basis of the read-out magnetic field determining information. Therefore, the magnetic field of the magnet is reliably applied to the capsule endoscope in the digestive tract, and at least one of the position and the posture of the capsule endoscope is also reliably controlled by the magnetic field. In the second embodiment, an intensity of the generated magnetic field is varied by controlling the current applied to the electromagnet. If required, the intensity of the magnetic field (generated by the permanent magnet for application to the subject) may be varied by changing a distance between the permanent magnet and the subject. A mechanism for changing the distance between the permanent magnet and the subject (distance changing mechanism, not shown) may be used.

Third Embodiment

A third embodiment of the predetermined will be described. As recalled, in the first embodiment, one antenna 5a is connected to the workstation 4, and the capsule endoscope 1 and the workstation 4 wirelessly communicate with each other by way of the antenna 5a. In the third embodiment, a plurality of antennae are connected to the workstation, and the capsule endoscope 1 and the workstation wirelessly communicate with each other by way of one of the antennae.

Figure 17:
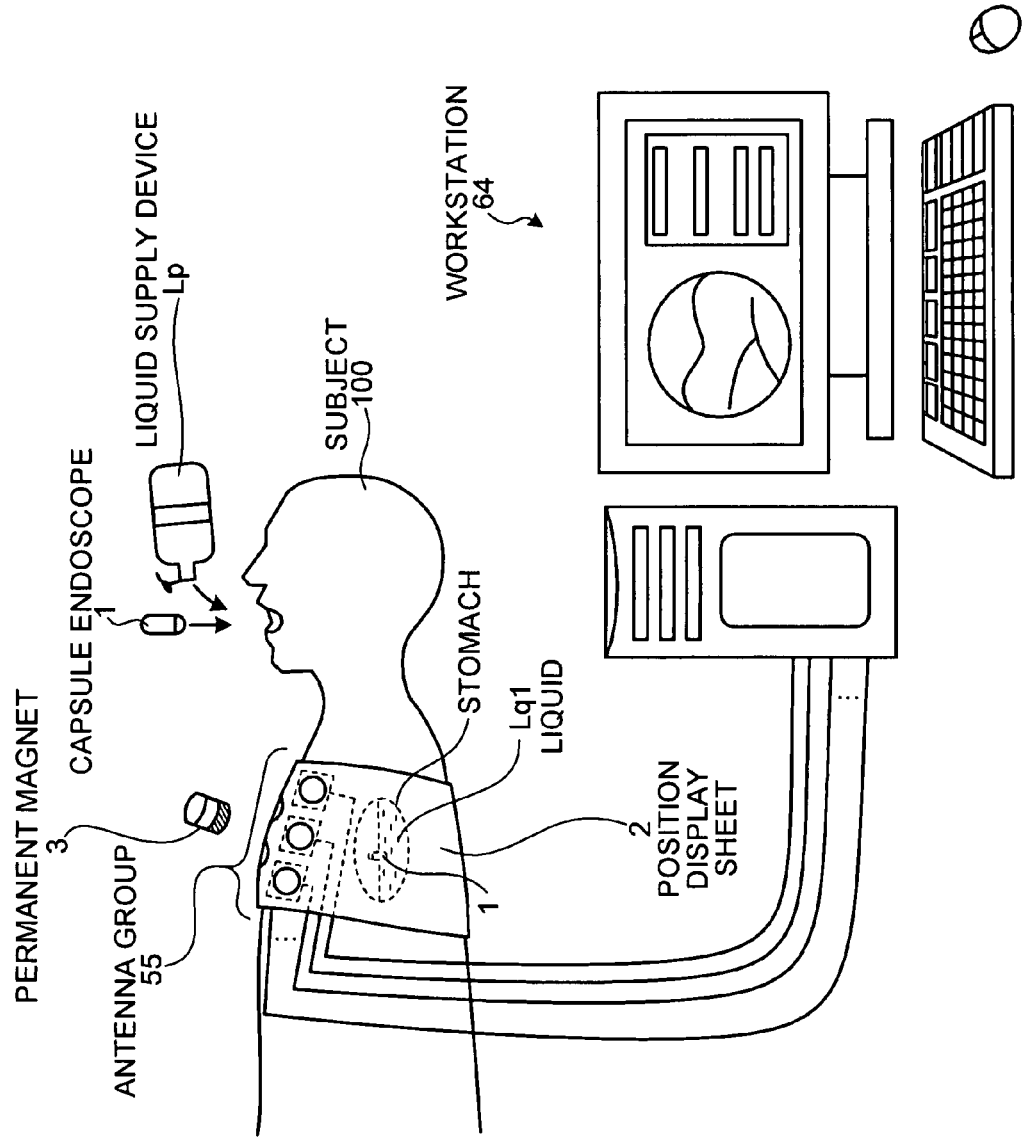
FIG. 17 is a schematic diagram showing a configuration example of a body-insertable device system, which is a third embodiment of the present invention.

FIG. 17 is a schematic diagram showing a configuration example of a body-insertable device system, which is an third embodiment of the present invention. As shown in FIG. 17, the body-insertable device system according to the third embodiment uses a workstation 64 in place of the workstation 4 in the body-insertable device system of the first embodiment. The workstation 64 includes an antenna group 55 in place of one antenna 5a connected to the workstation 4 in the first embodiment. The remaining arrangement is the substantially same as the corresponding one in the first embodiment. Therefore, like reference numerals are used for designating like or equivalent portions in the first embodiment, for simplicity.

The antenna group 55 is used for performing a radio communication between the capsule endoscope 1 having been introduced into the digestive tract of the subject 100 and the workstation 64. Specifically, the antennae of the antenna group 55 are located in association with the approaching positions presented by the position display sheet 2, respectively. Those antennae are electrically connected to the workstation 64 by a cable or the like. At least one antenna of the antenna group 55 transfers and receives radio signals in high sensitivity to and from the capsule endoscope 1 having been introduced into the digestive tract of the subject 100, and receives image signals and the like from the capsule endoscope 1 in high sensitivity.

Figure 18:
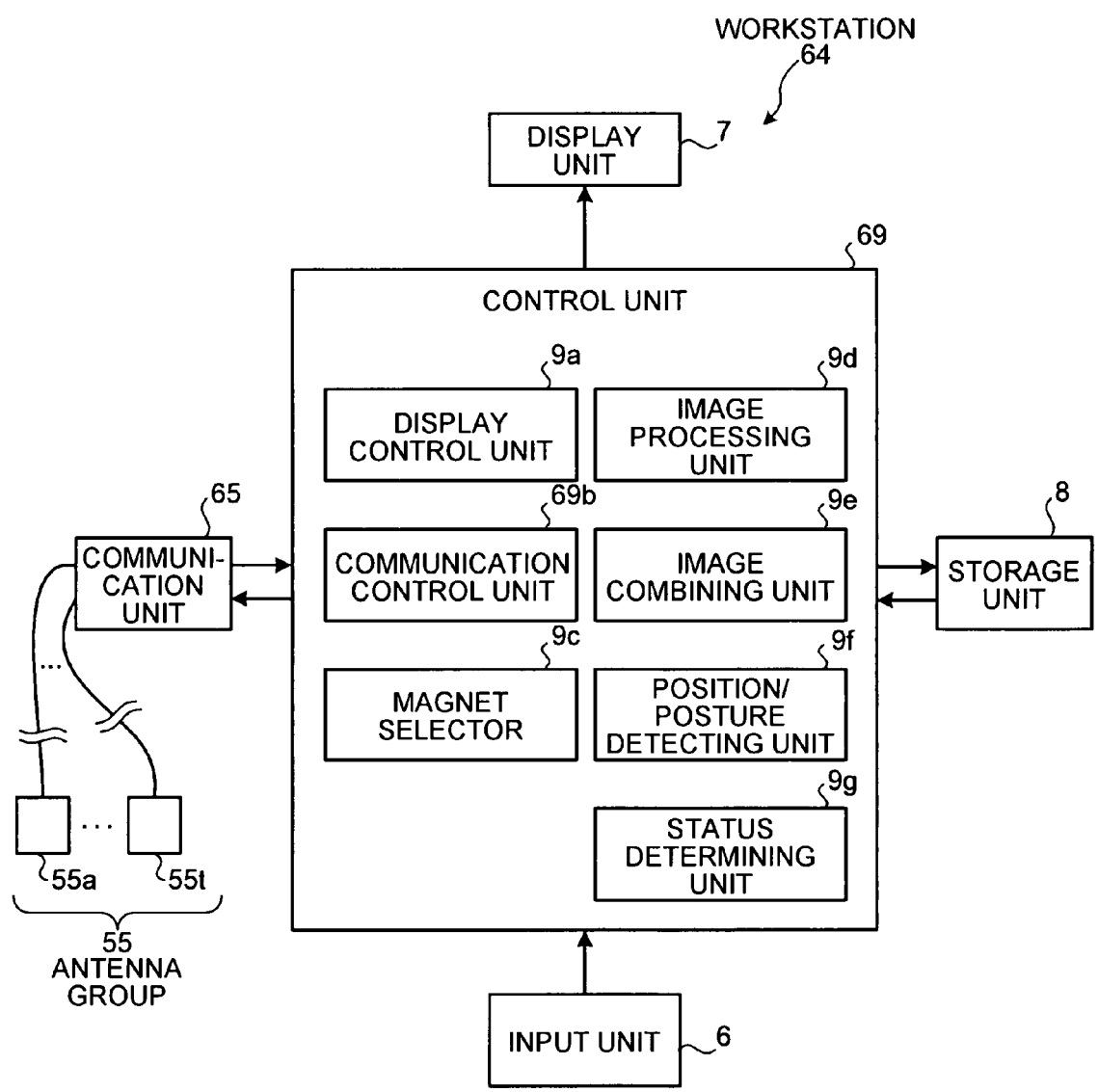
FIG. 18 is a block diagram schematically showing a configuration example of a workstation in the third embodiment.

An arrangement of the workstation 64 in the third embodiment will be described. FIG. 18 is a block diagram schematically showing the configuration example of the workstation in the third embodiment. As shown in FIG. 18, the workstation 64 in the third embodiment has a communication unit 65 in place of the communication unit 5 in the workstation 4 in the body-insertable device system of the first embodiment, and has a control unit 69 in place of the control unit 9. The control unit 69 includes a communication control unit 69b in place of the communication control unit 9b of the control unit 9 in the workstation 4 already stated. The remaining arrangement is the substantially same as the corresponding one in the first embodiment. Therefore, like or equivalent portions are designated by like reference numerals, for simplicity.

The communication unit 65 is used for performing a radio communication between the capsule endoscope 1 and the workstation 64 by using the antenna group 55. Specifically, the communication unit 65 is connected to the antennae (a total of 18 antennae 55a to 55t corresponding to the markers M1 to M18 on the position display sheet 2, for example) by way of cables. The communication unit demodulates in a predetermined demodulation mode a radio signal received through one of the antennae of the antenna group 55 and acquires various kinds of information from the capsule endoscope 1. In this case, the communication unit 65 compares field strength of the antennae of the antenna group 55 with one another to select the antenna having the highest field strength in the antenna group 55, and receives a radio signal through the selected one. The communication unit 65 receives a radio signal in high sensitivity from the capsule endoscope 1 through the antenna having the highest field strength. Thereafter, the communication unit 65 acquires the image information obtained by the imaging unit 12 and motion information of the casing 10 in low noise levels from the radio signal coming from the capsule endoscope 1, and sends the image information and the motion information, which suffer from low noise, to the communication control unit 69. The communication unit 65 acquires a magnetic field detection signal representative of the result of detecting a magnetic intensity, derived from the magnetic sensor 15, in low noise levels, and sends the acquired low-noise magnetic field detection signal to the communication control unit 69.

The communication unit 65 demodulates a control signal to the capsule endoscope 1, which is received from the communication control unit 69, in a given demodulation mode, to form a radio signal. In this case, the communication unit 65 sends a given test signal from all the antennae of the antenna group 55 and causes the capsule endoscope 1 to send an acknowledgement signal to the test signal back to the communication unit. The communication unit 65 compares the field strengths of the antennae when they receive the acknowledgement signal from the capsule endoscope 1 to select the antenna having the highest field strength in the antenna group 55 and to send a radio signal to the selected one. Thus, the communication unit 65 sends a radio signal to the capsule endoscope 1 via the antenna having the highest field strength in the antenna group 55. Accordingly, the communication unit 65 reliably sends a control signal instructing the imaging unit 12, for example, to start its imaging operation to the capsule endoscope 1.

The communication control unit 69 has the substantially same function as of the control unit 9 in the workstation 4, and controls the driving operation of the communication unit 65 that is connected to the antenna group 55. The communication control unit 69 further includes the communication control unit 69b for controlling the driving operation of the communication unit 65, in place of the communication unit 5 which uses one antenna 5a for radio communication. The communication control unit 69b, as described above, controls the driving operation of the communication unit 65 so as to receive the radio signal from the capsule endoscope 1 via the antenna having the highest field strength, and acquires the image information or the motion information in low noise levels from the communication unit 65. Or, the communication control unit 69b acquires a magnetic-field detection signal in low noise levels from the communication unit 65. The communication control unit 69b sends a control signal to the capsule endoscope 1 to the communication unit 65 to cause the communication unit to generate a radio signal containing the control signal, and causes the communication unit 65 to send, as described above, the generated radio signal via the antenna having the highest field strength to the capsule endoscope.

Figure 19:
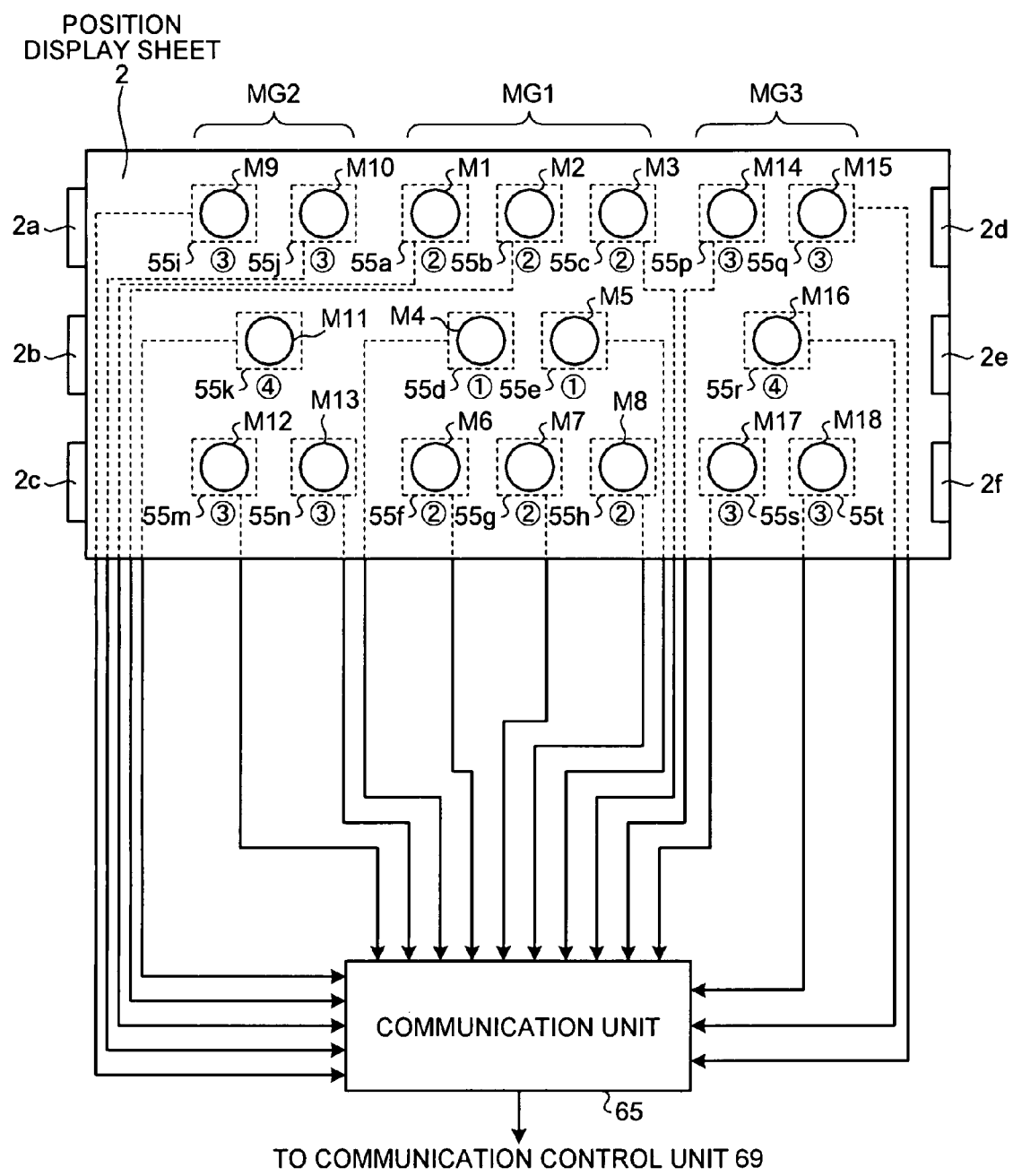
FIG. 19 is a schematic diagram showing an arrangement of a group of antennae, which are arranged on the position display sheet in association with a plurality of approaching positions.

An arrangement of the antennae of the antenna group 55 on the position display sheet 2 will be described. FIG. 19 is a schematic diagram showing a group of antennae, which are arranged on the position display sheet 2 in association with a plurality of approaching positions. As shown in FIG. 19, the antennae of the antenna group 55 are arranged on the position display sheet 2 in association with the plurality of approaching positions presented by the position display sheet 2. To be more specific, a total of 18 antennae 55a to 55t of the antenna group 55 are respectively arranged on the position display sheet 2 in association with 18 approaching positions indicated by the markers M1 to M18 formed on the position display sheet 2. For example, the antennae 55a to 55t are located near the markers M1 to M18, respectively. Those antennae 55a to 55t are connected to the communication unit 65 by way of cables or the like. The communication unit 65, as described above, is connected to the communication control unit 69 of the workstation 64.

The antennae 55a to 55t, which are arranged on the position display sheet 2 in association with the approaching positions as described above, are used for transmitting and receiving radio signals to and from the capsule endoscope 1 having been introduced into the digestive tract of the subject 100. At least one of the antennae 55a to 55t is used for transmitting and receiving radio signals in high sensitivity to and from the capsule endoscope 1, which is caught by the magnetic force of the permanent magnet 3, for example, which is located near the approaching position on the position display sheet 2. Specifically, the antennae 55a to 55t are arranged on the position display sheet 2 in association with the approaching positions. Therefore, those antennae are located at positions relative to the positions (catching positions) at which the capsule endoscope 1 is caught by the magnetic forces of the permanent magnets 3, for example, located near the approaching positions. The antennae 55a to 55t are each positioned relative to the capsule endoscope 1 at each catching position so as to allow at least one of the antennae 55a to 55t to wirelessly send and receive signals to and from the capsule endoscope 1 in high sensitivity.

Figure 20:
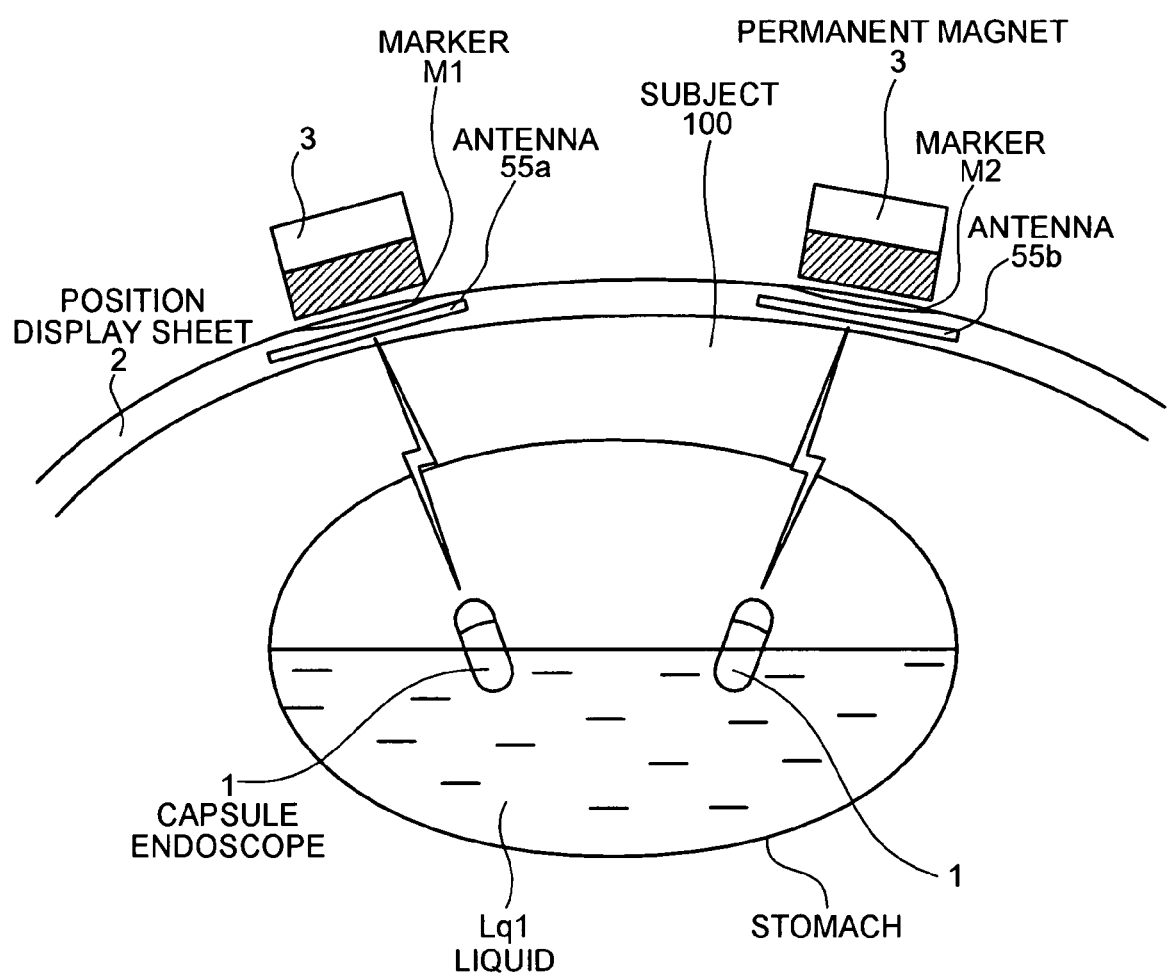
FIG. 20 is a schematic diagram showing how the antennae, which are arranged on the position display sheet in association with the approaching positions, and the capsule endoscope send and receive radio signal.

To be more specific, when the permanent magnet 3 is moved close to the approaching position indicated by the marker M1, the capsule endoscope 1 in the stomach of the subject 100, as shown in FIG. 20, for example, is caught by the magnetic force of the permanent magnet 3 that is brought to the marker M1. In this case, the capsule endoscope 1 is caught at a predetermined position relative to the antenna 55a located in association with the approaching position. The capsule endoscope 1 caught at the relative position is allowed to wirelessly send and receive signals to and from the antenna 55a in high sensitivity. When the permanent magnet 3 is moved close to the approaching position indicated by the marker M2, the capsule endoscope 1 in the stomach is likewise caught by the magnetic force of the permanent magnet 3 located near the marker M2. In this case, the capsule endoscope 1 is caught at a predetermined position relative to the antenna 55b located in association with the approaching position. The capsule endoscope 1 caught at the relative position is allowed to wirelessly send and receive signals to and from the antenna 55b in high sensitivity. The same thing correspondingly applies to all the antennae 55a to 55t located on the position display sheet 2 in association with the approaching positions.

In the third embodiment, the antennae of the antenna group 55 are arranged on the position display sheet 2 in a state that the antennae overlap with the markers, respectively. In alternative, the antennae of the antenna group 55 may be arranged on the position display sheet 2 in association with the approaching positions, respectively. Those antennae may be located at any positions on the position display sheet 2 if the antennae are arranged at such relative positions as to ensure the transmission and reception of radio signals to and from the capsule endoscope in high sensitivity. The positions at which the antennae of the antenna group 55 are located may be determined on the basis of experimental results. It suffices that the number of the antennae of the antenna group 55 is equal to that of the approaching positions presented by the position display sheet 2. The number of the antennae is not limited to 18 in particular.

As described above, the third embodiment is similar in construction to the first embodiment. The antennae are arranged on the position display sheet in association with the plurality of approaching positions, respectively. Those antennae are located at such positions as to ensure that when the capsule endoscope having been introduced into the digestive tract of the subject is magnetically caught, one of the antennae transmits and receives radio signals to and from the caught capsule endoscope in high sensitivity. Therefore, radio signals are received in high sensitivity from the capsule endoscope by way of any of the antennae. The instant embodiment also produces the useful effects of the first embodiment, and further always acquires the images of the inside of the digestive tract, picked up by the capsule endoscope in low noise levels.

As seen from the foregoing description, when the body-insertable device system of the third embodiment is used, the examiner always displays the images of the inside of the digestive tract in low noise levels on the display, and more readily observes the insides of the subject by using such low-noise images.

Fourth Embodiment

A fourth embodiment of the present invention will be described. In the first embodiment, at least one of the position and the posture of the capsule endoscope 1 having been introduced into the digestive tract is magnetically controlled. In the fourth embodiment, the capsule endoscope 1 is moved close to a desired position such as the affected part in the digestive tract and picks up an enlarged image of the designated position.

Figure 21:
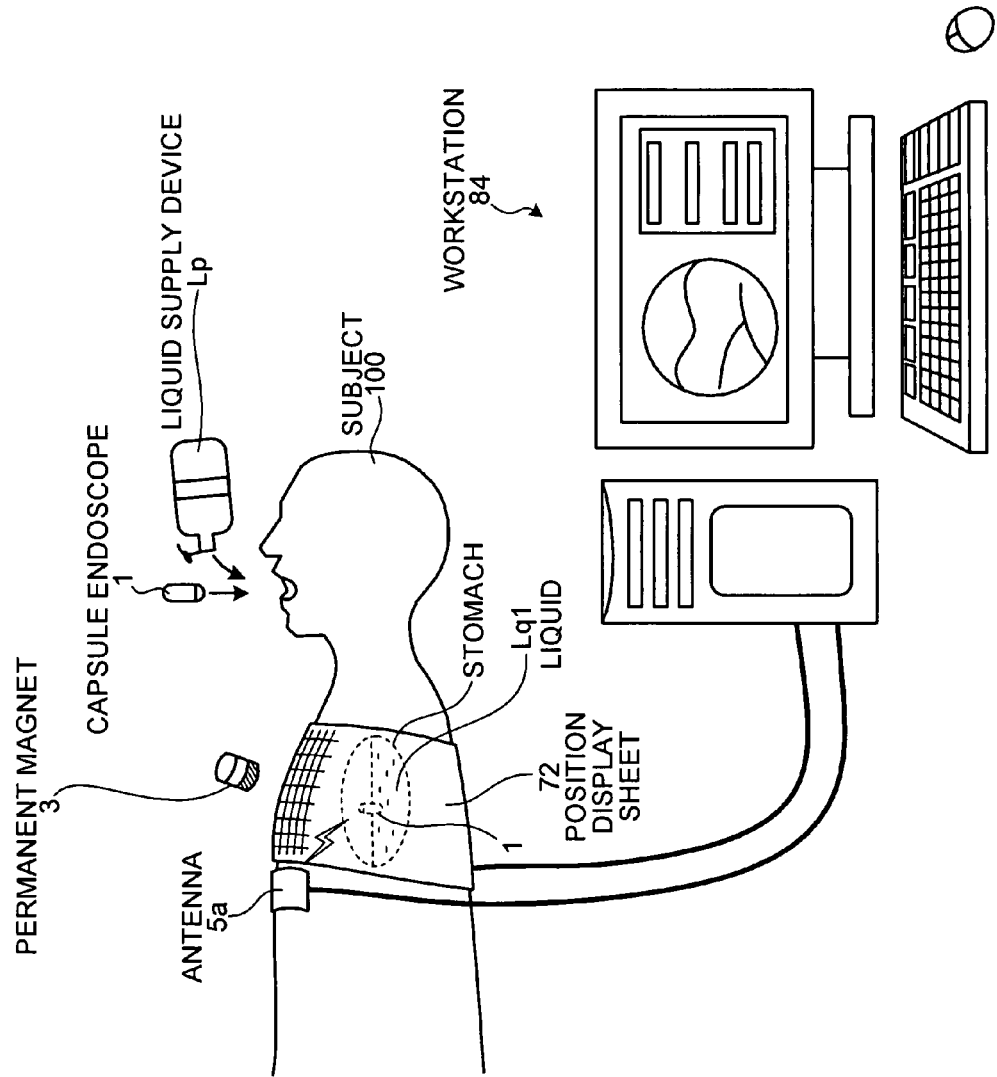
FIG. 21 is a schematic diagram showing a configuration example of a body-insertable device system in a fourth embodiment of the present invention.

FIG. 21 is a schematic diagram showing a configuration example of a body-insertable device system in the fourth embodiment of the present invention. As shown in FIG. 21, the body-insertable device system of the fourth embodiment uses a position display sheet 72 in place of the position display sheet 2 of the body-insertable device system of the first embodiment, and a workstation 84 in place of the workstation 4. The remaining arrangement is the substantially same as the corresponding one in the first embodiment. Therefore, like reference numerals are used for designating like or equivalent portions in the first embodiment, for simplicity.

Figure 22:
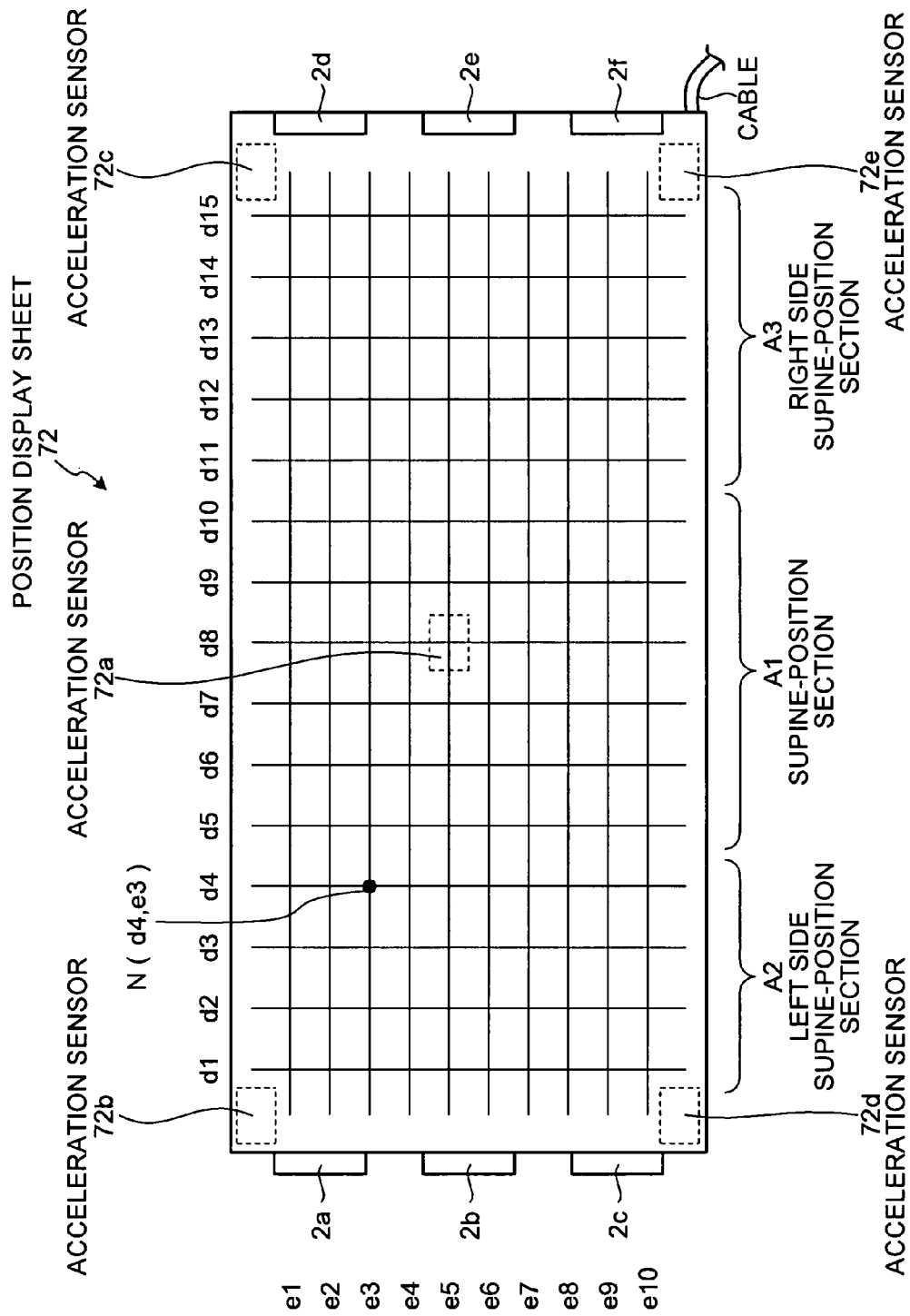
FIG. 22 is a schematic diagram showing a configuration example of a position display sheet in the fourth embodiment.

A configuration of the position display sheet 72 in the fourth embodiment will be described in detail. FIG. 22 is a schematic diagram showing a configuration of a position display sheet 72 in the fourth embodiment. As shown in FIG. 22, the position display sheet 72 contains a plurality of vertical lines d1 to d15 and a plurality of horizontal lines e1 to e10 in place of the markers M1 to M18 on the position display sheet 2 in the first embodiment. The position display sheet 72 further includes a plurality of acceleration sensors 72a to 72e. The remaining configuration is the substantially same as the corresponding one in the first embodiment. Therefore, like reference numerals are used for designating like or equivalent portions in the first embodiment, for simplicity.

The vertical lines d1 to d15 and the horizontal lines e1 to e10 formed on the position display sheet 72 are provided for presenting a plurality of the approaching positions as mentioned above.

Specifically, the vertical lines d1 to d15 and the horizontal lines e1 to e10 cross to form a lattice pattern. The cross points of the lattice represent the approaching positions, respectively. In this case, an approaching position N shown in FIG. 22 lies at a cross point of the vertical line d4 and the horizontal line e3, and is defined by the coordinates (d4, e3) in a coordinate system constructed by the vertical lines d1 to d15 and the horizontal lines e1 to e10.

The numbers of the vertical lines and the horizontal line are not limited to 10 and 15, particular. At least one line suffices for each of the required numbers of those lines.

The position display sheet 72 is divided into a supine-position section A1, a left side supine-position section A2, and a right side supine-position section A3 corresponding to the posture of the subject 100. The supine-position section A1 contains the approaching positions on the subject 100 who is in supine position. In this section, the approaching positions are located at the cross points of the vertical lines d5 to d10 and the horizontal lines e1 to e10. The left side supine-position section A2 contains the approaching positions on the subject 100 who is in left side supine position. In this section, the approaching positions are located at the cross points of the vertical lines d1 to d4 and the horizontal lines e1 to e10.

The right side supine-position section A3 contains the approaching positions on the subject 100 who is in right side supine position. In this section, the approaching positions are located at the cross points of the vertical lines d11 to d15 and the horizontal lines e1 to e10. When putting the subject 100 wearing the position display sheet 72 in supine position, the examiner moves the right side supine-position section A3 close to any of the approaching positions located at the cross points in the supine-position section A1. When putting the subject 100 in left-side supine position, the examiner moves the permanent magnet 3 close to any of the approaching positions located at the cross points in the left side supine-position section A2. When putting the subject 100 in right-side supine position, the examiner moves the permanent magnet 3 close to any of the approaching positions located at the cross points in the right side supine-position section A3. The permanent magnet 3 having been moved to the approaching position controls at least one of the position and the posture of the capsule endoscope 1 having been introduced into the digestive tract of the subject 100, as in the first embodiment.

Further, the position display sheet 72 includes a plurality of acceleration sensors 72a to 72e, as described above. The acceleration sensor 72a is fixedly located at a position near the central part of the position display sheet 72, e.g., near the approaching position specified by the coordinates (d8, e5). The acceleration sensors 72b to 72e are fixedly located at the four corners of the position display sheet 72. The acceleration sensors 72a to 72e are electrically connected to the workstation 84 by way of the cable or the like. When the position display sheet 72 displaces in the spatial coordinate system xyz, those sensors detect an acceleration of the position display sheet. The detection result is sent to the workstation 84. The acceleration sensor 72a detects an acceleration of the position display sheet 72 when the central part of the position display sheet 72 displaces in the spatial coordinate system xyz. The result of detecting the acceleration of the central part of the position display sheet 72 is sent to the workstation 84. The acceleration sensors 72b to 72e detects the accelerations at the corners of the position display sheet 72 when those corners displace in the spatial coordinate system xyz. The result of detecting the accelerations at the corners of the position display sheet 72 is sent to the workstation 84. The number of the acceleration sensors fixedly located on the position display sheet 72 is not limited to 5 if those sensors are fixedly located at the four corners and the central part of the position display sheet 72.

Figure 23:
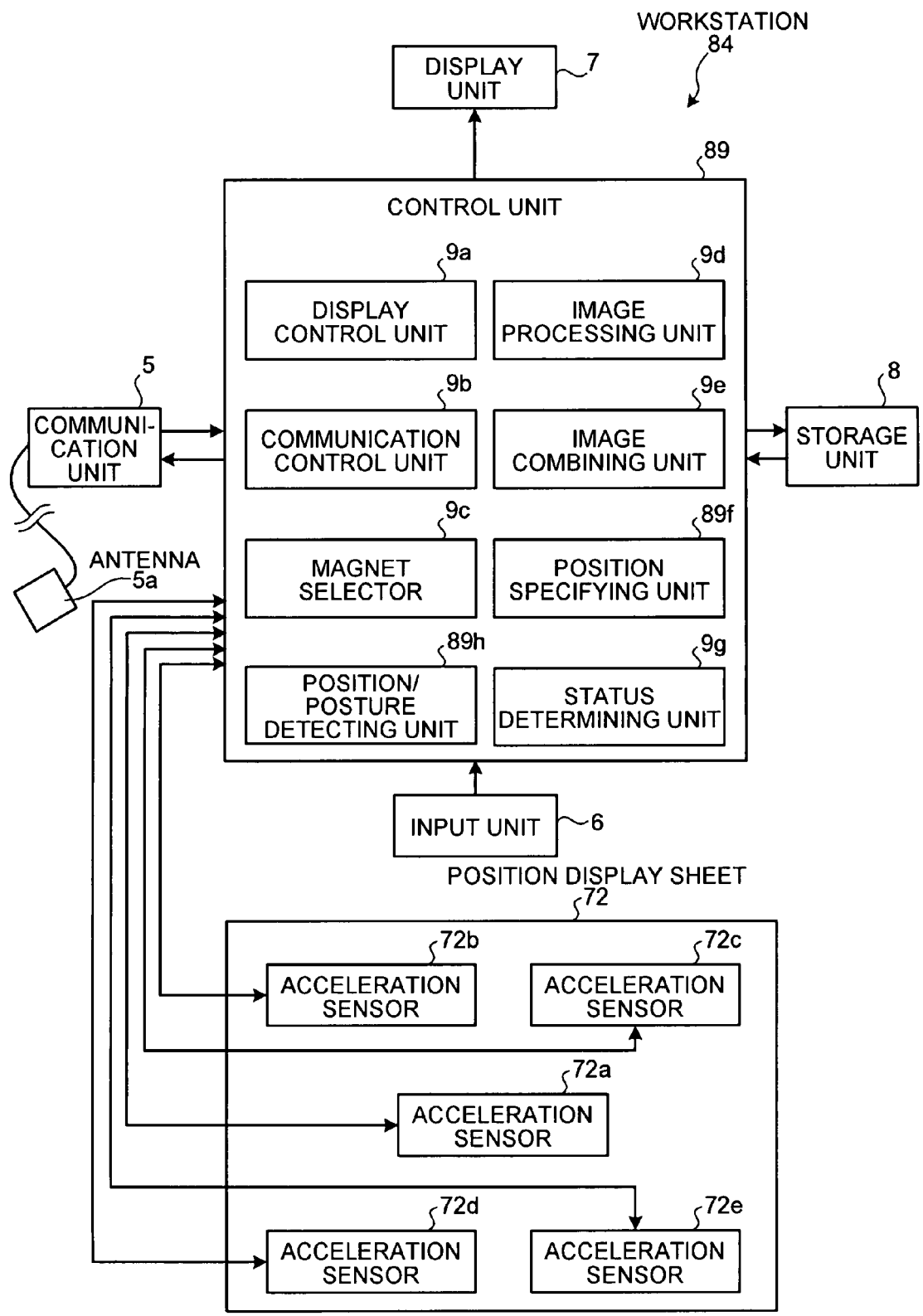
FIG. 23 is a block diagram schematically showing a configuration example of a workstation used in the fourth embodiment.

A configuration of the workstation 84 in the fourth embodiment of the invention will be described in detail. FIG. 23 is a block diagram schematically showing the configuration example of the workstation 84 used in the fourth embodiment. As shown in FIG. 23, the workstation 84 has a control unit 89 in place of the control unit 9 in the workstation 4 in the first embodiment. The control unit 89 has a position/posture detecting unit 89f in place of the position/posture detecting unit 9f of the control unit 9 in the workstation 4, and further a position specifying part 89h. The control unit 89 is electrically connected to the acceleration sensors 72a to 72e of the position display sheet 72. The remaining arrangement is the substantially same as the corresponding one in the first embodiment. Therefore, like reference numerals are used for designating like or equivalent portions in the first embodiment, for simplicity.

The control unit 89 has the substantially same functions as those of the control unit 9 in the workstation 4. The control unit 89 controls the driving of the acceleration sensors 72a to 72e, which are fixedly located on the position display sheet 72, and has functions to detect a pane position of the position display sheet 72 in the spatial coordinate system xyz, to specify the approaching position corresponding to a desired position designated in the images of the inside of the digestive tract, and to present the specified approaching position to the examiner. The control unit 89, as described, includes the position/posture detecting unit 89f and the position specifying part 89h.

The position/posture detecting unit 89f detects a position and a posture of the capsule endoscope 1 in the spatial coordinate system xyz, like the position/posture detecting unit 9f of the workstation 4. Further, the position/posture detecting unit 89f detects a positional relationship of the capsule endoscope 1 and the position display sheet 72 in the spatial coordinate system xyz. To this end, the position/posture detecting unit 89f detects a plane position of the position display sheet 72 in the spatial coordinate system xyz on the basis of the acceleration detection results acquired from the acceleration sensors 72a to 72e.

To be more specific, the position/posture detecting unit 89f first sets up the spatial coordinate system xyz. The position display sheet 72 is placed flat on the x-y plane of the spatial coordinate system xyz in a state that the origin O of the spatial coordinate system xyz is coincident with the position of the acceleration sensor 72a. The capsule endoscope 1, as described above, is located at the origin O of the spatial coordinate system xyz in a state that the diameter axis C2b, the major axis C1 and the diameter axis C2a are coincident with the x-axis, y-axis and z-axis, respectively of the spatial coordinate system xyz. The position/posture detecting unit 89f knows the position and the posture of the capsule endoscope 1 which is placed in the spatial coordinate system xyz and the plane position of the position display sheet 72, as initial states. The position/posture detecting unit 89f successively detects the position and the posture of the capsule endoscope 1 and the plane position of the position display sheet 72, which successively change from the initial states. In this case, the position/posture detecting unit 89f successively detects the position and the posture of the capsule endoscope 1 in the spatial coordinate system xyz on the basis of motion information of the capsule endoscope 1 already stated. The position/posture detecting unit 89f successively calculates movement quantities (vector quantities) of the central part and the four corners of the position display sheet 72 on the basis of the acceleration detection results acquired from the acceleration sensors 72a to 72e, and successively detects the current plane position of the position display sheet 72 in the spatial coordinate system xyz on the basis of the calculated movement quantities. In this way, the position/posture detecting unit 89f successively detects the plane position of the position display sheet 72 repeatedly undergoing changes of displacement, curving, etc., from the initial states in the spatial coordinate system xyz.

The thus functioning position/posture detecting unit 89f successively detects the current positional relationship between the capsule endoscope 1 and the position display sheet 72 in the spatial coordinate system xyz on the basis of the successively detected positions and postures of the capsule endoscope 1 and the plane position of the position display sheet 72. Thereafter, the control unit 89, as in the case of the first embodiment, stores the position and posture (position/posture) information of the capsule endoscope 1 into the storage unit 8, and associates the plane position of the position display sheet 72 detected by the position/posture detecting unit 89f with the position/posture information, and stores the results into the storage unit 8. The positional relationship between the capsule endoscope 1 and the position display sheet 72 includes the relative position of the capsule endoscope 1 to the position display sheet 72 in the spatial coordinate system xyz and the posture of the capsule endoscope 1 with respect to the plane of the position display sheet 72.

The position specifying part 89h functions as a specifying unit for specifying the approaching position corresponding to a desired position specified in the images of the inside of the digestive tract picked up by the capsule endoscope 1. Specifically, the position specifying part 89h acquires designated position information for designating a designated position in the images of the digestive tract from the input unit 6, and specifies the approaching position corresponding to the designated position from a plurality of approaching positions on the position display sheet 72 on the basis of the positional relationship of the capsule endoscope 1 and the position display sheet 72 and the designated position information. In this case, the input unit 6 serves as input unit for inputting to the control unit 89 the designated position information of the desired position, which is specified through the manual operation by the examiner, in the images of the digestive tract displayed by the display unit 7.

The information indicative of the approaching position specified by the position specifying part 89h is displayed by the display unit 7. If the position specifying part 89h specifies the approaching position corresponding to the designated position, the display control unit 9a causes the display unit 7 to display information indicating that the specified approaching position corresponds to which of those approaching positions on the position display sheet 72 corresponds to the specified approaching position. Accordingly, the examiner easily finds the approaching position, which corresponds to the designated position, from the plurality of approaching positions on the position display sheet 72 based on the information displayed on the display 7. The display unit 7 serves as a specified position display unit for displaying the approaching position specified by the position specifying part 89h.

Figure 24:
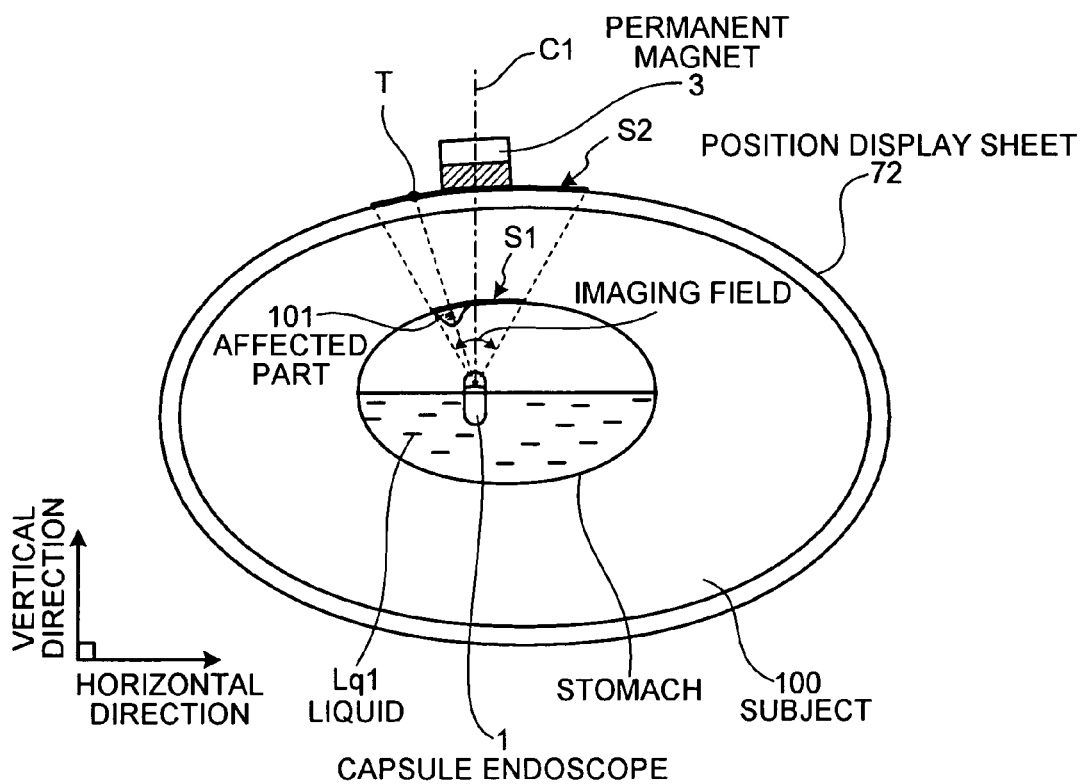
FIG. 24 is a schematic diagram showing a state that the capsule endoscope in the stomach is caught by a magnetic force of the permanent magnet which is moved close to the approaching position shown on the position display sheet.
Figure 25:
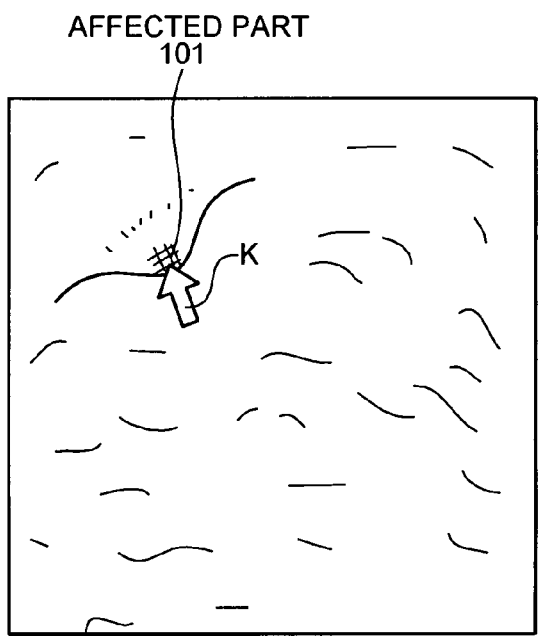
FIG. 25 is a schematic diagram showing an image of the inside of the stomach picked up by the capsule endoscope that is caught in the FIG. 24 state.
Figure 26:
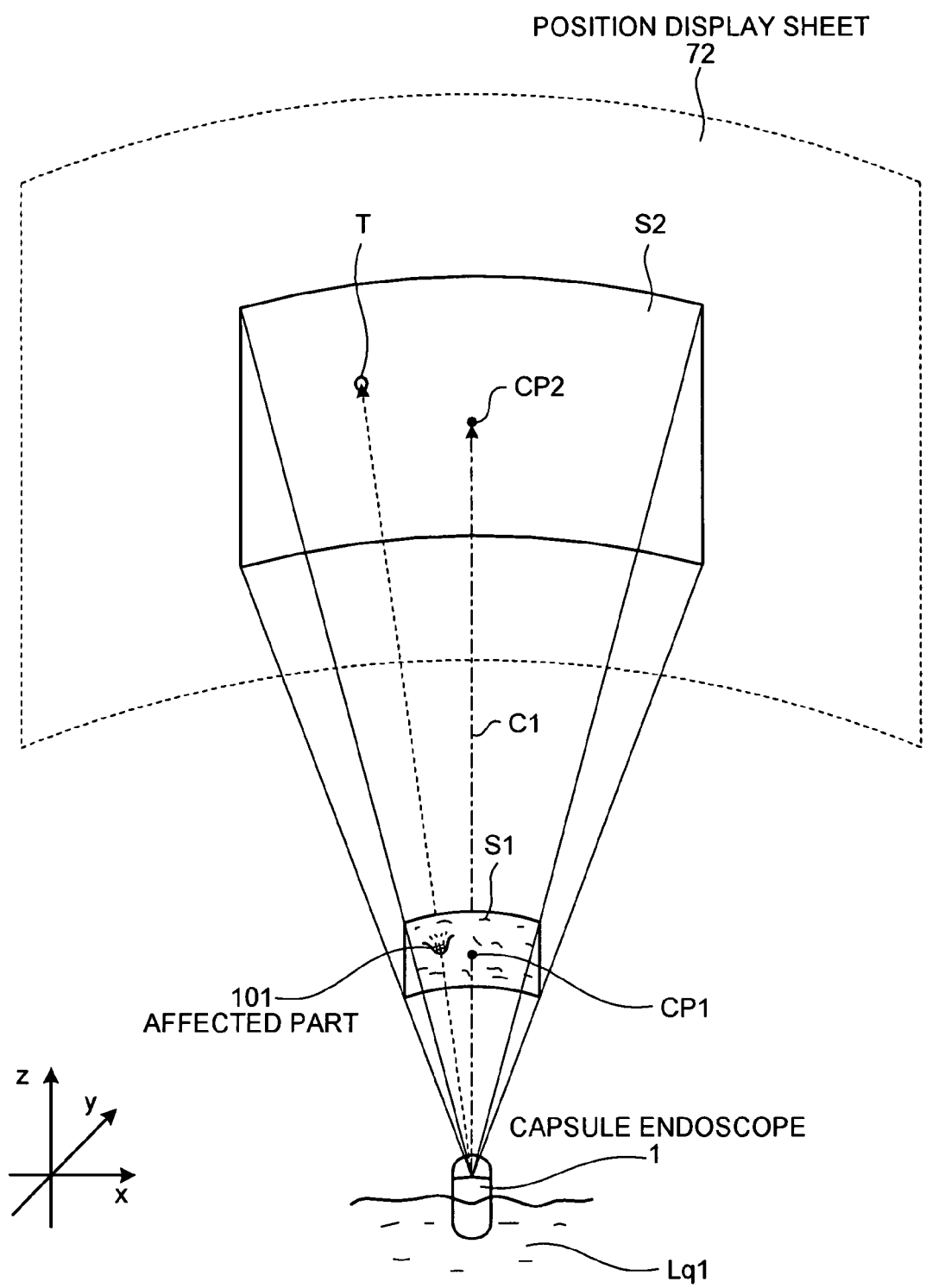
FIG. 26 is a schematic diagram explaining the operation of the control unit for specifying an approaching position corresponding to the designated position from a plurality of approaching positions on the position display sheet.

Operations of the control unit 89 to specify the approaching position corresponding to a designated position on the images of the inside of the stomach that are picked up by the capsule endoscope 1, which has been introduced into the stomach of the subject 100. FIG. 24 is a schematic diagram showing a state that the capsule endoscope 1 in the stomach is caught by a magnetic force of the permanent magnet 3 which is moved close to the approaching position on the position display sheet 72. FIG. 25 is a schematic diagram showing an image of the inside of the stomach picked up by the capsule endoscope 1 that is caught in the FIG. 24 state. FIG. 26 is a schematic diagram explaining the operation of the control unit 89 for specifying an approaching position corresponding to the specified position from a plurality of approaching positions on the position display sheet 72.

To start with, the examiner performs the steps S101 to S106 already described. The capsule endoscope 1, as shown in FIG. 24, for example, floats in the liquid Lq1 having been introduced into the stomach of the subject 100, and is caught by a magnetic field of the permanent magnet 3 having been moved close to a desired approaching position presented by the position display sheet 72. The thus caught capsule endoscope 1 successively picks up images of the inside of the stomach while changing one of the position and the posture thereof by the magnetic force of the permanent magnet 3. The capsule endoscope 1 picks up an image of an imaging region S1, for example. The imaging region S1 is a part of the stomach wall falling within the imaging field of the capsule endoscope 1, and includes an affected part 101. In this way, the capsule endoscope 1 picks up the image of the inside of the stomach, which includes the affected part 101 in the stomach. The image of the inside of the stomach is displayed by the display unit 7 of the workstation 89.

Subsequently, the examiner operates the input unit 6 to move a cursor K to a desired position of the image of the inside of the stomach displayed by the display unit 7, for example, a position of the affected part 101 thereby to designate a position of the affected part 101. The input unit 6 inputs designated position information for specifying the designated position of the affected part 101 to the control unit 89. When receiving the designated position information from the input unit 6, the control unit 89 specifies an approaching position corresponding to the position of the affected part 101 according to the positional relationship of the capsule endoscope 1 and the position display sheet 72 and the designated position information.

Specifically, the position/posture detecting unit 89f detects a positional relationship between the capsule endoscope 1 having picked up the image of the inside of the stomach and the position display sheet 72 worn by the subject 100. The position specifying part 89h detects a partial region S2 of the position display sheet 72 shown in FIG. 24 on the basis of the positional relationship between the capsule endoscope 1 and the position display sheet 72, which has been detected by the position/posture detecting unit position/posture detecting unit 89f. The partial region S2 is a part of the position display sheet 72, which is defined by the field angle of the capsule endoscope 1, and is formed by projecting the imaging region S1 from the capsule endoscope 1 in the stomach shown in FIG. 24 to the position display sheet 72. The imaging region S1 and the partial region S2 are substantially analogous in shape to each other.

The position specifying part 89h detects a relative positional relationship between the center of the image of the inside of the stomach and the designated position of the affected part 101 on the basis of the designated position information of the affected part 101 that is input from the input unit 6. The relative positional relationship between the center of the image and the designated position of the affected part 101 is substantially equal to the relative positional relationship between the center CP1 and the affected part 101 in the imaging region S1 shown in FIG. 26. The position specifying part 89h, as shown in FIG. 26, detects a center CP2 of the partial region S2 at the cross point of the partial region S2 and the major axis C1 on the basis of the positional relationship between the capsule endoscope 1 and the position display sheet 72. The major axis C1 corresponds to the center axis of the imaging field of the capsule endoscope 1, as described above. Therefore, the two centers CP1 and CP2 lie on the major axis C1.

The position specifying part 89h may specify an approaching position T corresponding to the designated position of the affected part 101 from the plurality of the approaching positions in the partial region S2, which is analogous to the imaging region S1 on the basis of the positional relationship between the capsule endoscope 1 and the position display sheet 72 and the designated position information of the affected part 101. The positional relationship of the center CP2 and the approaching position T in the partial region S2 is the substantially same as the relative positional relationship between the center CP1 and the affected part 101 in the imaging region S1. When the capsule endoscope 1 sets the center axis of the imaging field thereof to the affected part 101, the affected part 101 and the approaching position T lie on the major axis C1 of the capsule endoscope 1.

When the position specifying part 89h specifies the approaching position T corresponding to the designated position, the control unit 89 causes the display unit 7 to display information indicative of the approaching position T specified by the position specifying part 89h. In this case, the display control unit 9a causes the display unit 7 to display information indicating that the specified approaching position T corresponds to which of the approaching positions on the position display sheet 72. The examiner will easily find the approaching position T corresponding to the designated position of the affected part 101, for example, from the plurality of approaching positions on the position display sheet 72 on the basis of the information displayed by the display unit 7.

Figure 27:
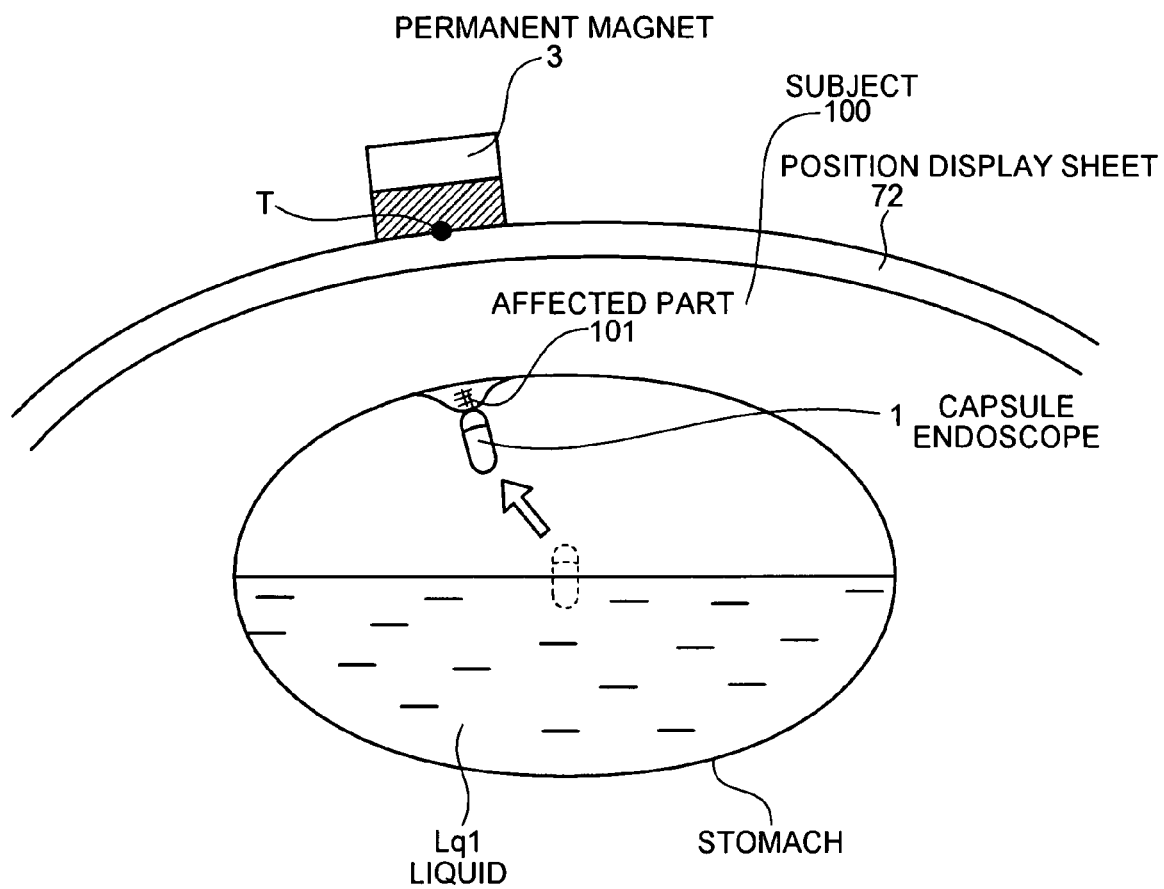
FIG. 27 is a schematic diagram showing a state that the capsule endoscope 1 is moved close to an affected part of the inside of the stomach.

Thereafter, the examiner moves the capsule endoscope 1 in the stomach close to the affected part 101 by moving the permanent magnet 3 to the approaching position T displayed by the display unit 7. FIG. 27 is a schematic diagram showing a state that the capsule endoscope 1 is moved close to the affected part 101 of the inside of the stomach. As shown in FIG. 27, the permanent magnet 3 having been moved close to the approaching position T corresponding to the designated position of the affected part 101 generates a magnetic field to the capsule endoscope 1 in the stomach, and attracts the capsule endoscope 1 to the affected part 101 by the magnetic force of the magnetic field. The permanent magnet 3 is selected from a plurality of permanent magnets available, and is capable of generating a magnetic field high enough to attract the capsule endoscope 1.

The capsule endoscope 1 to which the magnetic field of the permanent magnet 3 has been applied moves to and comes in contact with the affected part 101 and picks up an enlarged image of the affected part 101. The workstation 84 displays the enlarged view picked up by the capsule endoscope 1 on the display unit 7. The examiner views the enlarged image displayed by the display unit 7, and carefully observes the desired position in the digestive tract of the affected part 101 or the like.

The capsule endoscope 1, which comes in contact with the inner wall of the digestive tract, may be designed such that it further include specially designed observing function, which picks up images by emitting special light, e.g., infrared light, and picks up an enlarged image of the desired position of the affected part 101 by the special light. In this case, the capsule endoscope having the additional special-light based observing function switches the observation light between the visible light by a LED, for example, and the special light according to the control signal issued from the workstation 84. The capsule endoscope 1 may have a sampling function to sample a body fluid or a biotissue by using a medial sampling needle, which is extensible from the casing. When coming in contact with the inner wall of the digestive tract, for example, the capsule endoscope 1 having such a sampling function samples a body liquid or a biotissue in the digestive tract according to a control signal from the workstation 84.

The capsule endoscope 1 may have a medical treatment function. Examples of the medial treatment functions are to cauterize a biotissue by a heating probe, which is extensible from the casing, to disperse chemicals into the digestive tract, and to inject chemicals into the affected part by using a needle, which is extensible from the casing. In this case, the capsule endoscope 1 additionally having the medical treatment function starts the medical treatment in response to a control signal issued from the workstation 84 when the capsule endoscope comes in contact with the inner wall of the digestive tract.

A chemical or biochemical sensor for medical treatment may be added to the capsule endoscope 1. In use, the chemical or biochemical sensor of the capsule endoscope 1 is brought into close contact with the biotissue in the digestive tract to judge whether the biotissue is a lesioned part or not. Thus, the capsule endoscope 1 additionally having the chemical or biochemical sensor is capable of detecting the lesioned part of the biotissue in the digestive tract.

In the fourth embodiment mentioned above, the display unit 7 visually presents the information indicating the approaching position specified on the basis of the desired designated position in the image. In connection with this, the following alternative is allowed within the scope of the invention. Suitable light emitting devices such as LEDs or organic EL devices are respectively located at the plurality of approaching positions on the position display sheet 72. When the position specifying part 89h specifies the approaching position corresponding to the designated position in those approaching positions on the position display sheet, the control unit 89 responsively drives the light emitting device of the specified approaching position to distinctively and visually present the approaching position to the examiner. The light emitting devices located on the position display sheet 72 are electrically connected to the control unit 89 via a cable or the like, and is controlled by the control unit 89.

In the fourth embodiment, the cross points of the vertical lines and the horizontal lines, which are formed on the position display sheet 72, are representative of the plurality of the approaching positions. However, the invention is not limited to this. In an alternative, the open spaces formed when those vertical and horizontal lines cross may represent the plurality of the approaching positions. In another alternative, a plurality of markers is formed on the position display sheet 72 and those markers represent the approaching positions, as in the first embodiment.

As described above, in the fourth embodiment of the invention, like the first embodiment, the position display sheet worn by the subject presents the plurality of approaching positions. Further, when a desired position of the images in the digestive tract, which are imaged by the capsule endoscope having been introduced into the subject, is designated, the approaching position corresponding to the designated position is specified from the plurality of the approaching positions on the position display sheet, and the specified approaching position is presented. Therefore, when the permanent magnet, for example, is moved close to the specified approaching position, the capsule endoscope is easily brought close to and into contact with the designated position (e.g., affected part) in the digestive tract with the aid of the attraction force by the permanent magnet. The result is to cause the capsule endoscope to pick up an enlarge image of the designated position, e.g., the affected part, of the inside of the digestive tract, to produce the useful effects of the first embodiment, and to observe the details of the insides of the subject through the viewing of the enlarged image of the desired position in the digestive tract.

Figure 28:
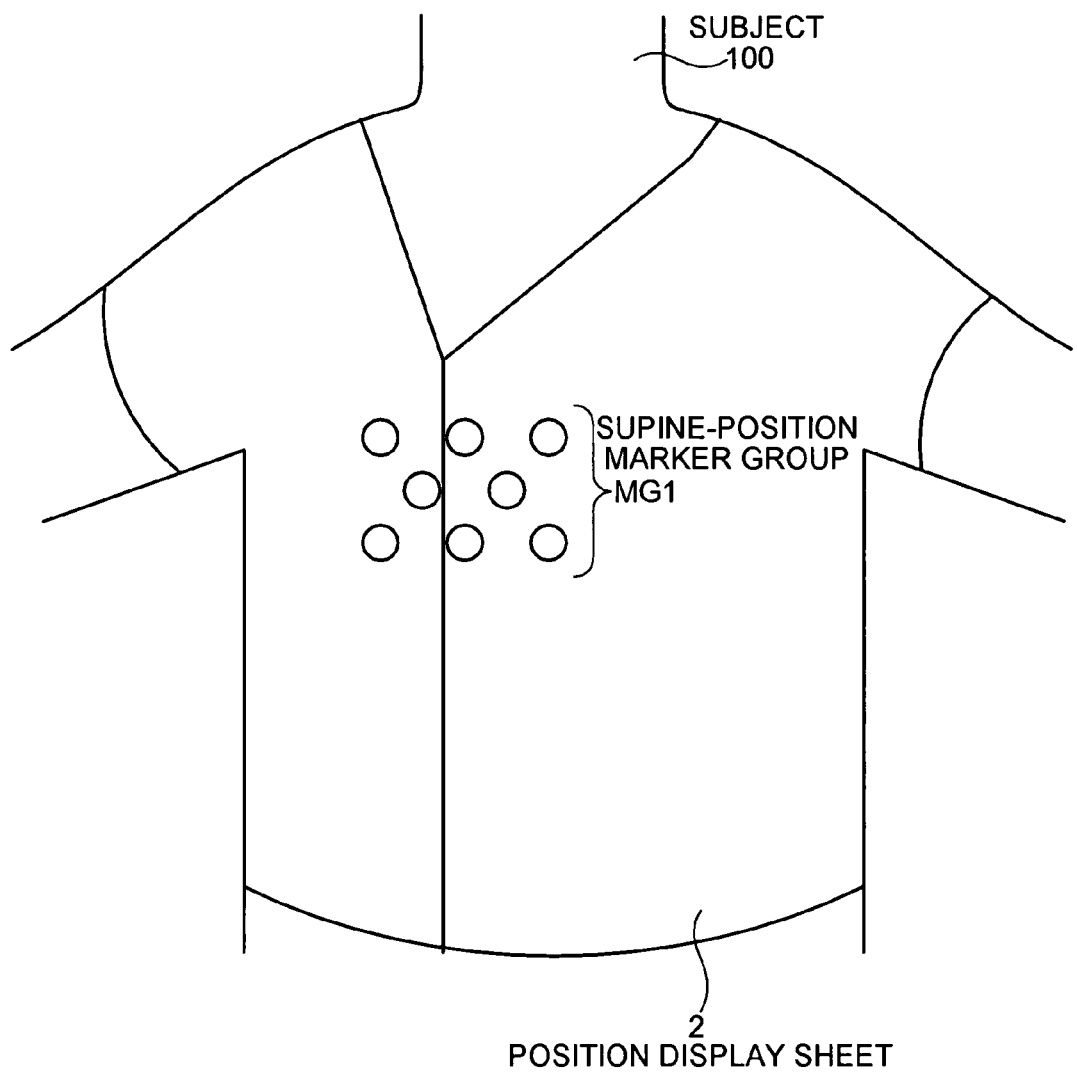
FIG. 28 is a schematic diagram showing a position display sheet of the wearing type.
Figure 29:
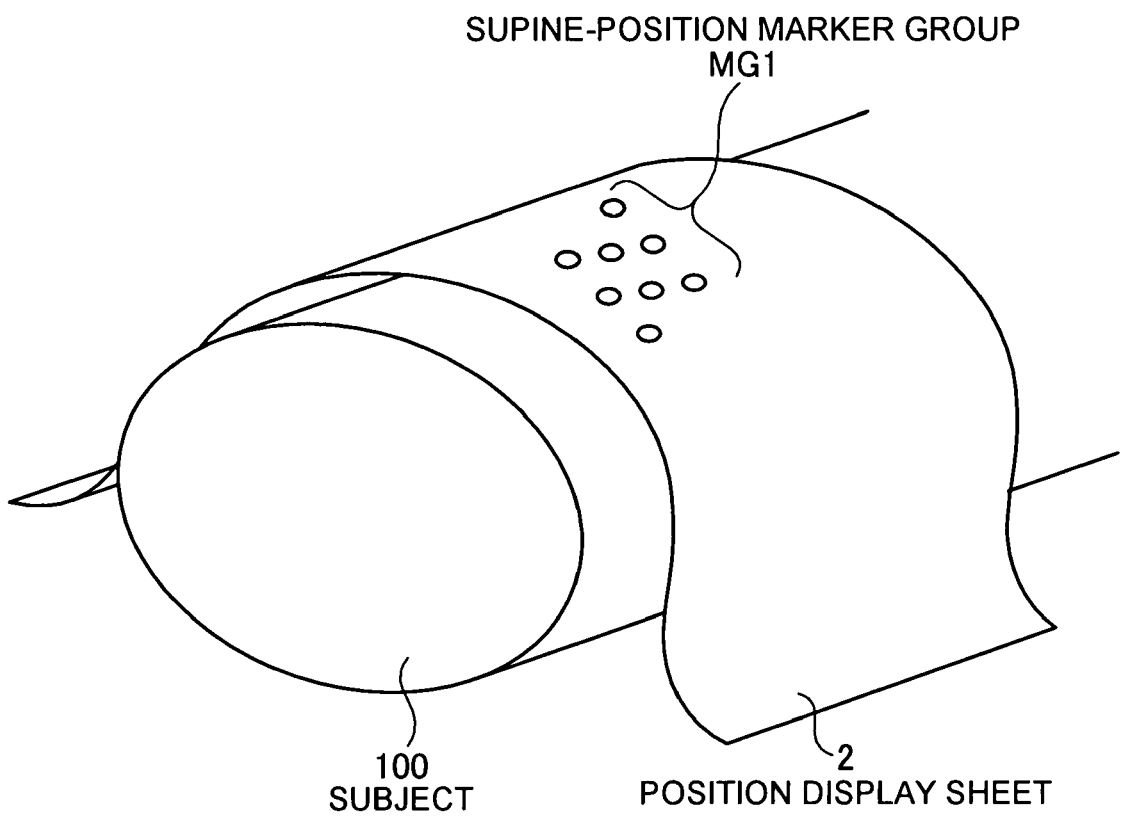
FIG. 29 is a schematic diagram showing a position display sheet of the sheet type.

In the first to the fourth embodiments, the position display sheet is of the type in which the position display sheet is wound around the trunk. It is evident that other types of position display sheets may be used for the present invention. A first example of such is of the wearing type as shown in FIG. 28. The position display sheet of this type is formed like clothing as shown in FIG. 29. In use, it is put on the trunk of the subject 100 as shown in FIG. 29. The position display sheet 2 of the wearing type or the sheet type, like the position display sheet of the winding type, may visually present the approaching positions by using the markers of the supine-position marker group MG1.

Figure 30:
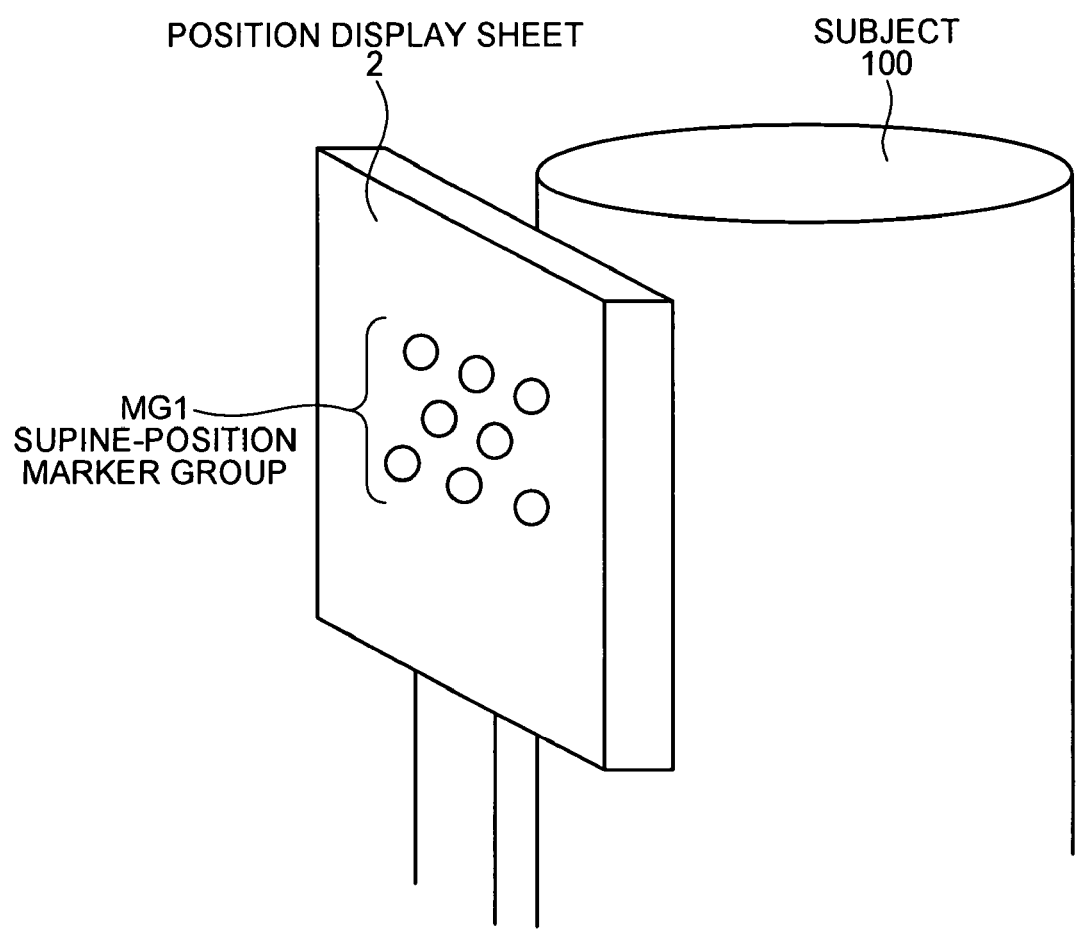
FIG. 30 is a schematic diagram showing a position display sheet of the plate type.
Figure 31:
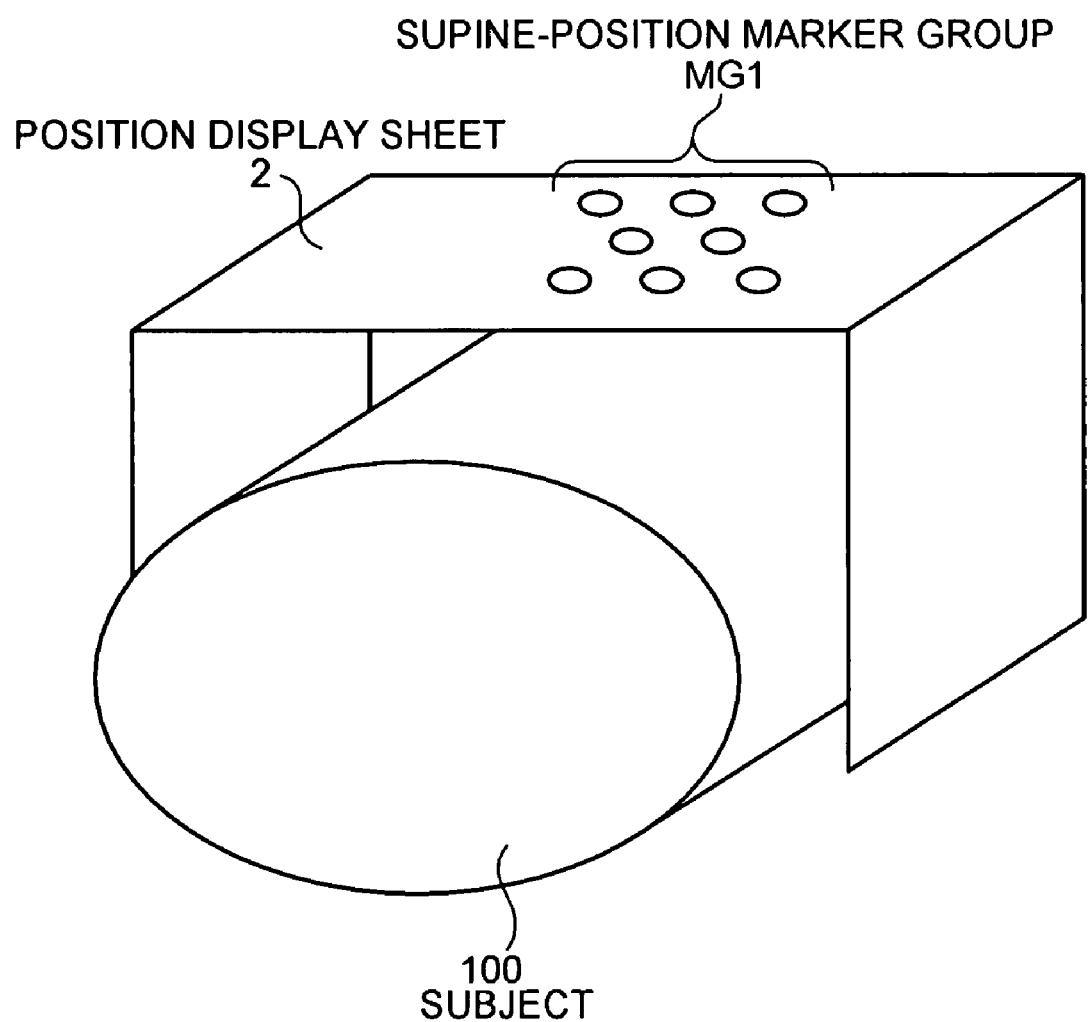
FIG. 31 is a schematic diagram showing a position display sheet of the frame type.

An additional example of the position display sheet is of the plate type as shown in FIG. 30. As shown, the markers of the supine-position marker group MG1 are formed on a high light-transmission plate such as a substantially transparent glass or resin plate. An additional example of the position display sheet 2 is of the frame type as shown in FIG. 31. A substantially transparent glass or resin plate is shaped like a U-shaped frame. The markers of the supine-position marker group MG1 are formed on the surface of the plate, as shown. The examiner views the subject 100 through the position display sheet 2 of the plate or frame type. The permanent magnet is moved close to any of the positions (i.e., approaching positions) on the subject 100 where the markers formed on the position display sheet 2 of the plate or frame type are projected.

With regard to those position display sheets of the winding, wearing, sheet, plate and frame types, it is desirable that a plurality of position display sheets are provided available for each physique of the subject (patient), and that the position display sheet is selected in accordance with the physique from those ones. The position display sheet that is selected in accordance with the physique of the patient exactly presents the approaching position on the body surface of the patient. Therefore, the examiner efficiently observes (examines) the insides of the patients of different physiques.

Figure 32:
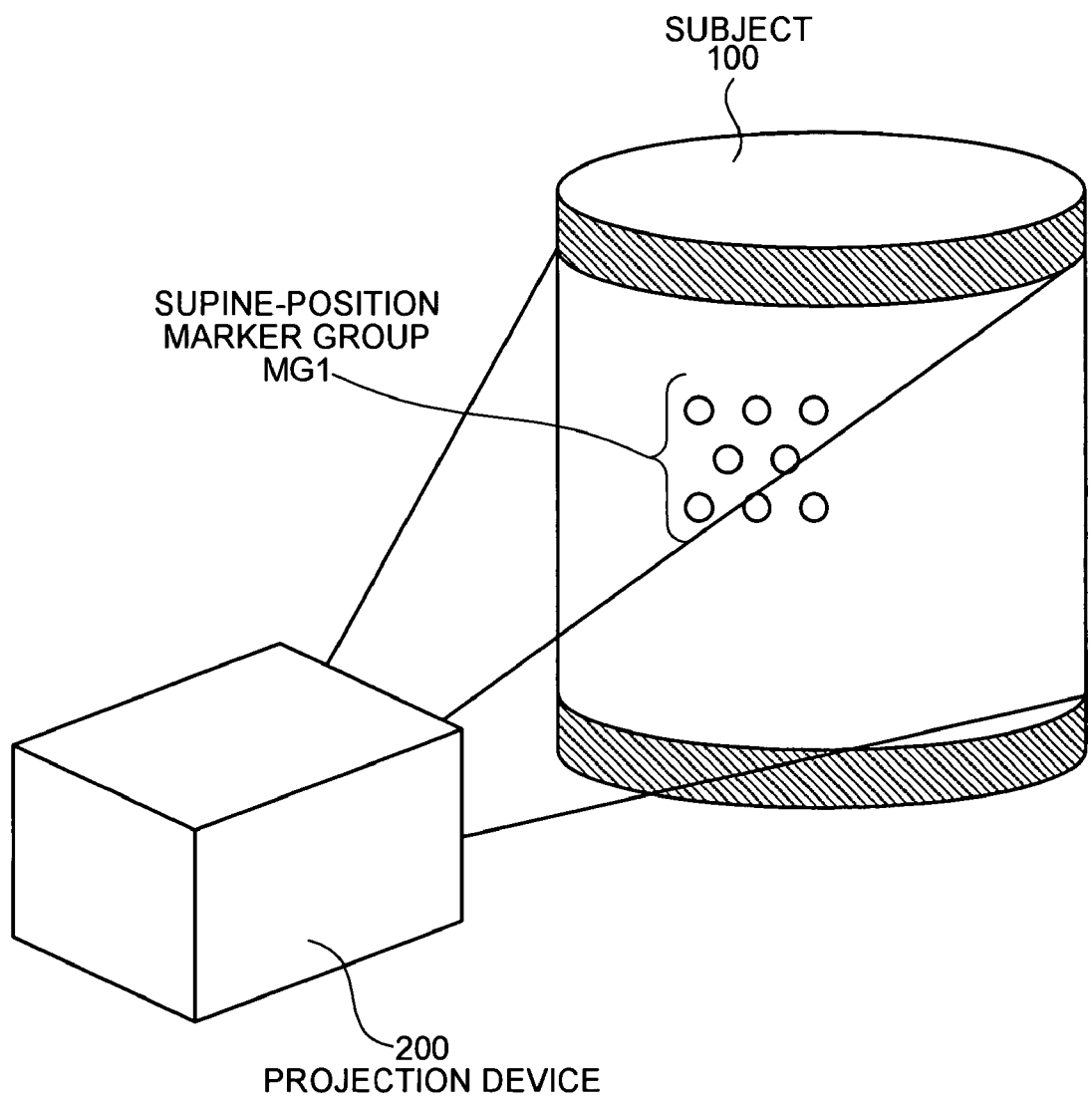
FIG. 32 is a schematic diagram showing a projection device for projecting information indicative of the approaching position to the subject.

In the first to the fourth embodiments, the position display sheet of a sheet-like member is attached to the subject. However, the invention is not limited to this. Alternatively, information indicating the approaching positions, such as markers, may be projected onto the subject. In this case, a projection device 200 for projecting the information representative of the approaching positions, in place of the position display sheet, is incorporated into the body-insertable device system, as shown in FIG. 32. The projection device 200 functions as a position presenting unit for presenting the approaching positions, and projects the markers of the supine-position marker group MG1, for example, onto the subject 100 to visually present the approaching positions to the subject 100. What the examiner has to do to observe the subject 100 is to merely move the permanent magnet to the marker projected onto the subject 100 by the projection device 200.

The projection device 200 generates projection information to project the in-vivio image onto the subject on the basis of in-vivio image information of each subject, picked up by CT, MRI or the like, and projects the in-vivio image onto the subject by using the projection image. In this case, the projection device 200 presents the approaching positions that the permanent magnet approaches by using the in-vivio image projected onto the subject. Accordingly, the examiner exactly knows the information of the insides of the subject. The examiner easily operates the magnet which changes at least one of the position and the posture of the capsule endoscope in the digestive tract by its magnetic force. Further, the examiner easily causes the capsule endoscope to pick up the image at a desired position in the digestive tract of the patient or the like, and more accurately diagnoses the subject.

Figure 33:
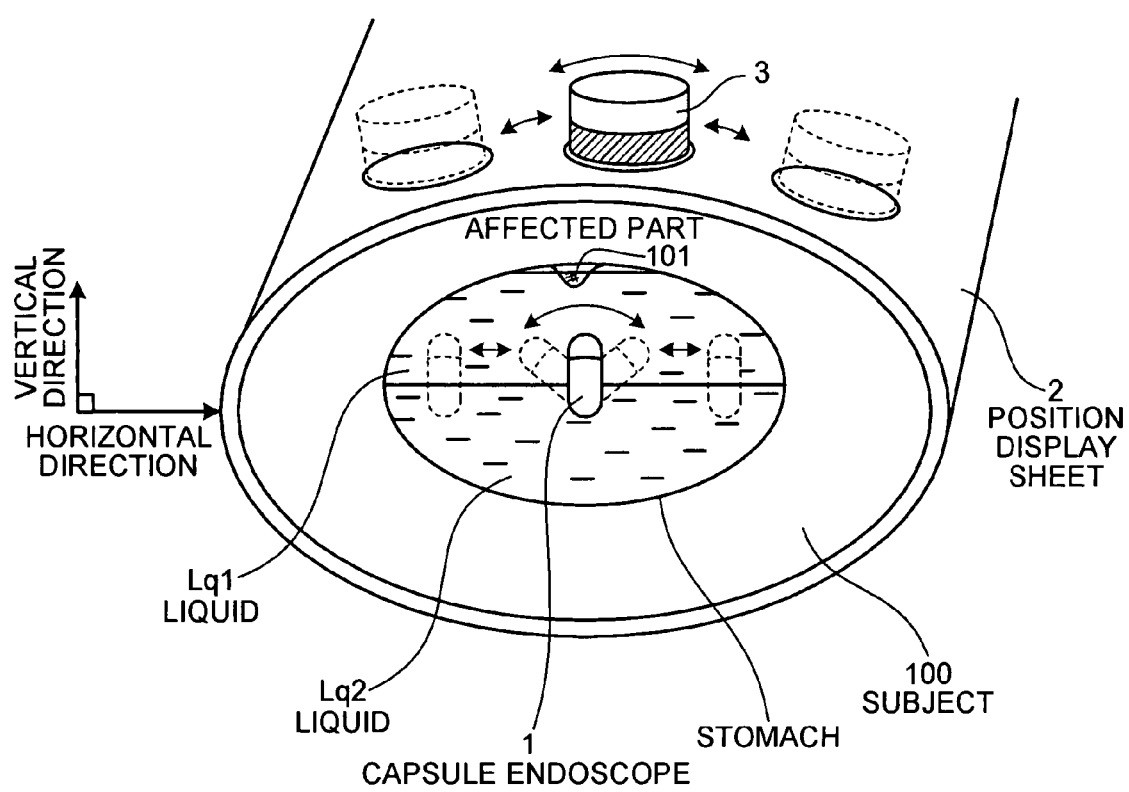
FIG. 33 is a schematic diagram showing a state that the capsule endoscope floats to the surface of two kinds of liquids having been introduced into the digestive tract.

In the first to the fourth embodiments of the invention, one kind of liquid Lq1 is introduced into the digestive tract of the subject, and the capsule endoscope floats in the liquid Lq1. However, the invention is not limited to this. Alternatively, two kinds of liquids may be introduced into the digestive tract of the subject, and the capsule endoscope floats in the vicinity of the interface of those liquids. In this case, the specific gravities of those liquids Lq1 and Lq2 introduce into the subject are different from each other. A specific gravity of the liquid Lq1, as described above, is almost equal to or smaller than that of the capsule endoscope 1. A specific gravity of the liquid Lq2 is larger than that of the capsule endoscope 1. When the liquids Lq1 an Lq2 have been introduced into the subject 100, as shown in FIG. 33, the capsule endoscope 1 floats in the vicinity of the interface of the liquids Lq1 an Lq2 in the stomach of the subject 100. The capsule endoscope 1 floating in the vicinity of the interface, as in the case of the first embodiment, changes one of the position and the posture thereof by the magnetic field of the permanent magnet 3 having been moved close to the approaching position.

Figure 34:
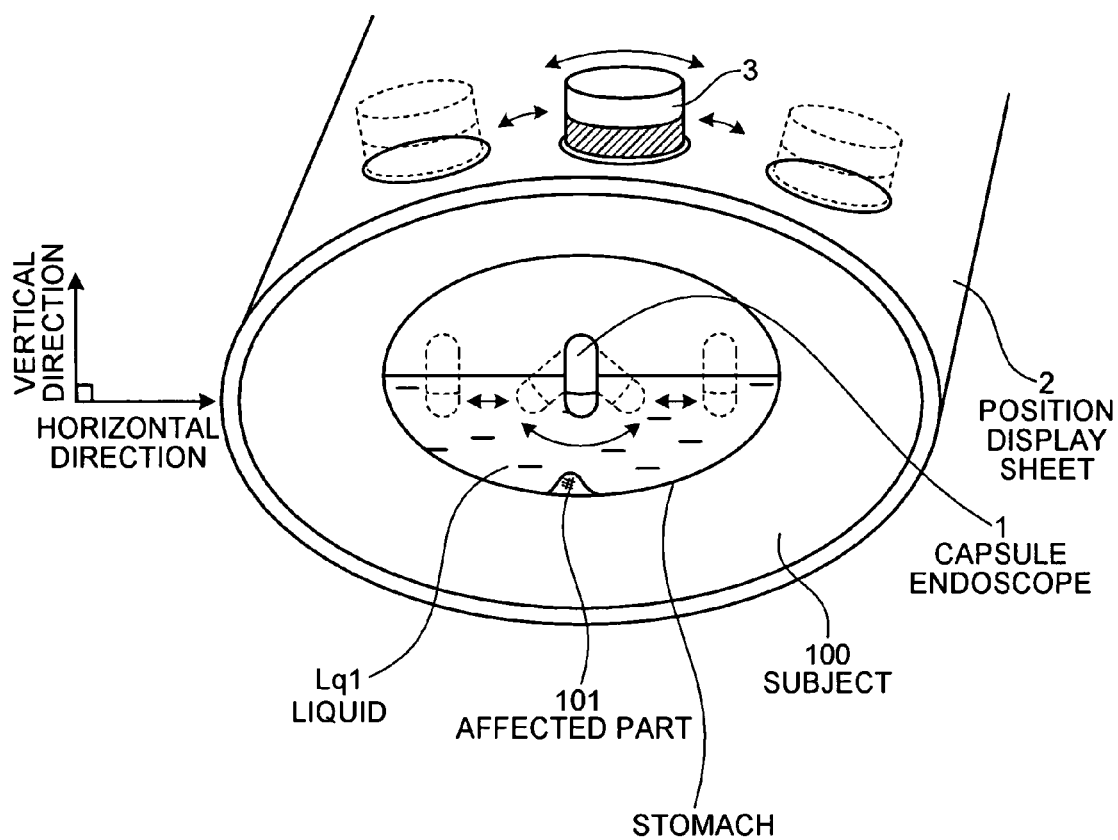
FIG. 34 is a schematic diagram showing a state that the capsule endoscope having the gravity center located at the front end of the casing has been introduced into the digestive tract.

In the first to the fourth embodiments, a gravity of the capsule endoscope 1 is located at the rear end of the casing, the capsule endoscope 1 floating in the liquid Lq1 in the digestive tract directs its imaging field upward in the vertical direction with respect to the liquid surface of the liquid Lq1. However, the invention is not limited to this. If required, the capsule endoscope 1 floating in the liquid Lq1 in the digestive tract may direct its imaging field downward in the vertical direction with respect to the liquid surface of the liquid Lq1. In this case, the gravity of the capsule endoscope 1 is located at the front end of the casing. The capsule endoscope 1 thus constructed, as shown in FIG. 34, floats in the liquid Lq1 in the stomach of the subject 100 and directs its imaging field downward in the vertical direction with respect to the liquid surface of the liquid Lq1. The capsule endoscope 1 directing its imaging field downward in the vertical direction changes at least one of the position and the posture thereof by the magnetic of the permanent magnet 3 having been moved close to the approaching position, for example. The capsule endoscope 1 picks up the inside of the stomach having been expanded by the liquid Lq1 through the liquid Lq1. Accordingly, the examiner clearly picks up an image of the details of the inside of the stomach without expanding the biotissue by using the foaming agent.

Figure 35:
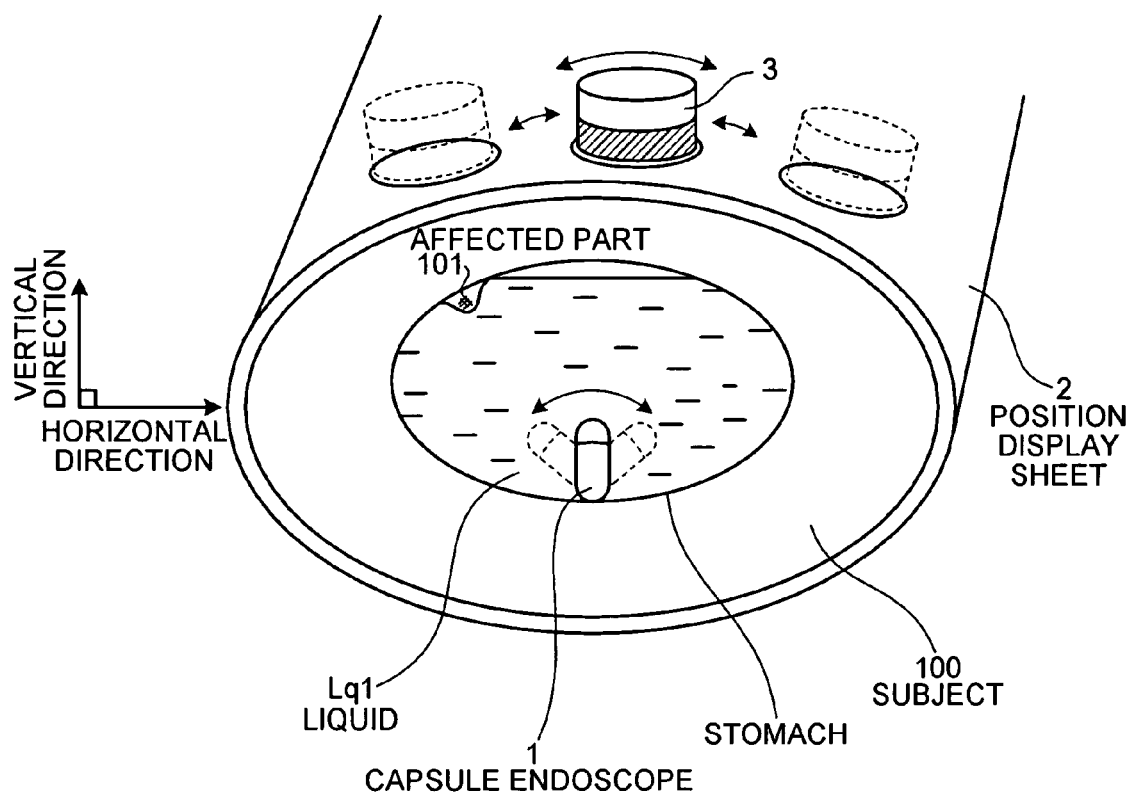
FIG. 35 is a schematic diagram showing a capsule endoscope having a larger specific gravity than that of the liquid in the digestive tract when it is introduced into the digestive tract.

While in the first to the fourth embodiments, the capsule endoscope floats in the liquid having been introduced into the subject, the invention is not limited to this. The capsule endoscope may be sunk in the liquid having been introduced into the digestive tract of the subject. Specifically, the capsule endoscope 1 is designed to have a larger specific gravity than that of the liquid Lq1 by adding a weight to the capsule endoscope or reducing the inner space to increase a density thereof. In this case, the gravity center of the capsule endoscope 1 is located at the rear end of the casing. The capsule endoscope 1 so designed, as shown in FIG. 35, sinks in the liquid Lq1 in the stomach of the subject 100, and directs its imaging field upward in the vertical direction with respect to the liquid surface of the liquid Lq1. The capsule endoscope 1 directing its imaging field upward in the vertical direction changes at least one of the position and the posture thereof by the magnetic force of the permanent magnet 3 having been moved close to the approaching position, for example. The capsule endoscope 1 picks up the inside of the stomach having been expanded by the liquid Lq1 through the liquid Lq1. Accordingly, the examiner clearly picks up an image of the details of the inside of the stomach without expanding the biotissue by using the foaming agent. A foam agent and a small amount of water, in place of the liquid Lq1, may be used for expanding the stomach, not shown. In this case, the subject easily takes in the foaming agent and water since the stomach is expanded by using small amounts of foaming agent and water. In the case of FIG. 35, the orientation of the capsule endoscope 1 is changed by changing the position of the permanent magnet 3. Alternatively, the orientation of the capsule endoscope 1 may be changed by changing the orientation, not the position, of the permanent magnet 3. At this time, the orientation of the permanent magnet 3 may be designated by markers or the like that are formed on the position display sheet 2. In this case, there is no need of changing the position of the permanent magnet. Accordingly, the operability is enhanced.

In the third and the fourth embodiments, the magnetic field of the permanent magnet is used for changing at least one of the position and the posture of the capsule endoscope in the digestive tract. However, the invention is not limited to this. In an alternative, an electromagnet, in place of the permanent magnet, is moved close to the approaching position and is used for changing at least one of the position and the posture of the capsule endoscope in the digestive tract by the magnetic field of the electromagnet. In this case, the body-insertable device system is constructed by combining the second and the third embodiments or the second and the fourth embodiments.

In the first and the fourth embodiments, the workstation directly receives the image signal from the capsule endoscope via the antenna combined to the workstation. However, the invention is not limited to this. If required, a given receiver may be used which receives and stores the image signal from the capsule endoscope via an antenna located on the body surface of the subject. The workstation receives the image signal that is stored by the receiver. A portable type recording medium, for example, may be used for transferring the information between the receiver and the workstation.

In the first and the fourth embodiments, the acceleration and angular velocity sensors are used as means for detecting the position and the posture of the capsule endoscope having been introduced into the subject. However, the invention is not limited to this. As the means for detecting the position and the posture of the capsule endoscope, a tomogram image obtained through the scanning by supersonic wave may be used for detecting the position and the posture of the capsule endoscope. The position and the posture of the capsule endoscope in the digestive tract may also be detected in a manner that the ultrasonic wave is radiated from a predetermined position to the capsule endoscope in the subject, and the position and the posture of the capsule endoscope are detected on the basis of a strength of the ultrasonic wave detected by the capsule endoscope. Further, the position and the posture of the capsule endoscope in the digestive tract may be detected in a manner that a magnetic field is generated from the outside of the subject toward the capsule endoscope, and the position and the posture of the capsule endoscope are detected on the basis of a strength of the magnetic field detected by the capsule endoscope. Additionally, the position and the posture of the capsule endoscope in the digestive tract may be detected in a manner that a magnetic field generated from the capsule endoscope in the subject is detected and the position and the posture of the capsule endoscope are detected on the basis of a strength of the magnetic field detected by the capsule endoscope.

In the first to the fourth embodiments, the acceleration sensor is used for detecting the position of the capsule endoscope, and the angular velocity sensor is used for detecting the posture (direction of the major axis C1) of the capsule endoscope. However, the invention is not limited to this. Alternatively, oscillation coils for generating an alternating magnetic field may be used for magnetically detecting the position and the posture of the capsule endoscope.

Figure 36:
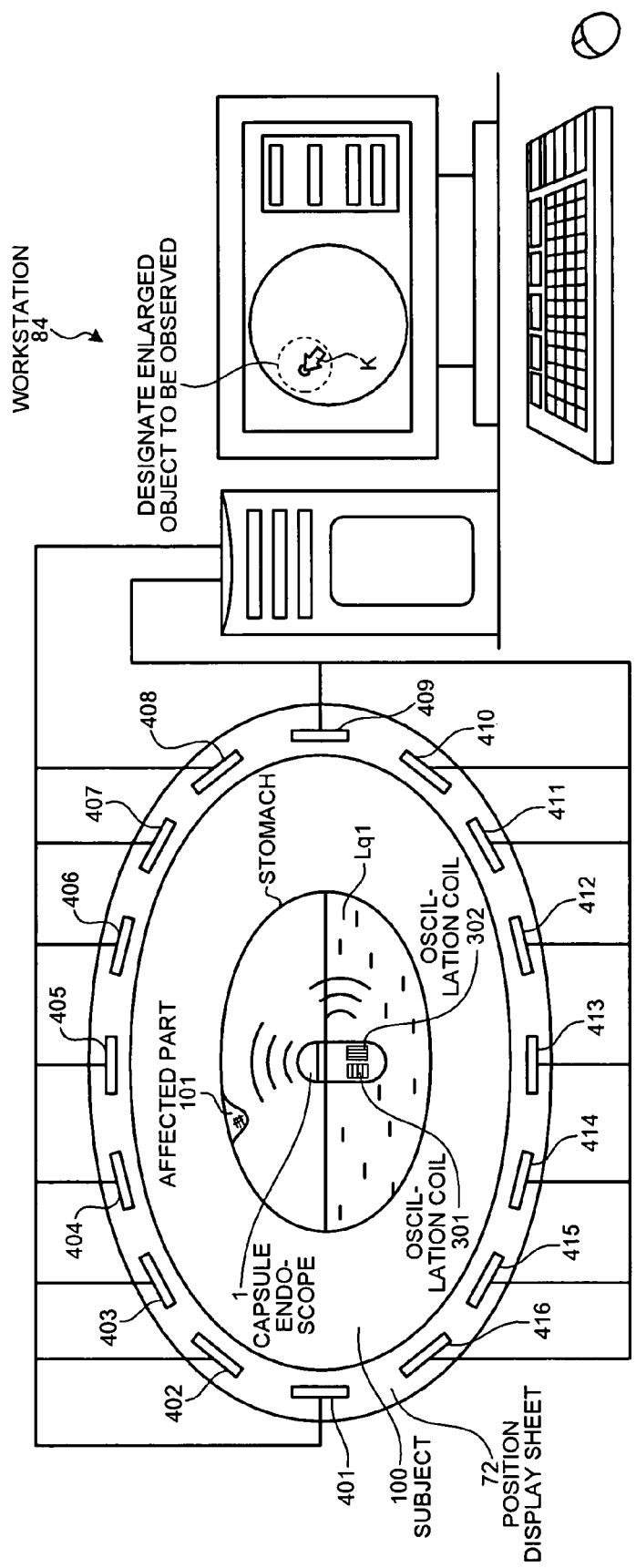
FIG. 36 is a schematic diagram showing a configuration example of a body-insertable device system which is a modification of the fourth embodiment of the invention.

In the modification of the body-insertable device system of the fourth embodiment, as shown in FIG. 36, a capsule endoscope 1 has two oscillation coils 301 and 302 for generating alternating magnetic fields in the direction orthogonal to the body outside, a plurality of detecting coils 401 to 416 for detecting the alternating magnetic fields generated from the oscillation coils 301 and 302, a position display sheet 72, and a workstation 84. The number of the detecting coils is not limited to 16. Use of a plural number of detecting coils suffices for the requirement in the invention. While the detecting coils 401 to 416, as shown in FIG. 36, are located at positions inside the position display sheet 72, those may be located at positions outside the position display sheet 72 and near the body surface of the subject 100.

The oscillation coil 301 generates an alternating magnetic field in the direction of the major axis C1 under control of the control unit 18 of the capsule endoscope 1. The oscillation coil 302 generates an alternating magnetic field in the direction (direction of the diameter axis C2a) vertical to the major axis C1 under control of the control unit 18 of the capsule endoscope 1. The detecting coils 401 to 416 are located inside the position display sheet 72, for example, and connected to the workstation 84 via a cable or the like. The detecting coils 401 to 416 detect the alternating magnetic field generated by the oscillation coils 301 and 302 of the capsule endoscope 1 and send the detection result to the workstation 84. The position/posture detecting unit 89f of the workstation 84 calculates the position and the posture of each of the oscillation coils 301 and 302 with respect to the position display sheet 72 on the basis of the detection result of the alternating magnetic field (e.g., current corresponding to the intensity of the alternating magnetic field), and detects the position and the posture of the capsule endoscope 1 in the stomach of the subject 100 on the basis of the calculation result.

Figure 37:
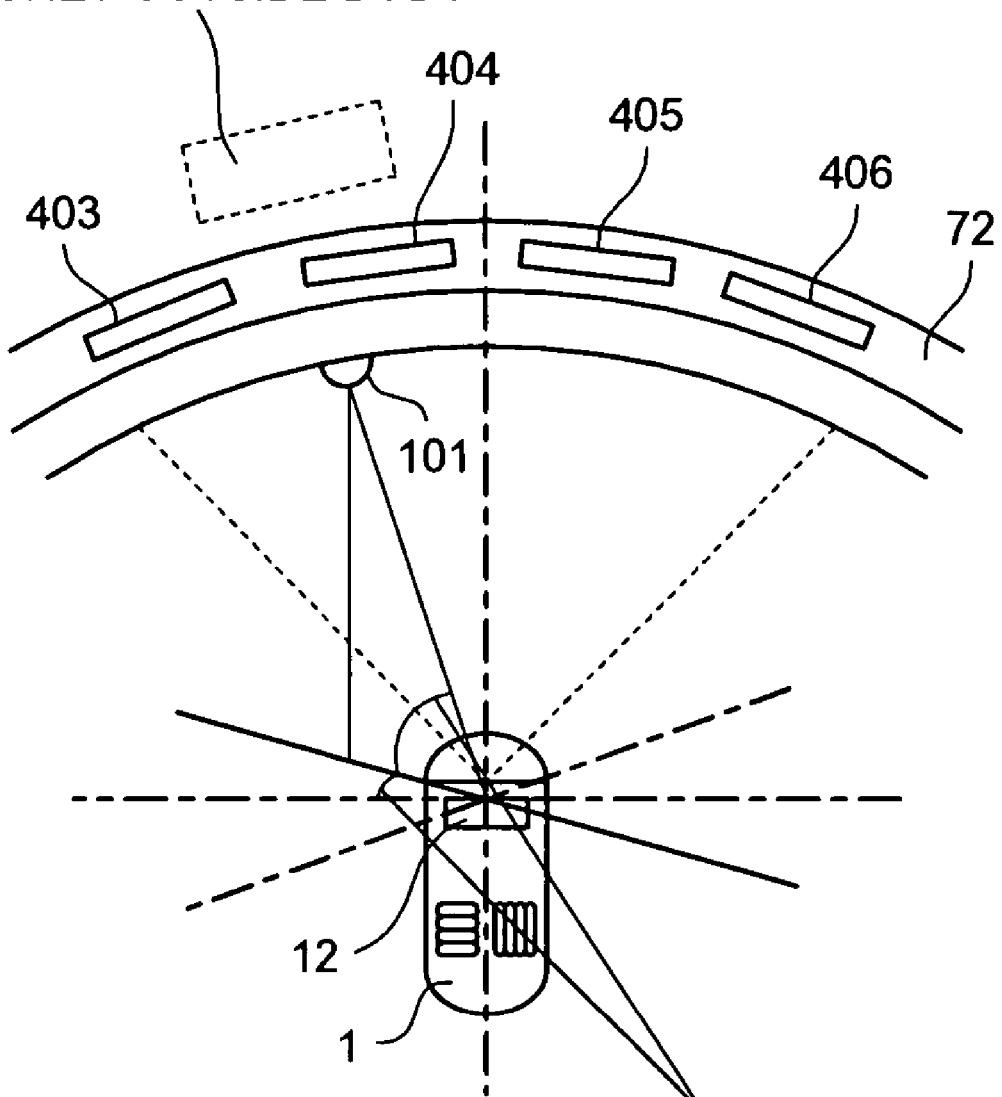
FIG. 37 is a schematic diagram showing a shortest enlargement observation direction for the imaging element.

To observe the affected part 101 of the stomach in an enlarged manner, the examiner places the cursor K at a position to be observed in the enlarged manner (the image position of the affected part 101) and selects this position on the basis of the image displayed by the display unit 7 of the workstation 84. In this case, the input unit 6 inputs designated position information corresponding to the image position of the affected part 101 to the control unit 89. The position specifying part 89h of the control unit 89 calculates in which direction with respect to the imaging unit 12 of the capsule endoscope 1 the designated position (affected part 101) is present on the basis of the input designated position information and the image. In this case, the position specifying part 89h, as shown in FIG. 37, calculates a direction (shortest enlargement observation direction for the imaging element), which provides the shortest distance in connecting the imaging unit 12 of the capsule endoscope 1 to the affected part 101. The position specifying part 89h calculates an approaching position that the permanent magnet 3 approaches on the position display sheet 72 on the basis of the positions and the postures (i.e., the position and the posture of the capsule endoscope 1) of the oscillation coils 301 and 302 detected by the position/posture detecting unit position/posture detecting unit 89f, a positional relationship between the oscillation coils 301 and 302, and the shortest enlargement observation direction for the imaging element, and specifies the approaching position corresponding to the affected part 101 from the plurality of approaching positions on the position display sheet 72.

In the first and the fourth embodiments, the permanent magnet is located in the casing of the capsule endoscope. However, the invention is not limited to this. To control at least one of the position and the posture of the capsule endoscope by the magnetic field, it suffices that a magnetic material is present in the casing of the capsule endoscope. In this case, the magnetic material may be a ferromagnetic material, an electrical component, e.g., a battery, or an electromagnet.

The examiner easily picks up a series of images over a desired region in a desired digestive tract without such troublesome examination work that the examiner successively knows the imaging field of the capsule endoscope to the inside of the digestive tract on the basis of the images displayed on the display. Therefore, the present invention successfully provides a body-insertable device system which easily acquires the images necessary for observing the inside of a desired digestive tract in a short time.

It should be understood that further useful effects and modifications of the invention will be readily deduced from the foregoing descriptions by those skilled persons in the field, that the present invention is not limited to the embodiments stated above, and that the invention may be modified, altered and changed within the scope of the appended claims and within the equivalents of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

The body-insertable device system and a body-insertable device guiding method, which are constructed according to the present invention, are useful for picking up images of the inside of a digestive tract by the body-insertable device, such as a capsule endoscope, having been introduced into the digestive tract of a subject. Particularly, the examiner easily picks up a series of images over a desired region in a desired digestive tract without such troublesome examination work that the examiner successively knows the imaging field of the body-insertable device to the inside of the digestive tract on the basis of the images displayed on the display. Therefore, the present invention is suitable for a body-insertable device system, which easily acquire the images necessary for observing the inside of a desired digestive tract in a short time, and a method of guiding the body-insertable device system.

What is claimed is:

1. A body-insertable device system comprising:
a body-insertable device comprising:
an imaging unit which picks up images of an inside of a subject, and
a magnetic material;
a magnetic field generating unit configured to generate a magnetic field to the magnetic material of the body-insertable device having been introduced into the subject and to change at least one of a position and a posture of the body-insertable device by the magnetic field; and
a position presenting unit configured to visually present a plurality of approaching positions, on or near a body surface of the subject, for placing the magnetic field generating unit.

2. The body-insertable device system according to claim 1, wherein the position presenting unit presents a plurality of the approaching positions.

3. The body-insertable device system according to claim 1, wherein the position presenting unit presents an approaching position of the magnetic field generating unit based on a posture of the subject.

4. The body-insertable device system according to claim 1, wherein the position presenting unit presents a posture of the magnetic field generating unit when the magnetic field generating unit is moved close to the subject.

5. The body-insertable device system according to claim 1, wherein the magnetic field generating unit includes a magnetic-field intensity control unit which controls an intensity of a magnetic field generated thereby, the position presenting unit associates the approaching positions with an intensity of a magnetic field generated by the magnetic field generating unit, and the magnetic-field intensity control unit controls an intensity of a magnetic field generated by the magnetic field generating unit according to a magnetic-field intensity visually presented by the position presenting unit.

6. The body-insertable device system according to claim 5, wherein the magnetic field generating unit includes an electromagnet for generating the magnetic field, and a power control unit which controls current applied to the electromagnet.

7. The body-insertable device system according to claim 5, wherein the magnetic field generating unit includes a permanent magnet for generating the magnetic field, and a distance changing unit which changes a distance between the permanent magnet and the subject.

8. The body-insertable device system according to claim 5, wherein the magnetic field generating unit includes a plurality of permanent magnets.

9. The body-insertable device system according to claim 8, further comprising a housing which houses the plurality of permanent magnets.

10. The body-insertable device system according to claim 9, wherein the housing includes a plurality of housing sections which house the plurality of permanent magnets respectively; a plurality of confining units which are respectively provided on the plurality of housing sections and confine the plurality of permanent magnets in the plurality of housing sections; a plurality of permanent-magnet detecting units which are respectively provided on the plurality of housing sections and detect whether or not the plurality of permanent magnets are held in the plurality of housing sections; and a control unit which controls the plurality of confining units so as to selectively keep the plurality of permanent magnets in a confined state or a non-confined state on the basis of the detection result of the plurality of permanent-magnet detecting units.

11. The body-insertable device system according to claim 10, wherein when each of the plurality of permanent-magnet detecting units detects the corresponding permanent magnet, the control unit controls the confining units so as to confine the permanent magnets held in the housing sections.

12. The body-insertable device system according to claim 11, wherein when the detection result is changed from a detection result that the permanent magnets are not present in the housing sections to another detection result that the permanent magnets are present in the housing sections, the control unit controls the confining units so as to confine the permanent magnets held in the housing sections.

13. The body-insertable device system according to claim 10, wherein when the plurality of permanent-magnet detecting units detect all of the plurality of permanent magnets present in the plurality of housing sections, the control unit controls the plurality of confining units so as to release one of the plurality of permanent magnets confined in the plurality of housing sections from the confined state thereof.

14. The body-insertable device system according to claim 13, wherein the housing further includes a permanent-magnet selecting unit which selects one of the plurality of permanent magnets held in the plurality of housing sections, and the control unit controls the plurality of confining units so as to release permanent magnets selected by the permanent-magnet selecting unit from the confined state thereof.

15. The body-insertable device system according to claim 14, wherein the permanent-magnet selecting unit selects the permanent magnet according to an intensity of a magnetic field indicated by the position presenting unit.

16. The body-insertable device system according to claim 1, wherein the magnetic field generating unit includes a magnetic-field intensity control unit which controls an intensity of a magnetic field generated by the magnetic field generating unit, the position presenting unit presents an intensity of a magnetic field generated by the magnetic field generating unit according to a body shape of the subject, and the magnetic-field intensity control unit controls an intensity of a magnetic field generated by the magnetic field generating unit according to a magnetic-field intensity visually presented by the position presenting unit.

17. The body-insertable device system according to claim 1, wherein the position presenting unit includes a reference part which is located near the subject and which shows a position near the subject, and an indicating part which indicates a position near the magnetic field generating unit to the reference part.

18. The body-insertable device system according to claim 17, wherein the body-insertable device includes a transmission antenna which wirelessly transmits an image acquired by the imaging unit to outside the body-insertable device, and the reference part includes a receiving antenna which receives a radio signal from the transmission antenna.

19. The body-insertable device system according to claim 1, wherein the position presenting unit is located near the subject and includes a marker indicating an approaching position that the magnetic field generating unit approaches.

20. The body-insertable device system according to claim 19, wherein the marker includes a plurality of markers, and the plurality of markers can be distinguished by at least any of shape, symbol, character and color of markers.

21. The body-insertable device system according to claim 19, wherein the body-insertable device includes a transmission antenna which wirelessly transmits an image acquired by the imaging unit to outside the body-insertable device, and the position presenting unit includes a receiving antenna which receives a radio signal from the transmission antenna.

22. The body-insertable device system according to claim 1, further comprising a position/posture detecting unit which detects a position and a posture of the body-insertable device, and an image combining processing unit which combines a plurality of images picked up by the body-insertable device having a position and a posture, which are detected by the position/posture detecting unit based on a detection result of the position/posture detecting unit.

23. The body-insertable device system according to claim 22, wherein the image combining processing unit includes a correction part which corrects a distortion aberrations of the plurality of images.

24. The body-insertable device system according to claim 1, wherein the magnetic material is a permanent magnet, a battery or an electromagnet.

25. The body-insertable device system according to claim 1, further comprising:
an input unit which inputs desired designated position information specified from images acquired by the imaging unit;
a position/posture detecting unit which detects a position and a posture of the body-insertable device;
a position specifying unit which specifies an approaching position of the magnetic field generating unit based on the designated position information and the position and the posture of the body-insertable device detected by the position/posture detecting unit; and a specified position presenting unit which shows an approaching position specified by the position specifying unit.

26. A method for guiding a body-insertable device comprising an imaging unit for picking up images of the inside of a subject, and a magnet, and is guided by a magnetic field, the method comprising:
a position presenting step of visually presenting an intended location of a magnetic-field generating position on or near a body surface of the subject; and
a magnetic-field generating step of placing a magnetic field generating unit at the intended location and generating the magnetic field at the intended location presented in the position presenting step.

27. The body-insertable device guiding method according to claim 26, wherein the position presenting step and the magnetic-field generating step are repeatedly performed.

28. The body-insertable device guiding method according to claim 26, further comprising a posture changing step of changing a posture of the subject before or after the position presenting step or before or after the magnetic-field generating step.

29. The body-insertable device guiding method according to claim 26, further comprising a magnetic-field direction presenting step of visually presenting an orientation of a magnetic field generated at the intended location.

30. The body-insertable device guiding method according to claim 26, further comprising a magnetic-field intensity presenting step of visually presenting an intensity of a magnetic field generated at the intended location.

31. The body-insertable device guiding method according to claim 30, further comprising a body shape acquiring step of acquiring a body shape of the subject preceding to the position presenting step, and a magnetic field intensity determining step of determining an intensity of the magnetic field generated based on the body shape of the subject acquired in the body shape acquiring step preceding to the magnetic-field intensity presenting step.

32. The body-insertable device guiding method according to claim 26, further comprising:
- an image acquiring step of acquiring images of the insides of the subject by the body-insertable device which is guided by the action of the magnetic field generated in the magnetic-field generating step;
- a position detecting step of detecting a position of the body-insertable device when the images of the insides of the subject are acquired;
- a position designating step of designating a specific position of images of the insides of the subject acquired by the body-insertable device of which position is detected in the position detecting step;
- a position specifying step of specifying the intended location of a magnetic-field generating position for acquiring the image of the specific position specified in the position designating step based on the position of the body-insertable device;
- a specific position representing step of visually presenting the intended location specified in the position specifying step; and
- a specific magnetic field generating step of generating a magnetic field at the intended location presented in the specific position representing step.

33. The body-insertable device guiding method according to claim 26, further comprising:
- a position detecting step of detecting a position of the body-insertable device magnetically guided by a magnetic field generated in the magnetic field generating step;
- an image acquiring step of acquiring images of the insides of the subject by the body-insertable device of which a position is detected in the position detecting step;
- a position designating step of designating a specific position of the images of the insides of the subject, which are acquired by the body-insertable device of which a position is detected in the position detecting step;
- a position specifying step of specifying the intended location of a magnetic-field generating position to acquire the image of the specific position designated in the position designating step based on the position of the body-insertable device;
- a specific position presenting step of visually presenting the intended location specified in the position specifying step; and
- a specific magnetic field generating step of generating a magnetic field at the intended location visually presented in the specific position presenting step.

* * * * *